United States Patent
Fan et al.

(10) Patent No.: US 10,800,770 B1
(45) Date of Patent: Oct. 13, 2020

(54) CHROMAN DERIVATIVES HAVING ESTROGEN RECEPTOR DEGRADATION ACTIVITY AND USES THEREOF

(71) Applicant: ACCUTAR BIOTECHNOLOGY INC., Brooklyn, NY (US)

(72) Inventors: Jie Fan, New York, NY (US); Yimin Qian, Plainsboro, NJ (US); Wei He, Zionsville, IN (US); Ke Liu, Shanghai (CN)

(73) Assignee: Accutar Biotechnology Inc., Brooklyn, NY (US)

( * ) Notice: Subject to any disclaimer, the term of this patent is extended or adjusted under 35 U.S.C. 154(b) by 0 days.

(21) Appl. No.: 16/846,492

(22) Filed: Apr. 13, 2020

Related U.S. Application Data

(60) Provisional application No. 62/947,213, filed on Dec. 12, 2019.

(51) Int. Cl.
*C07D 401/04* (2006.01)
*A61K 31/454* (2006.01)
*C07D 413/14* (2006.01)
*A61P 35/00* (2006.01)

(52) U.S. Cl.
CPC ............ *C07D 413/14* (2013.01); *A61P 35/00* (2018.01)

(58) Field of Classification Search
CPC ........................... C07D 401/04; A61K 31/454
USPC ........................ 546/277.1, 175, 194; 514/323
See application file for complete search history.

(56) References Cited

U.S. PATENT DOCUMENTS 8,518,972 B2 * 8/2013 Man .......................... A61P 9/14
514/323

\* cited by examiner

*Primary Examiner* — Niloofar Rahmani
(74) *Attorney, Agent, or Firm* — Finnegan, Henderson, Farabow, Garrett & Dunner, LLP

(57) ABSTRACT

The present disclosure relates to novel compounds, pharmaceutical compositions containing such compounds, and their use in prevention and treatment of cancer and related diseases and conditions.

22 Claims, 10 Drawing Sheets

CHROMAN DERIVATIVES HAVING ESTROGEN RECEPTOR DEGRADATION ACTIVITY AND USES THEREOF

CROSS REFERENCE TO RELATED APPLICATIONS

This application claims benefit of priority of U.S. Provisional Patent Application No. 62/947,213 filed on Dec. 12, 2019, which is incorporated herein by reference in its entirety.

FIELD OF THE DISCLOSURE

The present disclosure relates to novel compounds, pharmaceutical compositions containing such compounds, and their use in prevention and treatment of diseases and conditions, e.g., cancer.

BACKGROUND OF THE DISCLOSURE

Estrogen, a female sex hormone, through binding to its cognate Estrogen receptors, ERα and ERβ, governs a wide range of physiological processes, e.g., the development of the female reproductive system, the maintenance of bone mass, and the protection of cardiovascular tissue and the central nervous system. Upon estrogen's binding to an estrogen receptor ("ER"), the receptor undergoes a conformational change resulting in its homodimerization. The ER homodimer then binds to estrogen-response elements ("EREs") that are present in the promoters of a specific set of target genes and regulates their expression with the help of transcriptional coregulators. Several thousand canonical ER target genes have been identified, many of which regulate cell proliferation and survival.

Because ER signaling is implicated in many pathways, it is well known that deregulation of ER signaling, specifically through ERα, results in uncontrolled cellular proliferation which eventually results into cancer. ER+ breast cancer accounts for approximately 75% of all breast cancers diagnosed, as well as some ovarian and endometrial cancers. The prevalence of ER+ cancer has led to decades of investigation and development of antiestrogens as therapeutic agents.

Antiestrogen (i.e., hormonal) therapy is the first choice for treatment of most ER+ breast cancers. There are three major classes of antiestrogen therapies, including aromatase inhibitors (e.g., letrozole and anastrozole); selective estrogen modulators (e.g., tamoxifen, toremifene, and raloxifene); and selective estrogen receptor degraders (e.g., fulvestrant). These classes of antiestrogen therapy operate by different mechanisms of action, such as inhibiting aromatase enzyme, competitively binding to ERα, and/or causing ERα degradation.

The aforementioned therapies may result in deleterious effects. For example, administration of aromatase inhibitors results in a decrease in bone mineral density, which can result in an increased risk of fractures. Administration of selective estrogen modulators can result in development of endometrial cancer and/or cardiovascular issues, e.g., deep thrombosis and pulmonary embolism. Additionally, the aforementioned therapies may suffer from insufficient clinical efficacy.

Accordingly, there exists a need to treat ER+ cancer without the harmful side effects known for current therapies. One approach to achieve this goal would be to utilize the naturally occurring cellular ubiquitin-mediated degradation. Without being bound to any theory, it is believed that ERα degradation may occur when both ERα and a ubiquitin ligase are bound and brought into close proximity.

Cereblon ("CRBN") E3 ubiquitin ligase is a ubiquitin ligase that CRBN forms an E3 ubiquitin ligase complex with damaged DNA binding protein 1 and Cullin 4. It functions as a substrate receptor by bringing the substrates to close proximity for ubiquitination and subsequent degradation by proteasomes. Recently, it has been discovered that small molecules drugs, e.g., thalidomide and its close analogs, lenalidomide and pomalidomide, can simultaneously interact with CRBN and some other proteins. In doing so, CRBN may be exploited for target protein degradation, such as IKZF1 and IKZF3. This is thought to account for the anti-myeloma effects of thalidomide and related compounds.

SUMMARY OF THE DISCLOSURE

In some embodiments, provided herein are compounds of Formula (I), stereoisomer or a mixture of stereoisomers, or a pharmaceutically acceptable salt, or hydrate thereof:

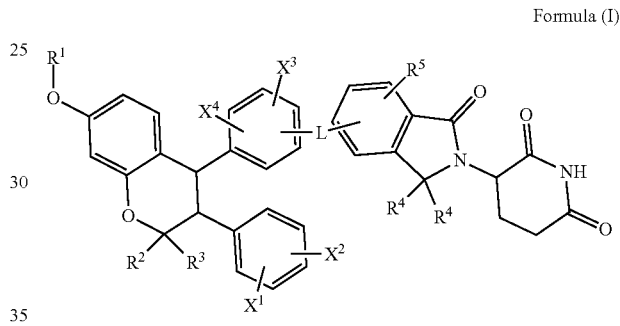

Formula (I)

wherein:

$R^1$ is selected from H, $C_1$-$C_6$ acyl, or $C_1$-$C_6$ alkyl, each of which is substituted with 0, 1, 2, or 3 $R^6$;

$R^2$ and $R^3$ are each independently selected from H, $C_1$-$C_3$ alkyl, or $C_1$-$C_3$ haloalkyl, each of which is substituted with 0, 1, 2, or 3 $R^6$;

each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo;

$R^5$ is selected from halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^6$;

$X^1$ and $X^2$ are each independently selected from H, halogen, cyano, $C_1$-$C_6$ alkyl, $C_1$-$C_6$ alkoxyl, or $C_1$-$C_6$ haloalkyl each of which is substituted with 0, 1, 2, or 3 $R^6$;

$X^3$ and $X^4$ are each independently selected from H or halo;

L is a linker of 1 to 22 carbon atoms in length, wherein one or more carbon atoms are each optionally and independently replaced by a group selected from C(O), O, N$R^7$, S, $C_2$-alkenyl, $C_2$-alkynyl, cycloalkyl, aryl, heterocycle, and heteroaryl, each of which is substituted with 0, 1, 2, or 3 $R^6$;

each $R^6$ is independently selected from $C_1$-$C_6$ alkyl, halo, cyano, and hydroxy, each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

In some embodiments, the compound of Formula (I) may encompass both the cis- and trans-isomers. In some embodiments, the compound of Formula (I) may be a mixture of cis- and trans-isomers. In some embodiments, the compound of Formula (I) may be cis-isomer.

In some embodiments, the compound of Formula (I) may encompass both stereoisomes and a mixture of stereoisomers. In some embodiments, the compound of Formula (I) is stereoisomer. In some embodiments, the compound of Formula (I) may encompass both racemic isomers and enantiomeric isomers.

In some embodiments, provided herein is the compound of Formula (I)*:

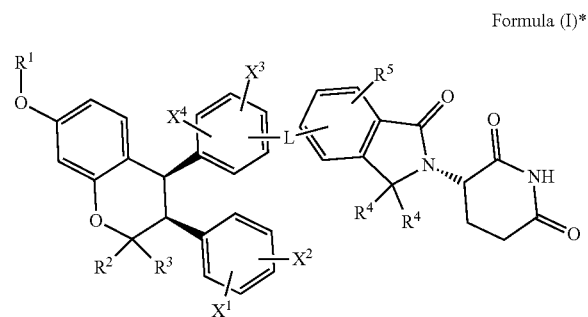

Formula (I)*

Also provided herein is a method of treating cancer in a subject in need thereof, comprising administering to said subject an effective amount of a compound disclosed herein. In some embodiments, the cancer is selected from breast cancer, lung cancer, ovarian cancer, endometrial cancer, prostate cancer, and esophageal cancer.

BRIEF DESCRIPTION OF THE FIGURES

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosures.

DETAILED DESCRIPTION

Definitions

Figure 1A:
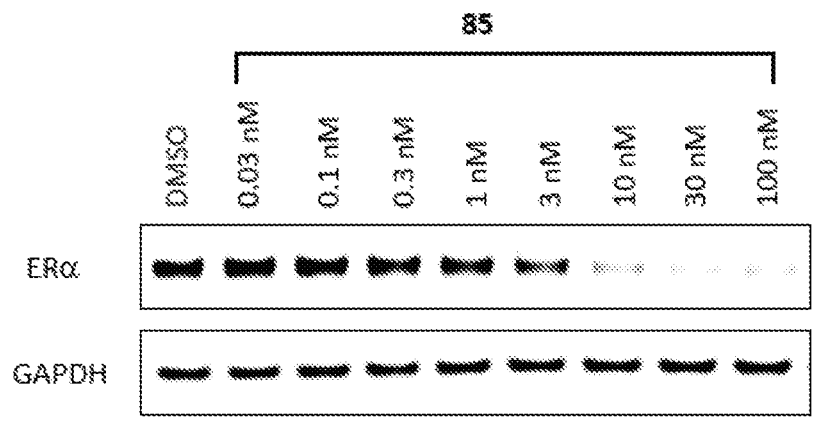
FIGS. 1A to 1D illustrate the ERα degradative activity of exemplary Compounds 85, 60, 32 and 52 of the present disclosure in a T47D cell line 6 hours after administration.
Figure 1B:
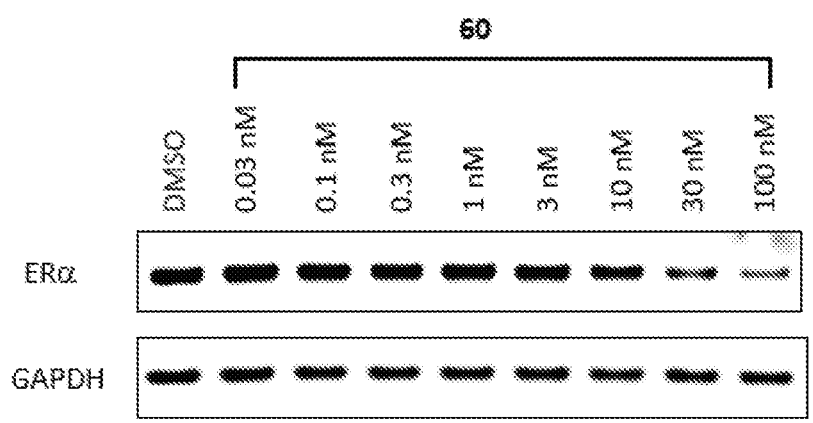
Figure 1C:
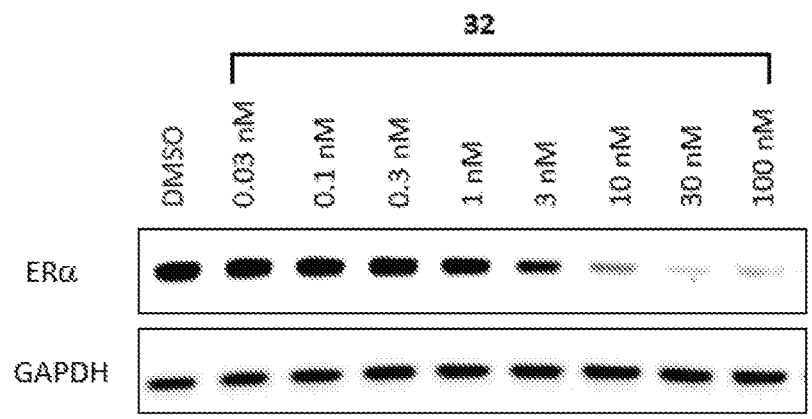
Figure 1D:
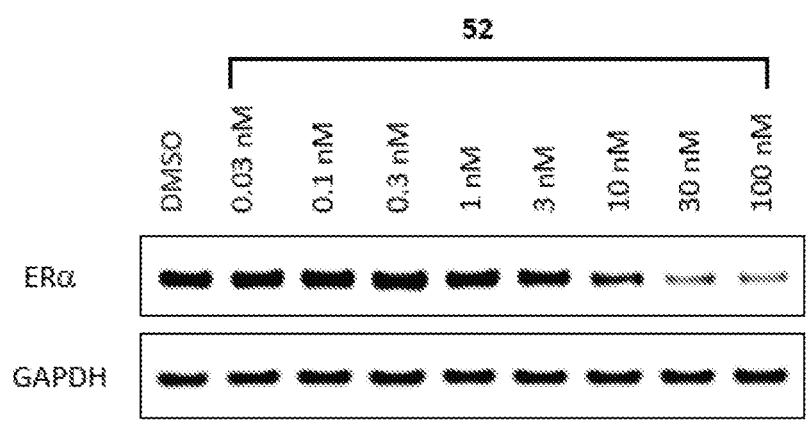

As used herein, "cancer" refers to diseases, disorders, and conditions that involve abnormal cell growth with the potential to invade or spread to other parts of the body. Exemplary cancers, include, but are not limited to, breast cancer, lung cancer, ovarian cancer, endometrial cancer, prostate cancer, and esophageal cancer.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated straight or branched hydrocarbon having at least one carbon-carbon triple bond, such as a straight or branched group of 2-8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include but are not limited to a monocyclic aromatic ring system, wherein the ring comprises 6 carbon atoms, referred to herein as "$C_6$-aryl."

The term "cyano" as used herein refers to —CN.

The term "cycloalkyl" as used herein refers to a saturated or unsaturated cyclic, bicyclic, or bridged bicyclic hydrocarbon group of 3-16 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "$(C_2-C_5)$heteroaryl."

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/ risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein are compounds of Formula (I), a stereoisomer or a mixture of stereoisomers, a pharmaceutically acceptable salt, or hydrate thereof:

Formula (I)

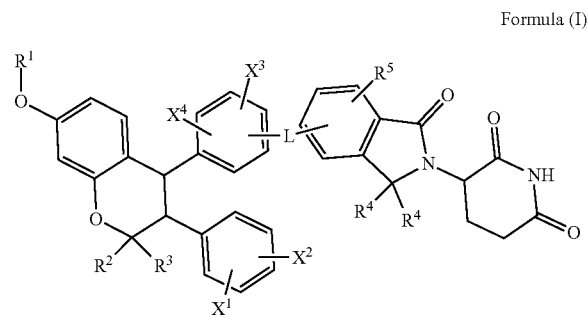

wherein:

$R^1$ is selected from H, $C_1$-$C_6$ acyl, or $C_1$-$C_6$ alkyl, each of which is substituted with 0, 1, 2, or 3 $R^6$;

$R^2$ and $R^3$ are each independently selected from H, $C_1$-C3 alkyl, or $C_1$-$C_3$ haloalkyl, each of which is substituted with 0, 1, 2, or 3 $R^6$;

each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo;

$R^5$ is selected from halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^6$; $X^1$ and $X^2$ are each independently selected from H, halogen, cyano, $C_1$-$C_6$ alkyl, $C_1$-$C_6$ alkoxyl, or $C_1$-$C_6$ haloalkyl each of which is substituted with 0, 1, 2, or 3 $R^6$;

$X^3$ and $X^4$ are each independently selected from H or halo;

L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is substituted with 0, 1, 2, or 3 $R^6$;

each $R^6$ is independently selected from $C_1$-$C_6$ alkyl, halo, cyano, and hydroxy, each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

In some embodiments, $R^1$ is selected from H, or $C_1$-$C_6$ alkyl, each of which is substituted with 0, 1, 2, or 3 $R^6$. In some embodiments, $R^1$ may be selected from H or methyl, each of which is substituted with 0, 1, 2, or 3 $R^6$. In some embodiments, $R^1$ may each be independently H or methyl.

In some embodiments, $R^1$ may be H. In some embodiments, $R^1$ may be methyl.

In some embodiments, $R^2$ and $R^3$ are each independently selected from H, $C_1$-C3 alkyl, or $C_1$-$C_3$ haloalkyl, each of which is substituted with 0, 1, 2, or 3 $R^6$. In some embodiments, $R^2$ and $R^3$ are each independently selected from H and methyl, each of which is substituted with 0, 1, 2, or 3 $R^6$. In some embodiments, $R^2$ and $R^3$ are each independently selected from H and methyl.

In some embodiments, $R^2$ may be H and $R^3$ may be H. In some embodiments, $R^2$ may be H and $R^3$ may be methyl. In some embodiments, $R^2$ may be methyl and $R^3$ may be H. In some embodiments, $R^2$ may be methyl and $R^3$ may be methyl.

In some embodiments, each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo. In some embodiments, each $R^4$ is independently selected from H, hydroxyl, $C_1$-$C_3$ alkyl, $C_1$-$C_3$ alkoxyl, or $C_1$-$C_3$ haloalkyl, or two $R^4$ groups are taken together to form an oxo. In some embodiments, $R^4$ is H. In some embodiments, two $R^4$ groups are taken together to form an oxo.

In some embodiments, $R^5$ is selected from halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^6$. In some embodiments, $R^5$ is selected from halogen, hydroxy, $C_1$-$C_3$ alkyl, $C_1$-$C_3$ alkoxy, $C_1$-$C_3$ haloalkyl, —N($R^7$)$_2$, and —CN. In some embodiments, $R^5$ is selected from halogen. In some embodiments, $R^5$ may be F.

In some embodiments, $X^1$ and $X^2$ are each independently selected from H, halogen, cyano, $C_1$-$C_6$ alkyl, $C_1$-$C_6$ alkoxyl, or $C_1$-$C_6$ haloalkyl, each of which is substituted with 0, 1, 2, or 3 $R^6$. In some embodiments, $X^1$ and $X^2$ are each independently selected from H, halogen, cyano, $C_1$-$C_6$ alkyl, $C_1$-$C_6$ alkoxyl, or $C_1$-$C_6$ haloalkyl. In some embodiments, $X^1$ and $X^2$ are each independently selected from H, F, CN, methyl, methoxy, trifluoromethyl.

In some embodiments, $X^1$ is H and $X^2$ is H. In some embodiments, $X^1$ is F and $X^2$ is F. In some embodiments, $X^1$ is H and $X^2$ is methyl. In some embodiments, $X^1$ is methyl and $X^2$ is H. In some embodiments, $X^1$ is H and $X^2$ is F. In some embodiments, $X^1$ is F and $X^2$ is H. In some embodiments, $X^1$ is H and $X^2$ is methoxy. In some embodiments, $X^1$ is methoxy and $X^2$ is H. In some embodiments, $X^1$ is F and $X^2$ is methyl. In some embodiments, $X^1$ is methyl and $X^2$ is F. In some embodiments, $X^1$ is F and $X^2$ is methoxy. In some embodiments, $X^1$ is methoxy and $X^2$ is F. In some embodiments, $X^1$ is F and $X^2$ is trifluoromethyl. In some embodiments, $X^1$ is trifluoromethyl and $X^2$ is F.

In some embodiments, $X^3$ and $X^4$ are each independently selected from H or halo. In some embodiments, $X^3$ and $X^4$ are each independently selected from H or F.

In some embodiments, $X^3$ is H and $X^4$ is H. In some embodiments, $X^3$ is F and $X^4$ is F. In some embodiments, $X^3$ is H and $X^4$ is F. In some embodiments, $X^3$ is F and $X^4$ is H.

In some embodiments, L may be linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L may be linker of 1 to 20 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L may be linker of 1 to 18 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be linker of 1 to 16 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be a linker of 1 to 14 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be a linker of 1 to 12 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be a linker of 1 to 10 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵.

In some embodiments, L may be a linker of 1 to 8 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be a linker of 1 to 6 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L may be linker of 1 to 4 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵.

In some embodiments, L may be a linker wherein two carbon atoms are each independently replaced by a heterocycle, each of which is independently substituted with 0, 1, 2, or 3 R⁵. In some embodiments, L may be a linker wherein one carbon atom is replaced by a heterocycle and one carbon atom is replaced by a cycloalkyl, each of which is independently substituted with 0, 1, 2, or 3 R⁵. In some embodiments, L may be a linker wherein more than one carbon atoms are each independently replaced by a group selected from C(O), O, NR⁴, S, C₂-alkenyl, C₂-alkynyl, cycloalkyl, aryl, heterocycle, and heteroaryl, each of which is substituted with 0, 1, 2, or 3 R⁵. In some embodiments, L may be a linker wherein more than one carbon atoms are each independently replaced by a group selected from C(O), O, and NR⁴, each of which is substituted with 0, 1, 2, or 3 R⁵.

In some embodiments, L may be

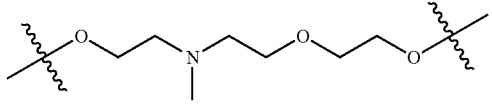

In some embodiments, L may be

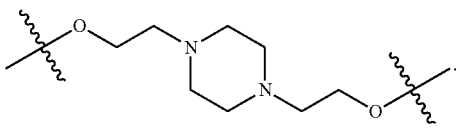 [SMILES: *OCCN1CCN(CCO*)CC1]

In some embodiments, L may be

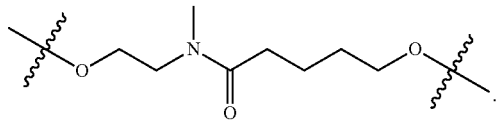 [SMILES: *OCCCCC(=O)N(C)CCO*]

In some embodiments, L may be

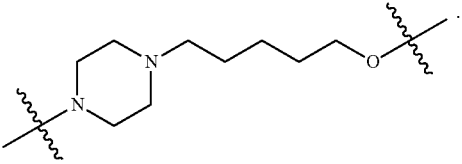 [SMILES: *OCCCCCN1CCN(*)CC1]

In some embodiments, L may be

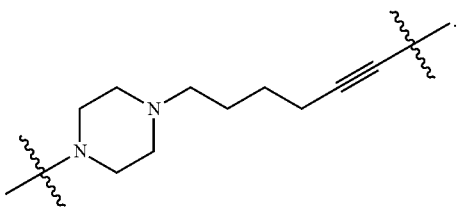 [SMILES: *C#CCCCCN1CCN(*)CC1]

In some embodiments, L may be

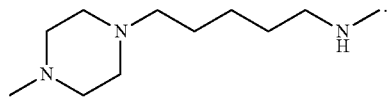

In some embodiments, L may be

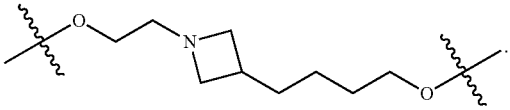 [SMILES: *OCCCCC1CN(CCO*)C1]

In some embodiments, L may be

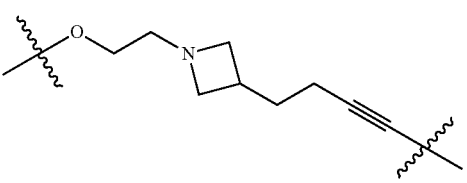

In some embodiments, L may be

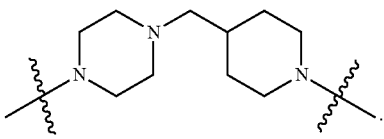 [SMILES: *N1CCC(CN2CCN(*)CC2)CC1]

In some embodiments, L may be

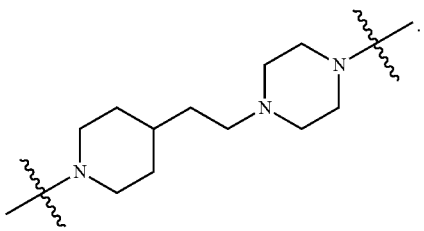 [SMILES: *N1CCC(CCN2CCN(*)CC2)CC1]

In some embodiments, L may be

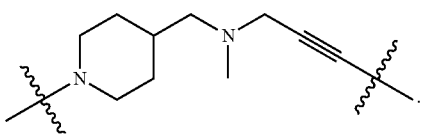 [SMILES: *C#CCN(C)CC1CCN(*)CC1]

In some embodiments, the compound of formula (N) is cis-isomer.

In some embodiments, the compound of formula (I) is a stereoisomer.

In some embodiments, provided herein is a compound of formula (I)*:

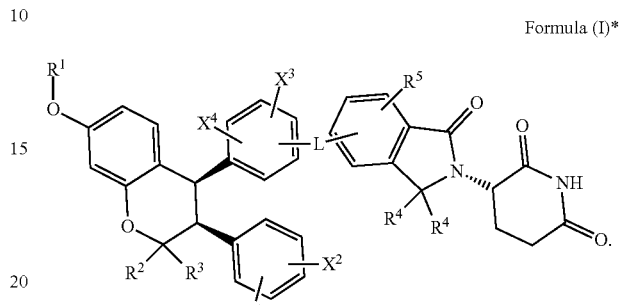

Formula (I)*

In some embodiments, provided herein is a compound, or pharmaceutically acceptable salt thereof, chosen from the compounds listed in Table 1.

TABLE 1

Exemplary Compound of the Present Disclosure

| Cpd # | Chemical Structure | IUPAC Name |
|---|---|---|
| 1 | 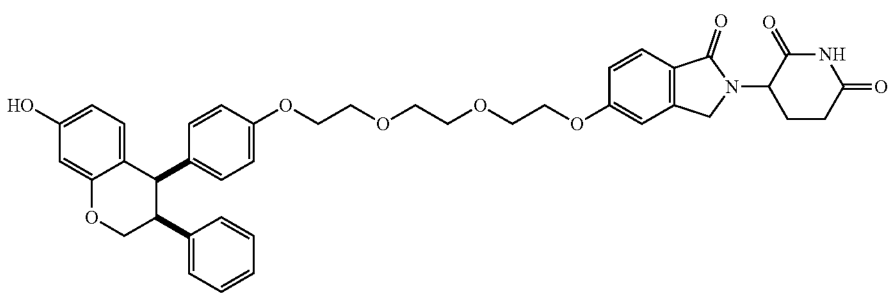 [SMILES: O=C1CCC(N2Cc3cc(OCCOCCOCCOc4ccc([C@@H]5c6ccc(O)cc6OC[C@@H]5c5ccccc5)cc4)ccc3C2=O)C(=O)N1] | cis-3-(5-(2-(2-(2-(4-(7-hydroxy-3-phenylchroman-4-yl)phenoxy)ethoxy)ethoxy)ethoxy)-1-oxoisoindolin-2-yl)piperidine-2,6-dione |
| 2 | 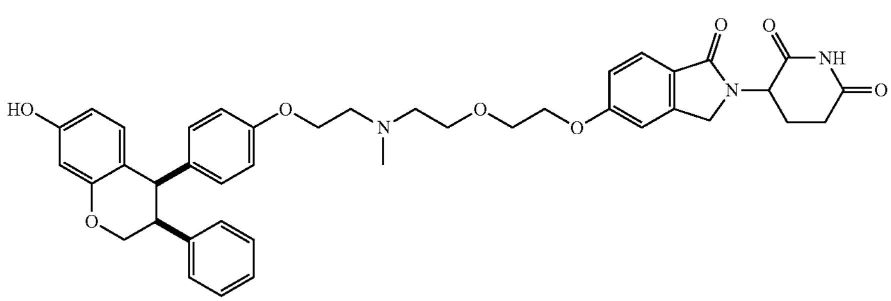 | cis-3-(5-(2-(2-((2-(4-(7-hydroxy-3-phenylchroman-4-yl)phenoxy)ethyl)(methyl)amino)ethoxy)ethoxy)-1-oxoisoindolin-2-yl)piperidine-2,6-dione |
| 3 | 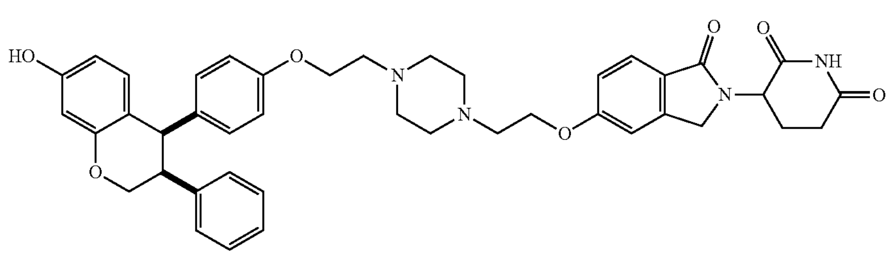 [SMILES: O=C1CCC(N2Cc3cc(OCCN4CCN(CCOc5ccc([C@@H]6c7ccc(O)cc7OC[C@@H]6c6ccccc6)cc5)CC4)ccc3C2=O)C(=O)N1] | cis-3-(5-(2-(4-(2-(4-(7-hydroxy-3-phenylchroman-4-yl)phenoxy)ethyl)piperazin-1-yl)ethoxy)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 4 | 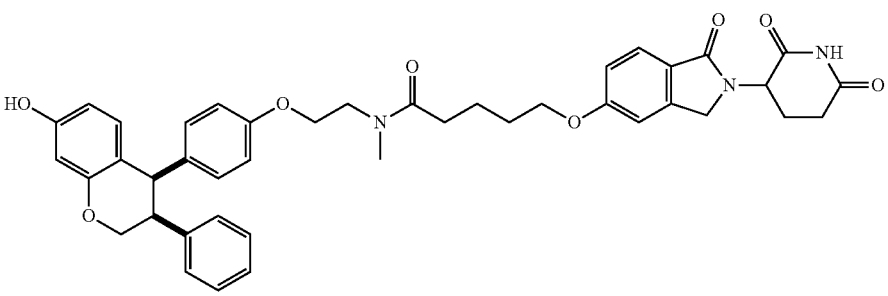 [SMILES: CN(CCOc1ccc([C@@H]2c3ccc(O)cc3OC[C@@H]2c2ccccc2)cc1)C(=O)CCCCOc1ccc2c(c1)CN(C1CCC(=O)NC1=O)C2=O] | cis-5-((2-(2,6-dioxo-piperidin-3-yl)-1-oxoisoindolin-5-yl)oxy)-N-(2-(4-(7-hydroxy-3-phenyl-chroman-4-yl)phenoxy)ethyl)-N-methylpentanamide |
| 5 | 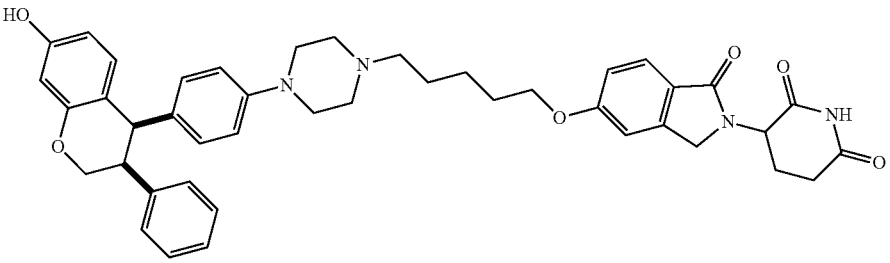 [SMILES: O=C1CCC(N2Cc3cc(OCCCCCN4CCN(c5ccc([C@@H]6c7ccc(O)cc7OC[C@@H]6c6ccccc6)cc5)CC4)ccc3C2=O)C(=O)N1] | cis-3-(5-((5-(4-(4-(7-hydroxy-3-phenylchroman-4-yl)phenyl)piperazin-1-yl)pentyl)oxy)-1-oxoisoindolin-2-yl)piperidine-2,6-dione |
| 6 | 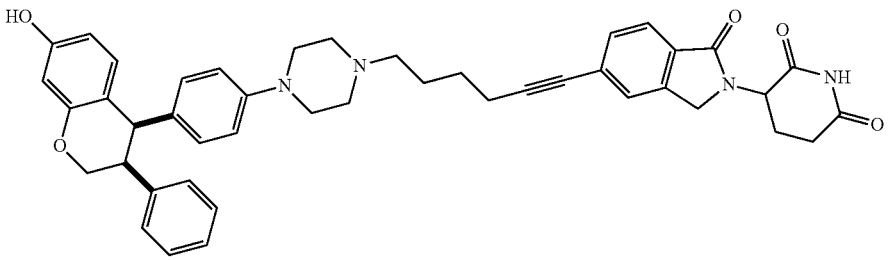 [SMILES: O=C1CCC(N2Cc3cc(C#CCCCCN4CCN(c5ccc([C@@H]6c7ccc(O)cc7OC[C@@H]6c6ccccc6)cc5)CC4)ccc3C2=O)C(=O)N1] | cis-3-(5-(6-(4-(4-(7-hydroxy-3-phenylchroman-4-yl)phenyl)piperazin-1-yl)hex-1-yn-1-yl)-1-oxoisoindolin-2-yl)piperidine-2,6-dione |
| 7 | 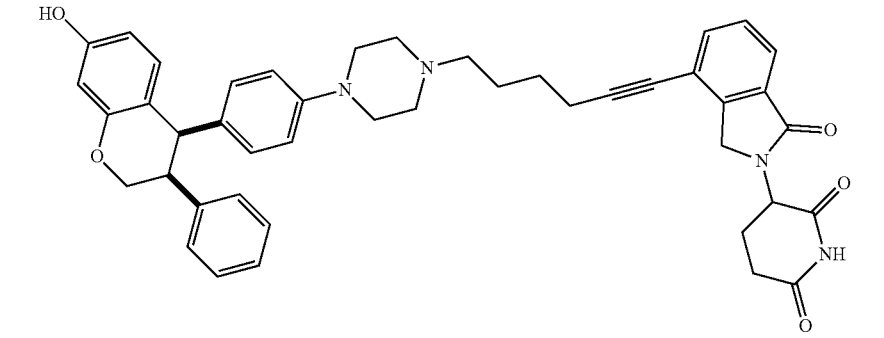 [SMILES: O=C1CCC(N2Cc3c(C#CCCCCN4CCN(c5ccc([C@@H]6c7ccc(O)cc7OC[C@@H]6c6ccccc6)cc5)CC4)cccc3C2=O)C(=O)N1] | cis-3-(4-(6-(4-(4-(7-hydroxy-3-phenylchroman-4-yl)phenyl)piperazin-1-yl)hex-1-yn-1-yl)-1-oxoisoindolin-2-yl)piperidine-2,6-dione |
| 8 | 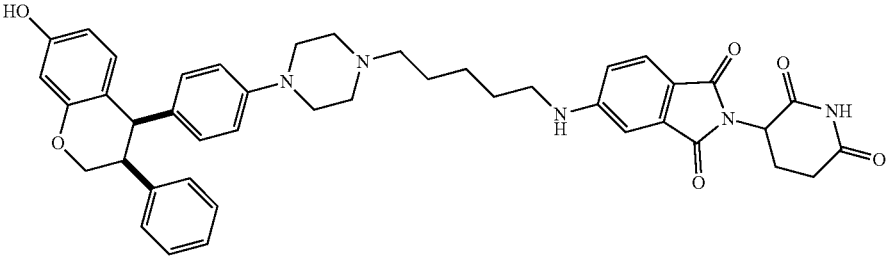 [SMILES: O=C1CCC(N2C(=O)c3ccc(NCCCCCN4CCN(c5ccc([C@@H]6c7ccc(O)cc7OC[C@@H]6c6ccccc6)cc5)CC4)cc3C2=O)C(=O)N1] | cis-2-(2,6-dioxopiperidin-3-yl)-5-((5-(4-(4-(7-hydroxy-3-phenylchroman-4-yl)phenyl)piperazin-1-yl)pentyl)amino)iso-indoline-1,3-dione |

TABLE 1-continued

Exemplary Compound of the Present Disclosure

| Cpd # | Chemical Structure | IUPAC Name |
|---|---|---|
| 9 | 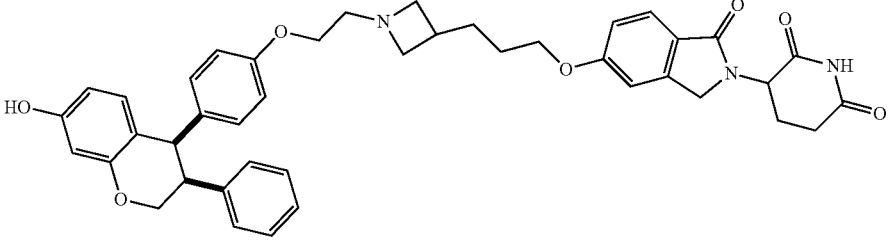 [SMILES: O=C1CCC(N2Cc3cc(OCCCC4CN(CCOc5ccc([C@@H]6c7ccc(O)cc7OC[C@@H]6c6ccccc6)cc5)C4)ccc3C2=O)C(=O)N1] | cis-3-(5-(3-(1-(2-(4-(7-hydroxy-3-phenylchroman-4-yl)phenoxy)ethyl)azetidin-3-yl)propoxy)-1-oxoisoindolin-2-yl)piperidine-2,6-dione |
| 10 | 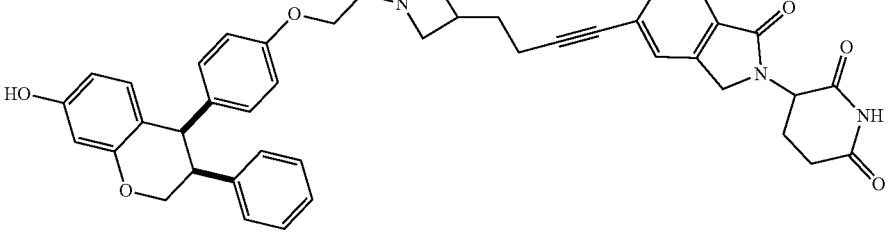 | cis-3-(5-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione |
| 11 | 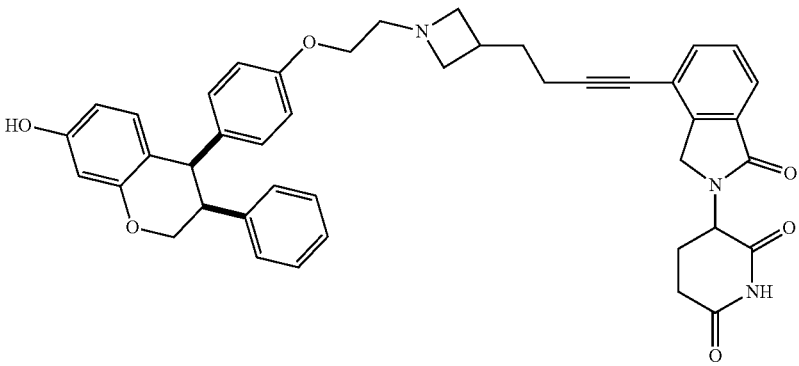 [SMILES: O=C1CCC(N2Cc3c(C#CCCC4CN(CCOc5ccc([C@@H]6c7ccc(O)cc7OC[C@@H]6c6ccccc6)cc5)C4)cccc3C2=O)C(=O)N1] | cis-3-(4-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione |
| 12 | 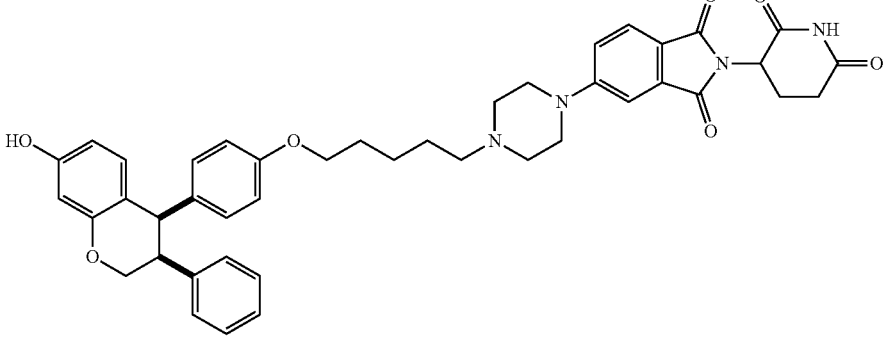 | cis-2-(2,6-dioxopiperidin-3-yl)-5-(4-(5-(4-(7-hydroxy-3-phenylchroman-4-yl)phenoxy)pentyl)piperazin-1-yl)isoindoline-1,3-dione |

TABLE 1-continued

Exemplary Compound of the Present Disclosure

| Cpd # | Chemical Structure | IUPAC Name |
|---|---|---|
| 13 | 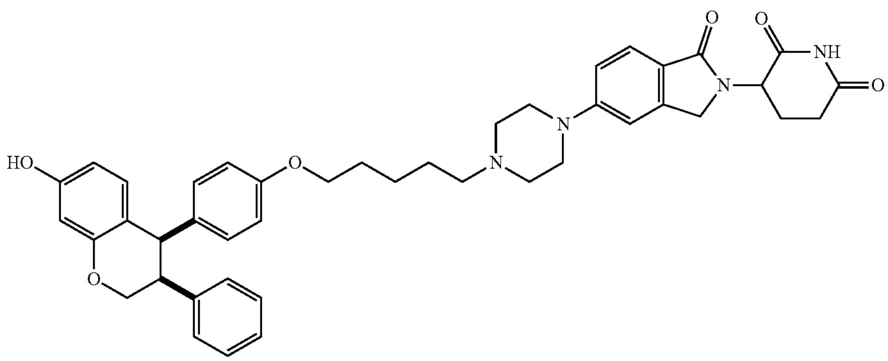 [SMILES: O=C1CCC(N2Cc3cc(N4CCN(CCCCCOc5ccc([C@@H]6c7ccc(O)cc7OC[C@@H]6c6ccccc6)cc5)CC4)ccc3C2=O)C(=O)N1] | cis-3-(5-(4-(5-(4-(7-hydroxy-3-phenylchroman-4-yl)phenoxy)pentyl)piperazin-1-yl)-1-oxoisoindolin-2-yl)piperidine-2,6-dione |
| 14 | 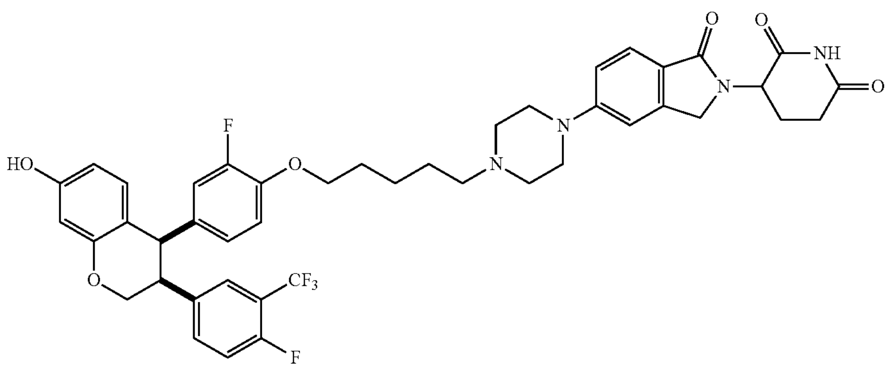 [SMILES: O=C1CCC(N2Cc3cc(N4CCN(CCCCCOc5ccc([C@@H]6c7ccc(O)cc7OC[C@@H]6c6ccc(F)c(C(F)(F)F)c6)cc5F)CC4)ccc3C2=O)C(=O)N1] | cis-3-(5-(4-(5-(2-fluoro-4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione |
| 15 | 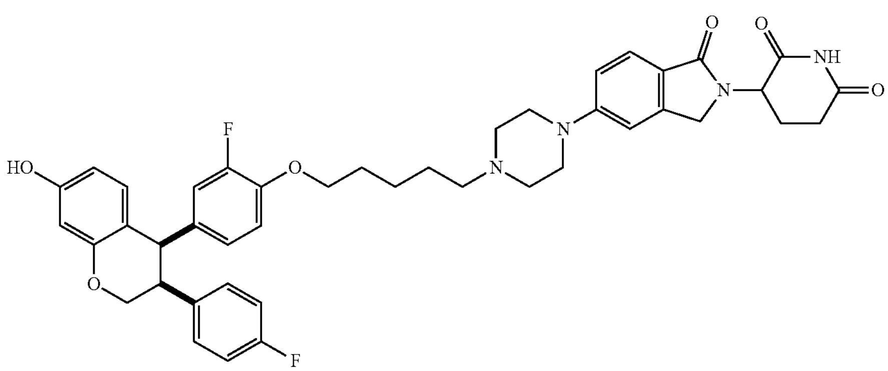 [SMILES: O=C1CCC(N2Cc3cc(N4CCN(CCCCCOc5ccc([C@@H]6c7ccc(O)cc7OC[C@@H]6c6ccc(F)cc6)cc5F)CC4)ccc3C2=O)C(=O)N1] | cis-3-(5-(4-(5-(2-fluoro-4-(3-(4-fluorophenyl)-7-hydroxychroman-4-yl)phenoxy)pentyl)piperazin-1-yl)-1-oxoisoindolin-2-yl)piperidine-2,6-dione |
| 16 | 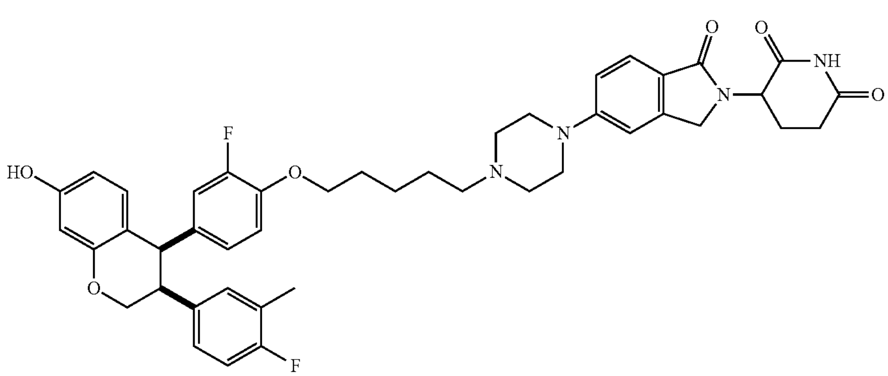 | cis-3-(5-(4-(5-(2-fluoro-4-(3-(4-fluoro-3-methylphenyl)-7-hydroxychroman-4-yl)phenoxy)pentyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 17 | 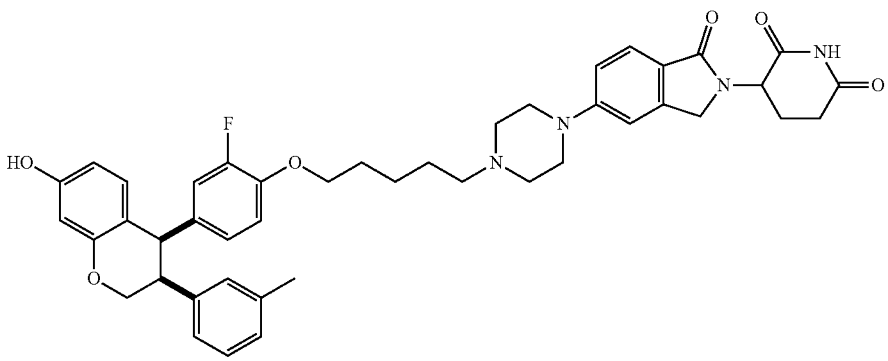 [SMILES: Cc1cccc([C@H]2COc3cc(O)ccc3[C@H]2c2ccc(OCCCCCN3CCN(c4ccc5c(c4)CN(C4CCC(=O)NC4=O)C5=O)CC3)c(F)c2)c1] | cis-3-(5-(4-(5-(2-fluoro-4-(7-hydroxy-3-(m-tolyl)chroman-4-yl)phenoxy)pentyl)piperazin-1-yl)-1-oxoisoindolin-2-yl)piperidine-2,6-dione |
| 18 | 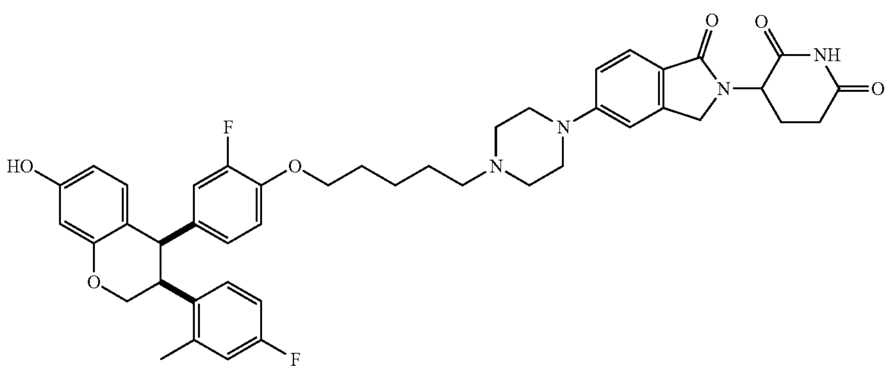 [SMILES: Cc1cc(F)ccc1[C@H]1COc2cc(O)ccc2[C@H]1c1ccc(OCCCCCN2CCN(c3ccc4c(c3)CN(C3CCC(=O)NC3=O)C4=O)CC2)c(F)c1] | cis-3-(5-(4-(5-(2-fluoro-4-(3-(4-fluoro-2-methylphenyl)-7-hydroxychroman-4-yl)phenoxy)pentyl)piperazin-1-yl)-1-oxoisoindolin-2-yl)piperidine-2,6-dione |
| 19 | 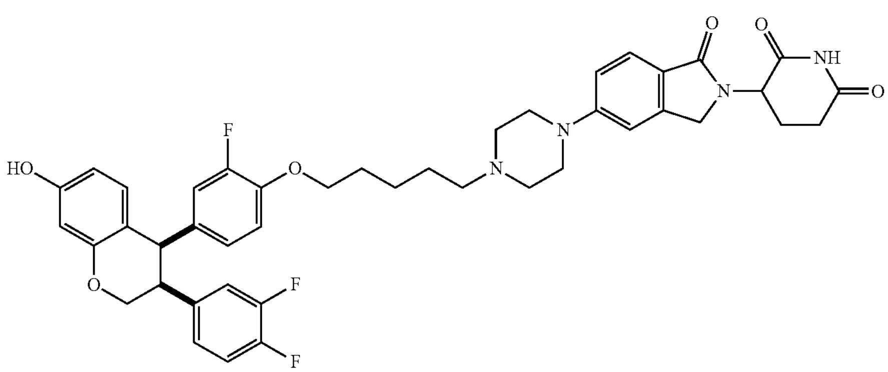 [SMILES: O=C1CCC(N2Cc3cc(N4CCN(CCCCCOc5ccc([C@@H]6c7ccc(O)cc7OC[C@@H]6c6ccc(F)c(F)c6)cc5F)CC4)ccc3C2=O)C(=O)N1] | cis-3-(5-(4-(5-(4-(3-(3,4-difluorophenyl)-7-hydroxychroman-4-yl)-2-fluorophenoxy)pentyl)piperazin-1-yl)-1-oxoisoindolin-2-yl)piperidine-2,6-dione |
| 20 | 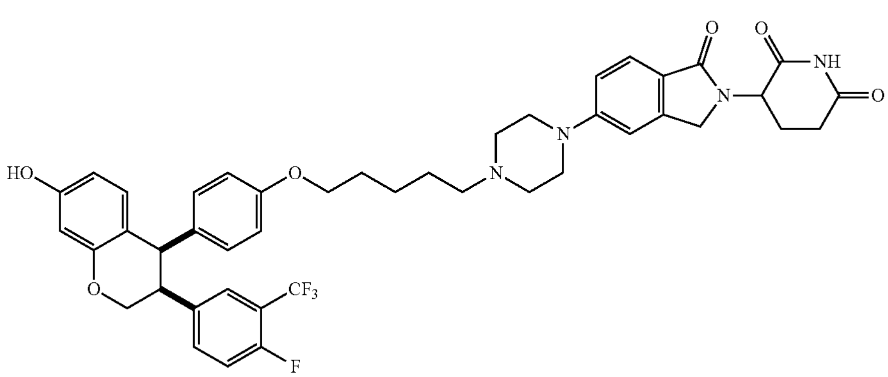 [SMILES: O=C1CCC(N2Cc3cc(N4CCN(CCCCCOc5ccc([C@@H]6c7ccc(O)cc7OC[C@@H]6c6ccc(F)c(C(F)(F)F)c6)cc5)CC4)ccc3C2=O)C(=O)N1] | cis-3-(5-(4-(5-(4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 21 | 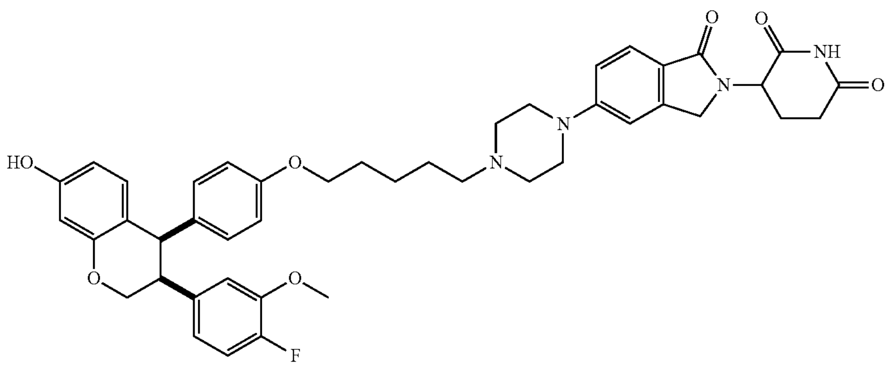 [SMILES: COc1cc([C@H]2COc3cc(O)ccc3[C@H]2c2ccc(OCCCCCN3CCN(c4ccc5c(c4)CN(C4CCC(=O)NC4=O)C5=O)CC3)cc2)ccc1F] | cis-3-(5-(4-(5-(4-(3-(4-fluoro-3-methoxyphenyl)-7-hydroxychroman-4-yl)phenoxy)pentyl)piperazin-1-yl)-1-oxoisoindolin-2-yl)piperidine-2,6-dione |
| 22 | 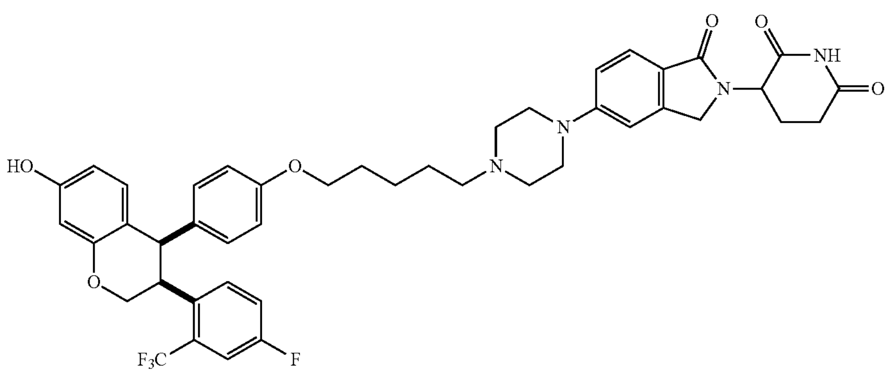 [SMILES: O=C1CCC(N2Cc3cc(N4CCN(CCCCCOc5ccc([C@@H]6c7ccc(O)cc7OC[C@@H]6c6ccc(F)cc6C(F)(F)F)cc5)CC4)ccc3C2=O)C(=O)N1] | cis-3-(5-(4-(5-(4-(3-(4-fluoro-2-(trifluoromethyl)phenyl)-7-hydroxychroman-4-yl)phenoxy)pentyl)piperazin-1-yl)-1-oxoisoindolin-2-yl)piperidine-2,6-dione |
| 23 | 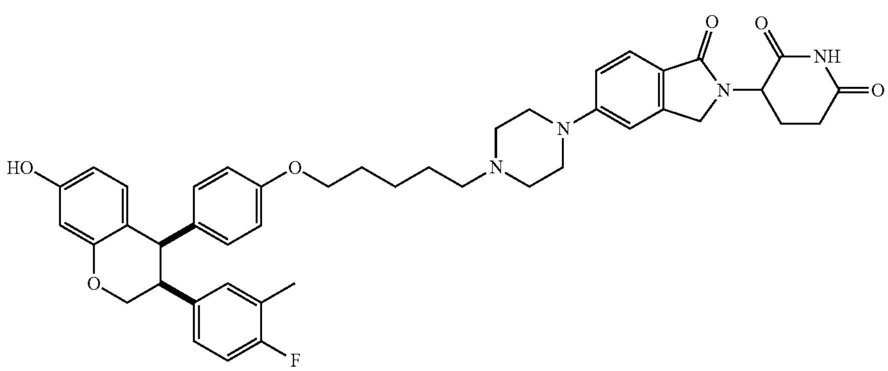 [SMILES: Cc1cc([C@H]2COc3cc(O)ccc3[C@H]2c2ccc(OCCCCCN3CCN(c4ccc5c(c4)CN(C4CCC(=O)NC4=O)C5=O)CC3)cc2)ccc1F] | cis-3-(5-(4-(5-(4-(3-(4-fluoro-3-methylphenyl)-7-hydroxychroman-4-yl)phenoxy)pentyl)piperazin-1-yl)-1-oxoisoindolin-2-yl)piperidine-2,6-dione |
| 24 | 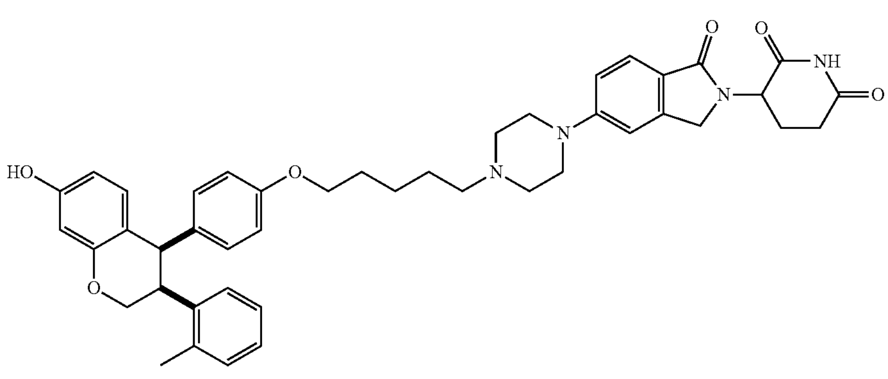 [SMILES: Cc1ccccc1[C@H]1COc2cc(O)ccc2[C@H]1c1ccc(OCCCCCN2CCN(c3ccc4c(c3)CN(C3CCC(=O)NC3=O)C4=O)CC2)cc1] | cis-3-(5-(4-(5-(4-(7-hydroxy-3-(o-tolyl)chroman-4-yl)phenoxy)pentyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 25 | 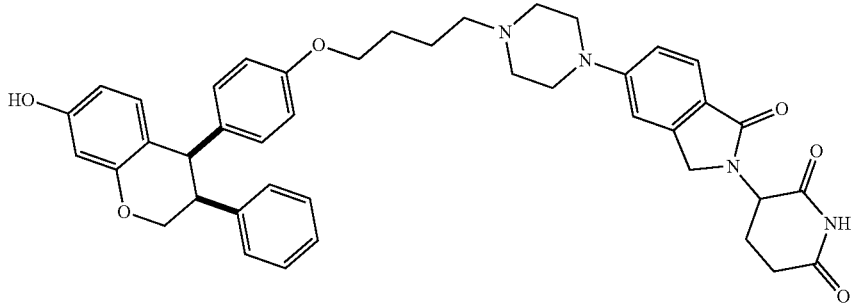 [SMILES: O=C1CCC(N2Cc3cc(N4CCN(CCCCOc5ccc([C@@H]6c7ccc(O)cc7OC[C@@H]6c6ccccc6)cc5)CC4)ccc3C2=O)C(=O)N1] | cis-3-(5-(4-(4-(4-(7-hydroxy-3-phenylchroman-4-yl)phenoxy)butyl)piperazin-1-yl)-1-oxoisoindolin-2-yl)piperidine-2,6-dione |
| 26 | 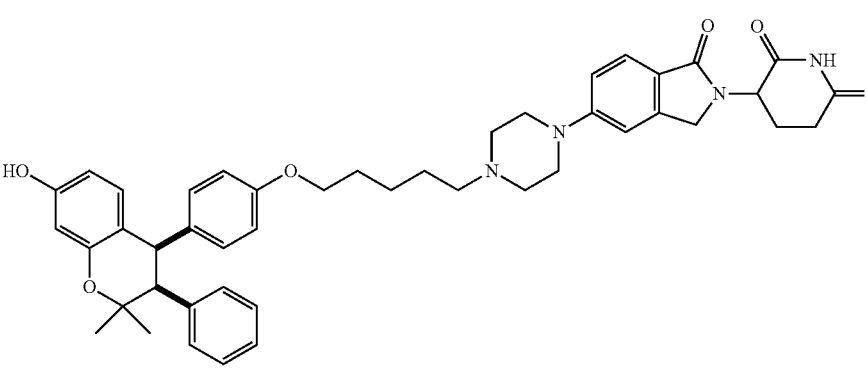 | cis-3-(5-(4-(5-(4-(7-hydroxy-2,2-dimethyl-3-phenylchroman-4-yl)phenoxy)pentyl)piperazin-1-yl)-1-oxoisoindolin-2-yl)piperidine-2,6-dione |
| 27 | 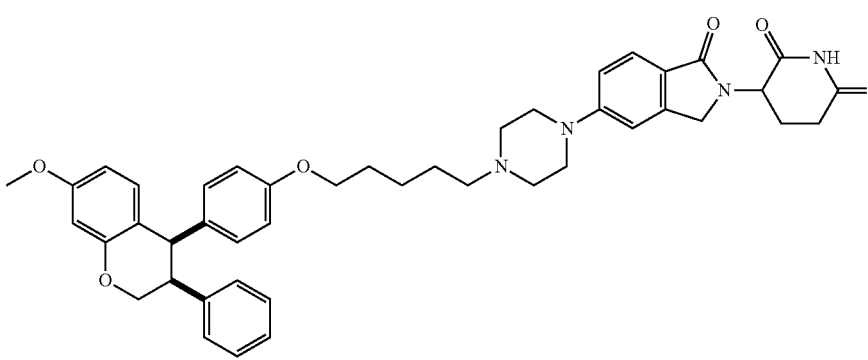 | cis-3-(5-(4-(5-(4-(7-methoxy-3-phenylchroman-4-yl)phenoxy)pentyl)piperazin-1-yl)-1-oxoisoindolin-2-yl)piperidine-2,6-dione |
| 28 | 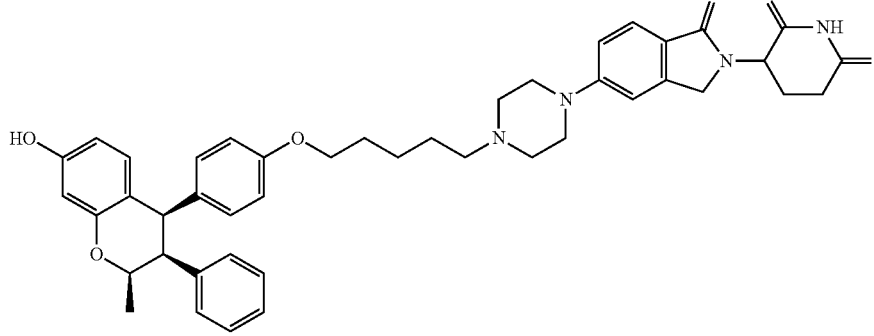 | 3-(5-(4-(5-(4-((2R,3S,4R)-7-hydroxy-2-methyl-3-phenylchroman-4-yl)phenoxy)pentyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 29 | 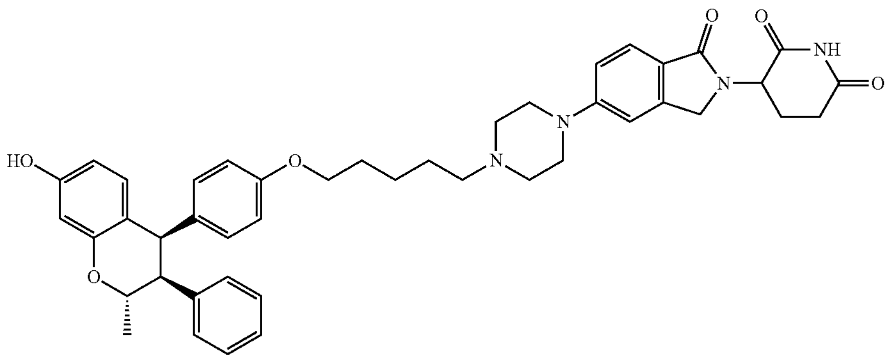 [SMILES: C[C@@H]1Oc2cc(O)ccc2[C@@H](c2ccc(OCCCCCN3CCN(c4ccc5c(c4)CN(C4CCC(=O)NC4=O)C5=O)CC3)cc2)[C@H]1c1ccccc1] | 3-(5-(4-(5-(4-((2S,3S,4R)-7-hydroxy-2-methyl-3-phenylchroman-4-yl)phenoxy)pentyl)piperazin-1-yl)-1-oxoisoindolin-2-yl)piperidine-2,6-dione |
| 30 | 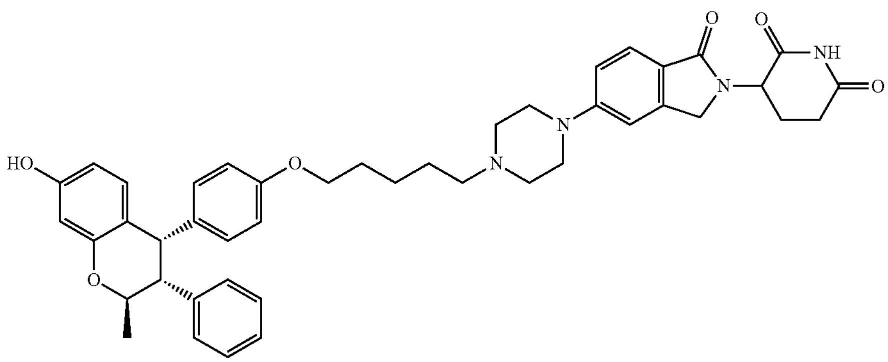 | 3-(5-(4-(5-(4-((2R,3R,4S)-7-hydroxy-2-methyl-3-phenylchroman-4-yl)phenoxy)pentyl)piperazin-1-yl)-1-oxoisoindolin-2-yl)piperidine-2,6-dione |
| 31 | 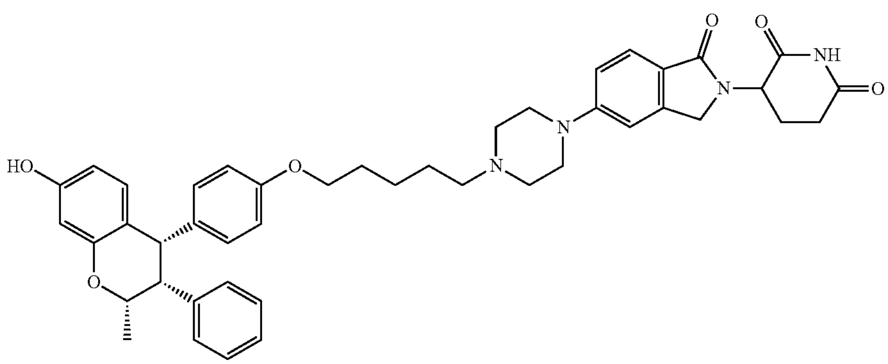 [SMILES: C[C@@H]1Oc2cc(O)ccc2[C@H](c2ccc(OCCCCCN3CCN(c4ccc5c(c4)CN(C4CCC(=O)NC4=O)C5=O)CC3)cc2)[C@@H]1c1ccccc1] | 3-(5-(4-(5-(4-((2S,3R,4S)-7-hydroxy-2-methyl-3-phenylchroman-4-yl)phenoxy)pentyl)piperazin-1-yl)-1-oxoisoindolin-2-yl)piperidine-2,6-dione |
| 32 | 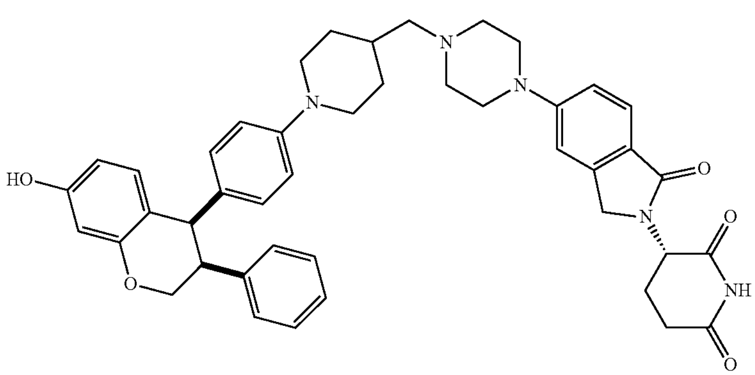 | cis-(S)-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 33 | 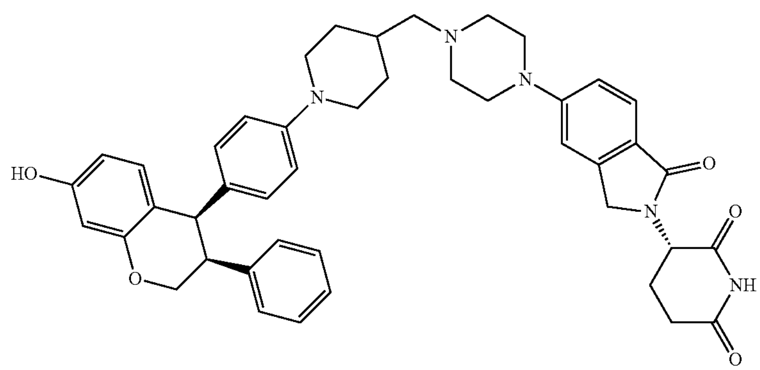 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)ccc3C2=O)C(=O)N1] | (S)-3-(5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 34 | 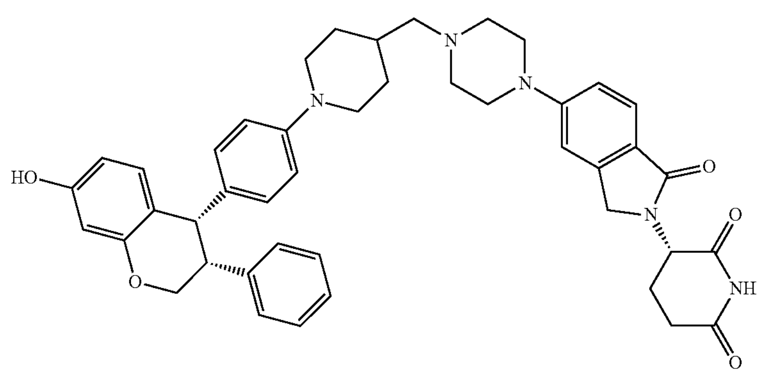 [SMILES: O=C1CC[C@H](N2Cc3cc(N4CCN(CC5CCN(c6ccc([C@H]7c8ccc(O)cc8OC[C@H]7c7ccccc7)cc6)CC5)CC4)ccc3C2=O)C(=O)N1] | (S)-3-(5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |
| 35 | 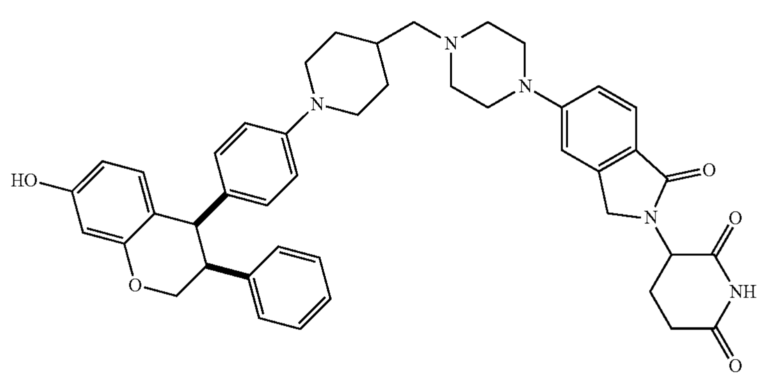 | cis-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |
| 36 | 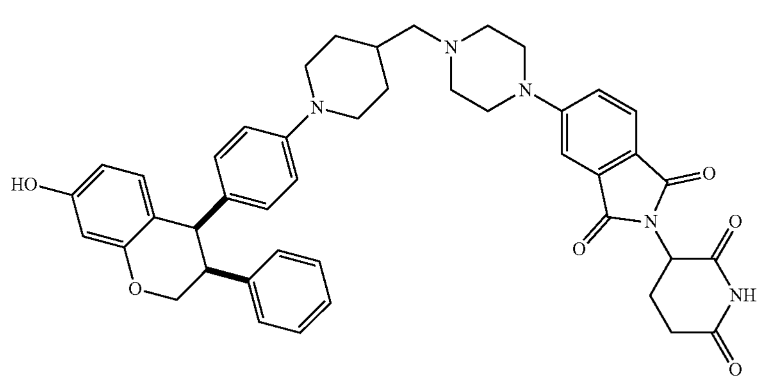 | cis-2-(2,6-dioxopiperidin-3-yl)-5-(4-((1-(4-(7-hydroxy-3-phenylchroman-4-yl)phenyl)piperidin-4-yl)methyl)piperazin-1-yl)isoindoline-1,3-dione |

TABLE 1-continued

Exemplary Compound of the Present Disclosure

| Cpd # | Chemical Structure | IUPAC Name |
|---|---|---|
| 37 | 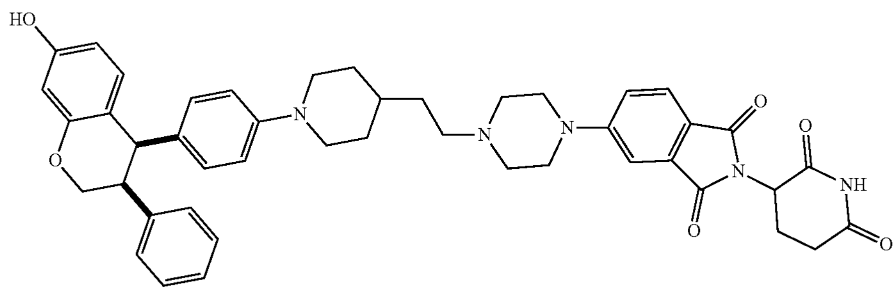 | cis-2-(2,6-dioxopiperidin-3-yl)-5-(4-(2-(1-(4-(7-hydroxy-3-phenylchroman-4-yl)phenyl)piperidin-4-yl)ethyl)piperazin-1-yl)isoindoline-1,3-dione |
| 38 | 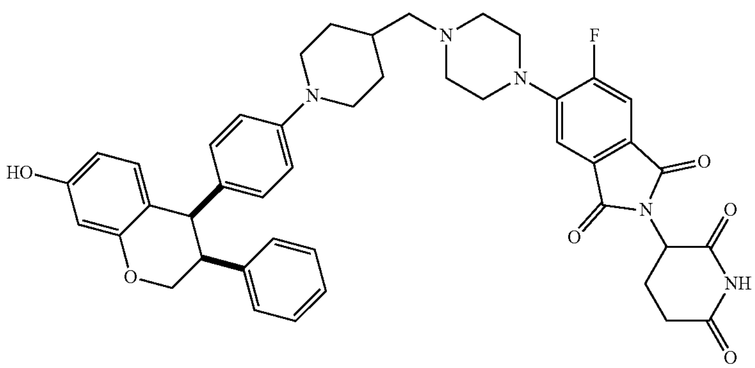 | cis-2-(2,6-dioxopiperidin-3-yl)-5-fluoro-6-(4-((1-(4-(7-hydroxy-3-phenylchroman-4-yl)phenyl)piperidin-4-yl)methyl)piperazin-1-yl)isoindoline-1,3-dione |
| 39 | 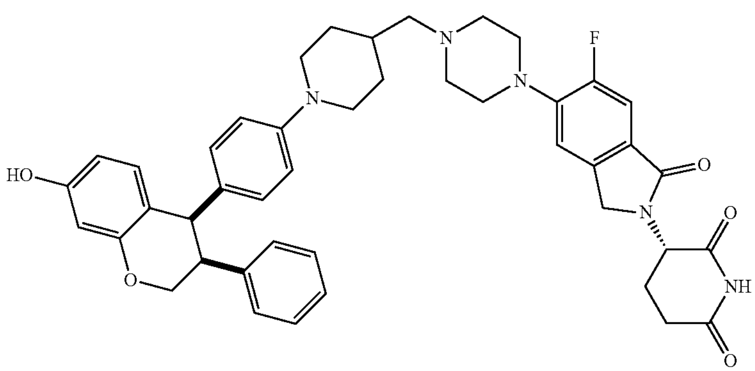 | cis-(S)-3-(6-fluoro-5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |
| 40 | 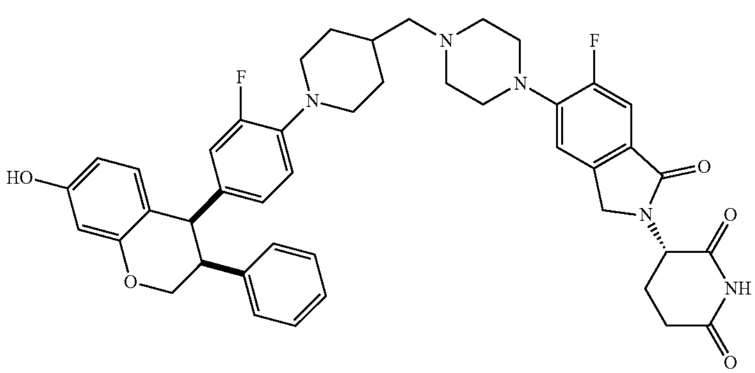 | cis-(S)-3-(6-fluoro-5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 41 | 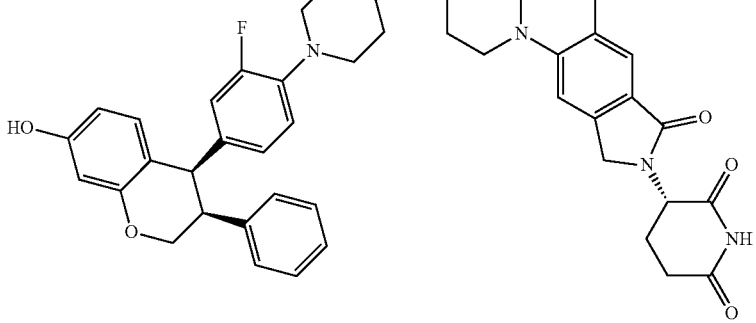 | (S)-3-(6-fluoro-5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 42 | 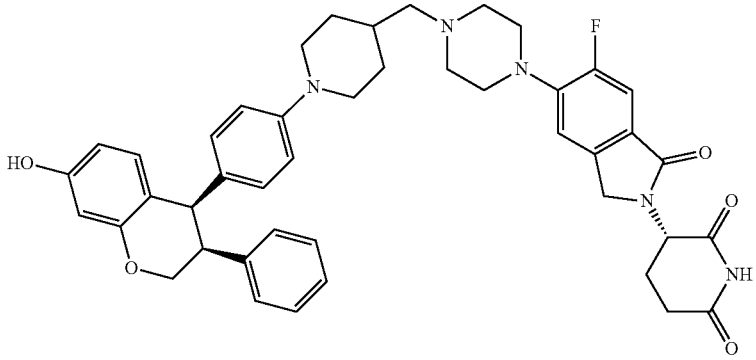 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)c(F)cc3C2=O)C(=O)N1] | (S)-3-(6-fluoro-5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 43 | 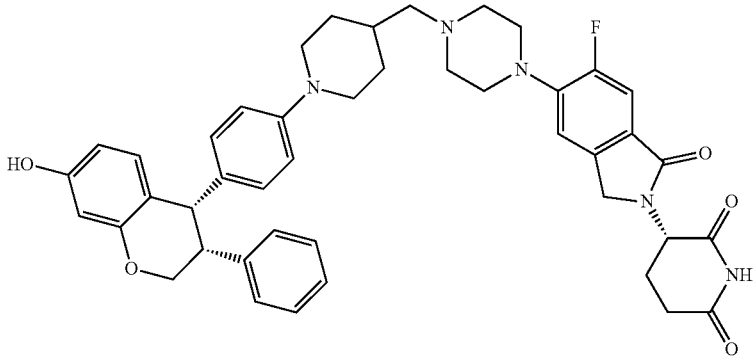 [SMILES: O=C1CC[C@H](N2Cc3cc(N4CCN(CC5CCN(c6ccc([C@H]7c8ccc(O)cc8OC[C@H]7c7ccccc7)cc6)CC5)CC4)c(F)cc3C2=O)C(=O)N1] | (S)-3-(6-fluoro-5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |
| 44 | 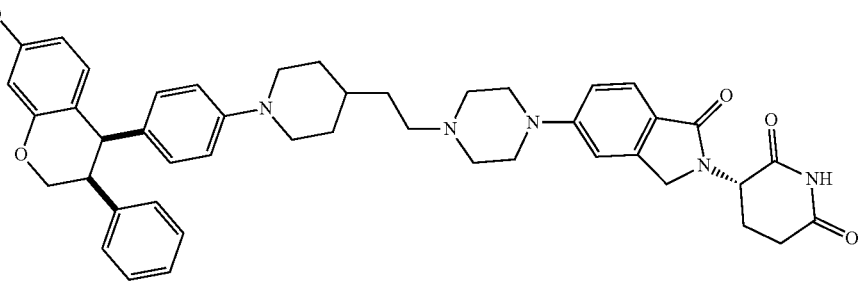 | cis-(S)-3-(5-(4-(2-(1-(4-(7-hydroxy-3-phenylchroman-4-yl)phenyl)piperidin-4-yl)ethyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 45 | 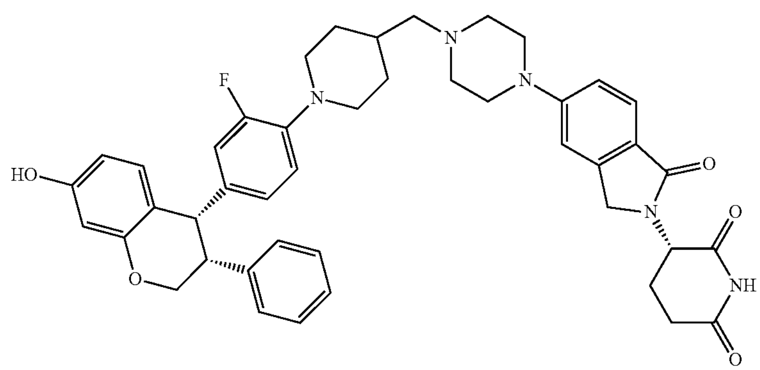 [SMILES: O=C1CC[C@H](N2Cc3cc(N4CCN(CC5CCN(c6ccc([C@H]7c8ccc(O)cc8OC[C@H]7c7ccccc7)cc6F)CC5)CC4)ccc3C2=O)C(=O)N1] | (S)-3-(5-(4-((1-(2-fluoro-4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |
| 46 | 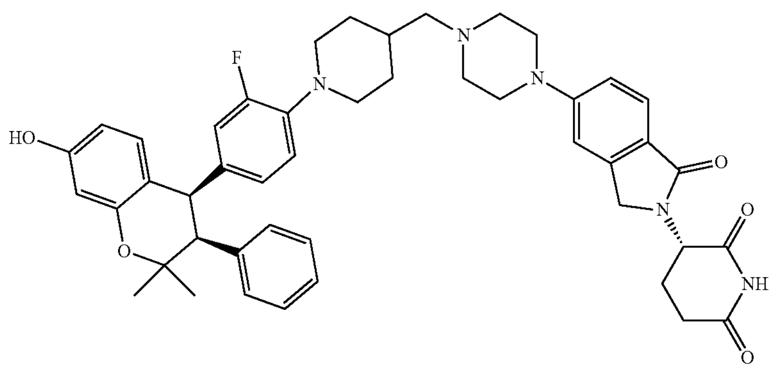 [SMILES: CC1(C)Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((3S,4R)-7-hydroxy-2,2-dimethyl-3-phenylchroman-4-yl)phenyl)piperidin-4-yl)methyl)piperazin-1-yl)-1-oxoisoindolin-2-yl)piperidine-2,6-dione |
| 47 | 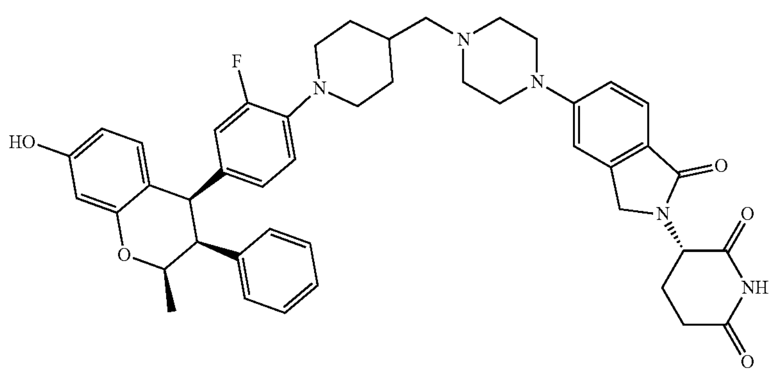 [SMILES: C[C@H]1Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((2R,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione |
| 48 | 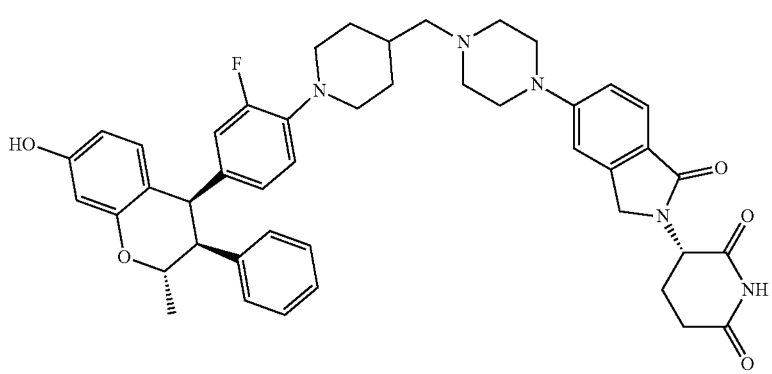 [SMILES: C[C@@H]1Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((2S,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 49 | 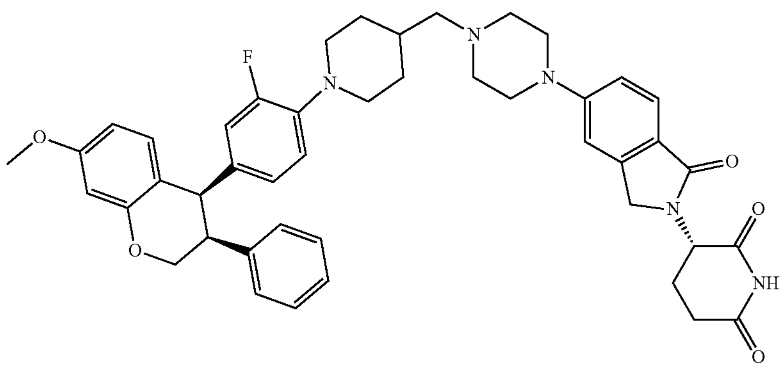 [SMILES: COc1ccc2c(c1)OC[C@H](c1ccccc1)[C@@H]2c1ccc(N2CCC(CN3CCN(c4ccc5c(c4)CN([C@H]4CCC(=O)NC4=O)C5=O)CC3)CC2)c(F)c1] | (S)-3-(5-(4-((1-(2-fluoro-4-((3S,4R)-7-methoxy-3-phenylchroman-4-yl)phenyl)piperidin-4-yl)methyl)piperazin-1-yl)-1-oxoisoindolin-2-yl)piperidine-2,6-dione |
| 50 | 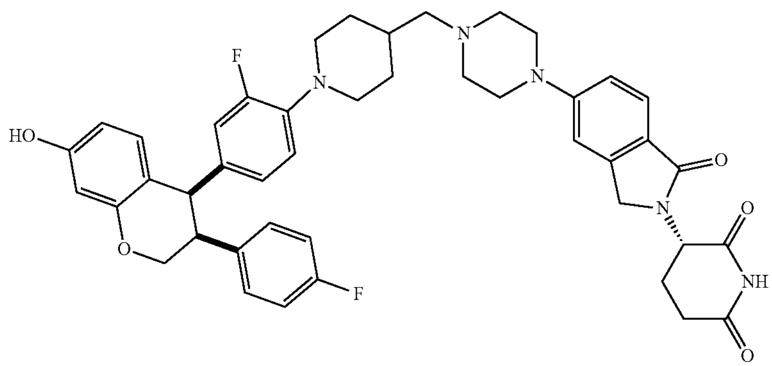 | cis-(S)-3-(5-(4-((1-(2-fluoro-4-(3-(4-fluorophenyl)-7-hydroxychroman-4-yl)phenyl)piperidin-4-yl)methyl)piperazin-1-yl)-1-oxoisoindolin-2-yl)piperidine-2,6-dione |
| 51 | 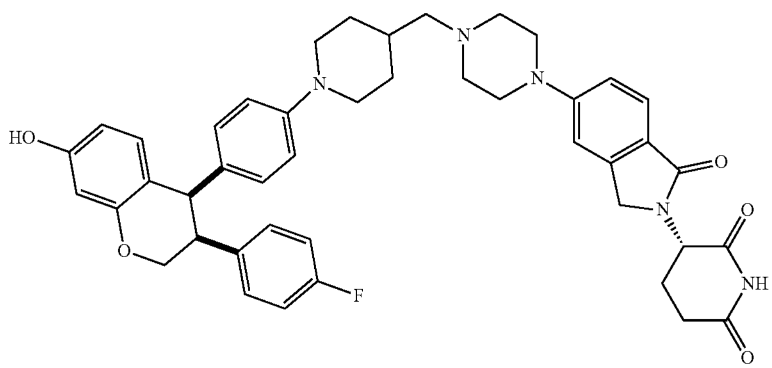 | cis-(S)-3-(5-(4-((1-(4-(3-(4-fluorophenyl)-7-hydroxychroman-4-yl)phenyl)piperidin-4-yl)methyl)piperazin-1-yl)-1-oxoisoindolin-2-yl)piperidine-2,6-dione |
| 52 | 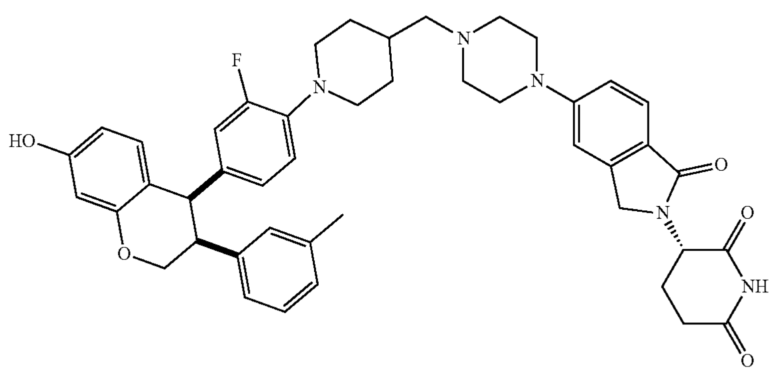 | cis-(S)-3-(5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 53 | 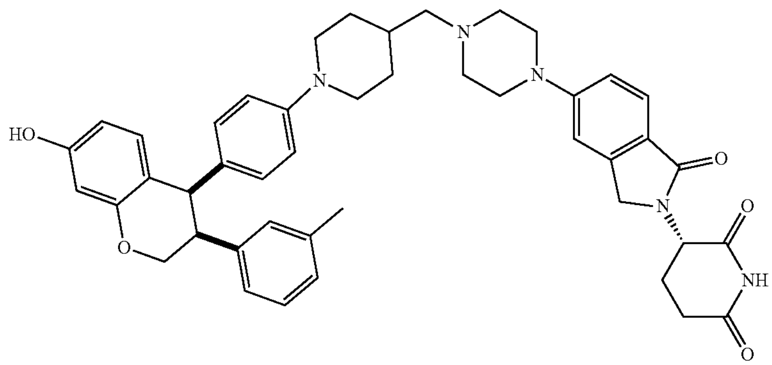 | cis-(S)-3-(5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 54 | 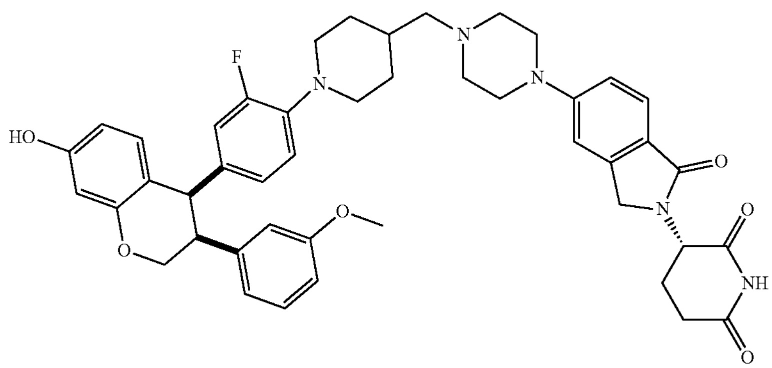 | cis-(S)-3-(5-(4-((1-(2-fluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |
| 55 | 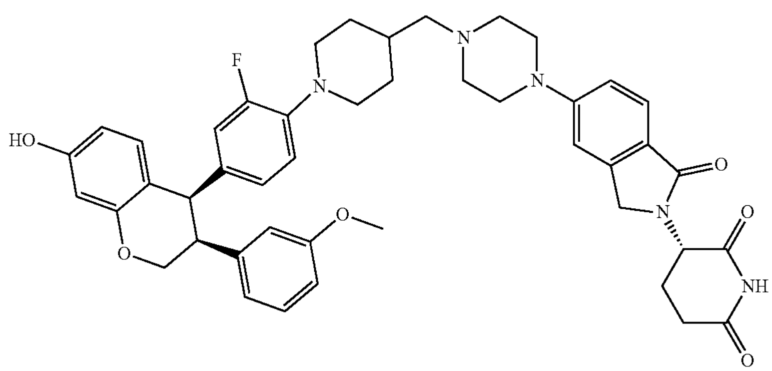 [SMILES: COc1cccc([C@H]2COc3cc(O)ccc3[C@H]2c2ccc(N3CCC(CN4CCN(c5ccc6c(c5)CN([C@H]5CCC(=O)NC5=O)C6=O)CC4)CC3)c(F)c2)c1] | (S)-3-(5-(4-((1-(2-fluoro-4-((3S,4R)-7-hydroxy-3-(3-methoxy-phenyl)chroman-4-yl)phenyl)piperidin-4-yl)methyl)piperazin-1-yl)-1-oxoisoindolin-2-yl)piperidine-2,6-dione |
| 56 | 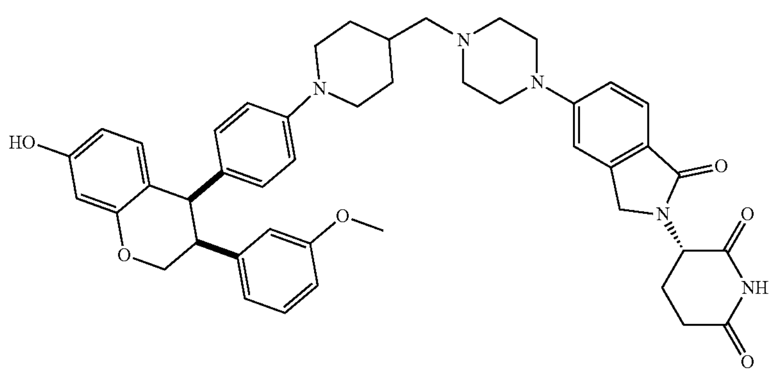 | cis-(S)-3-(5-(4-((1-(4-(7-hydroxy-3-(3-methoxy-phenyl)chroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 57 | 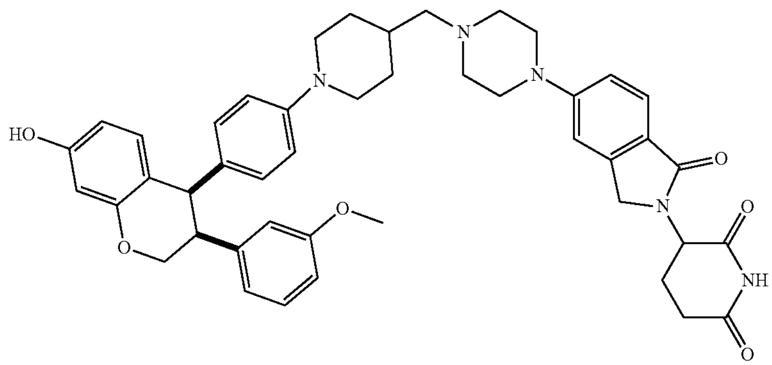 | cis-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |
| 58 | 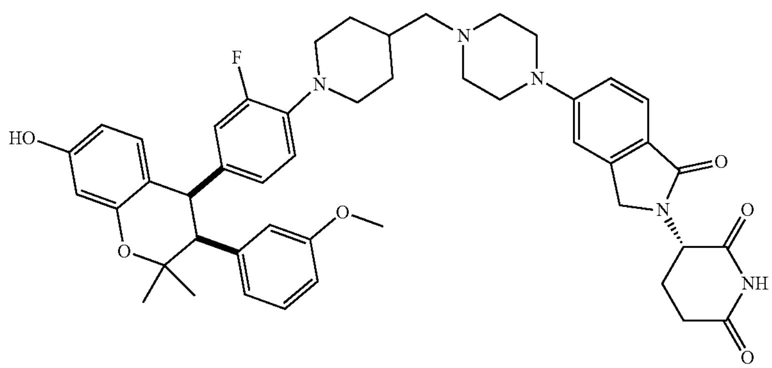 | cis-(S)-3-(5-(4-((1-(2-fluoro-4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione |
| 59 | 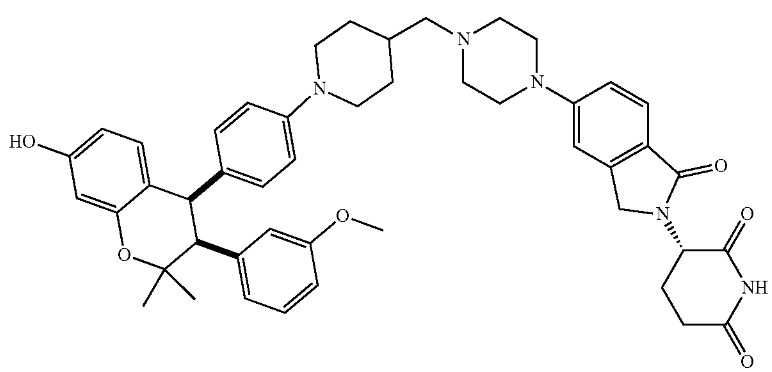 | cis-(S)-3-(5-(4-((1-(4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione |
| 60 | 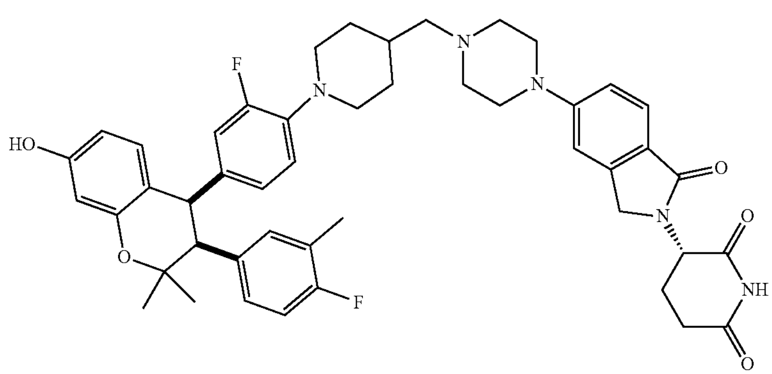 | cis-(S)-3-(5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 61 | 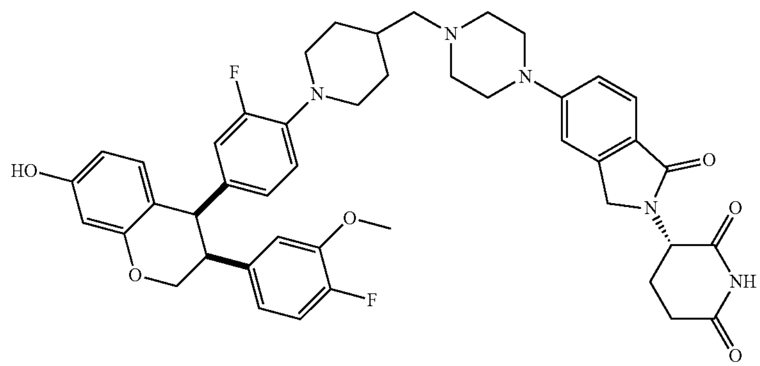 [SMILES: COc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)c(F)c2)ccc1F] | cis-(S)-3-(5-(4-((1-(2-fluoro-4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |
| 62 | 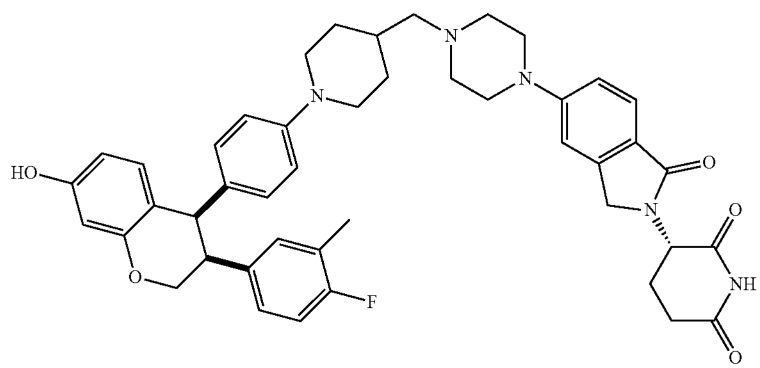 [SMILES: Cc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)cc2)ccc1F] | cis-(S)-3-(5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |
| 63 | 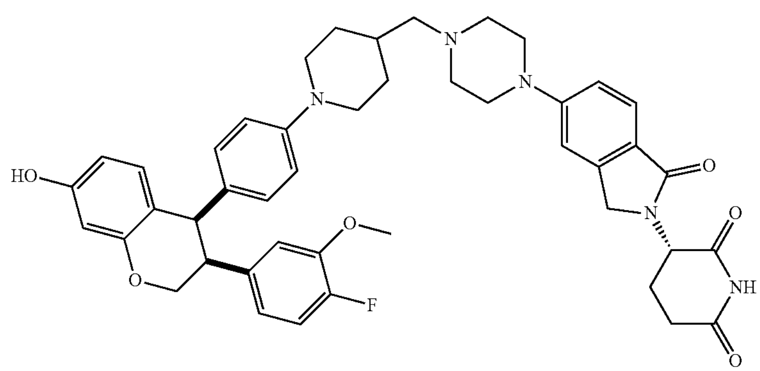 | cis-(S)-3-(5-(4-((1-(4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |
| 64 | 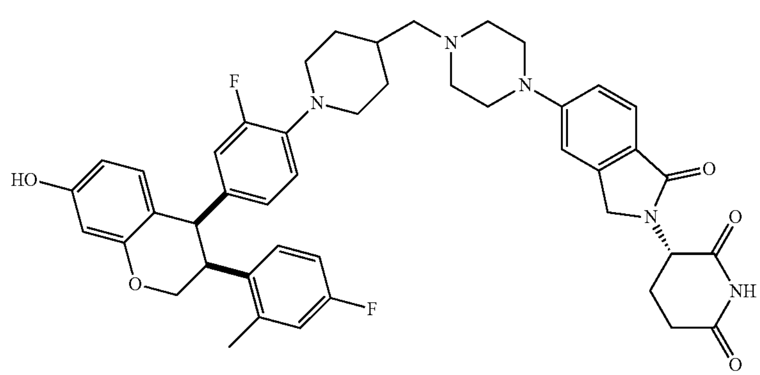 [SMILES: Cc1cc(F)ccc1[C@H]1COc2cc(O)ccc2[C@H]1c1ccc(N2CCC(CN3CCN(c4ccc5c(c4)CN([C@H]4CCC(=O)NC4=O)C5=O)CC3)CC2)c(F)c1] | cis-(S)-3-(5-(4-((1-(2-fluoro-4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 65 | 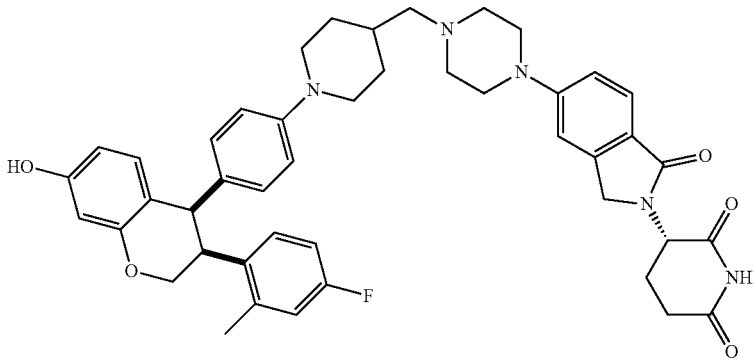 | cis-(S)-3-(5-(4-((1-(4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione |
| 66 | 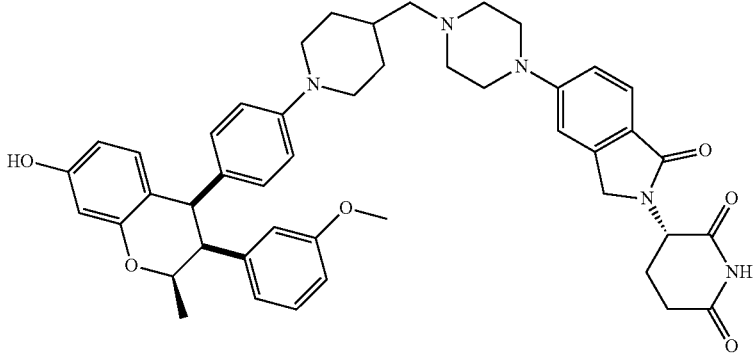 [SMILES: COc1cccc([C@@H]2[C@H](c3ccc(N4CCC(CN5CCN(c6ccc7c(c6)CN([C@H]6CCC(=O)NC6=O)C7=O)CC5)CC4)cc3)c3ccc(O)cc3O[C@@H]2C)c1] | cis-(S)-3-(5-(4-((1-(4-((2R)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione |
| 67 | 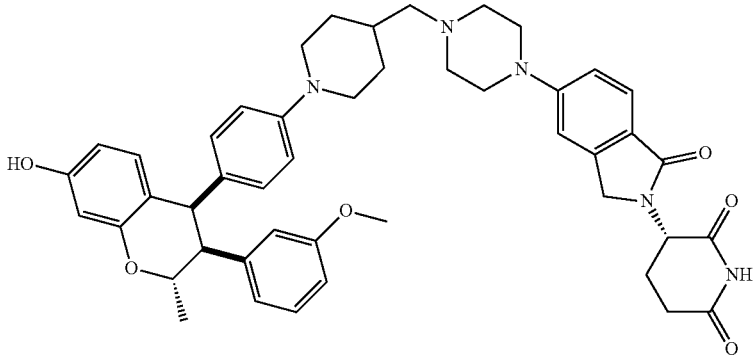 [SMILES: COc1cccc([C@@H]2[C@H](c3ccc(N4CCC(CN5CCN(c6ccc7c(c6)CN([C@H]6CCC(=O)NC6=O)C7=O)CC5)CC4)cc3)c3ccc(O)cc3O[C@H]2C)c1] | cis-(S)-3-(5-(4-((1-(4-((2S)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione |
| 68 | 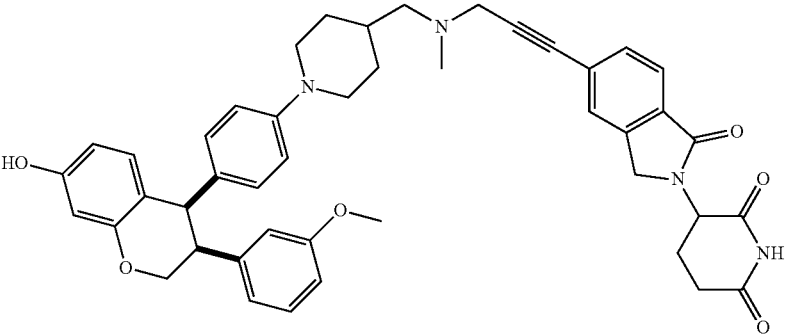 | cis-3-(5-(3-(((1-(4-(7-hydroxy-3-(3-methoxy-phenyl)chroman-4-yl)phenyl)piperidin-4-yl)methyl)(methyl)amino)prop-1-yn-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 69 | 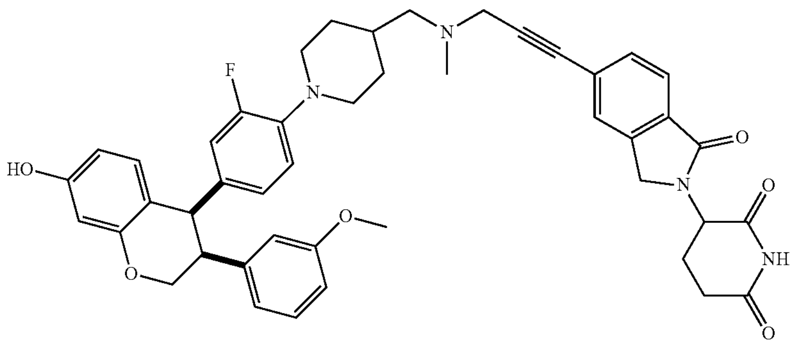 [SMILES: COc1cccc([C@H]2COc3cc(O)ccc3[C@H]2c2ccc(N3CCC(CN(C)CC#Cc4ccc5c(c4)CN(C4CCC(=O)NC4=O)C5=O)CC3)c(F)c2)c1] | cis-3-(5-(3-(((1-(2-fluoro-4-(7-hydroxy-3-(3-methoxy-phenyl)chroman-4-yl)phenyl)piperidin-4-yl)methyl)(methyl)amino)prop-1-yn-1-yl)-1-oxoisoindolin-2-yl)piperidine-2,6-dione |
| 70 | 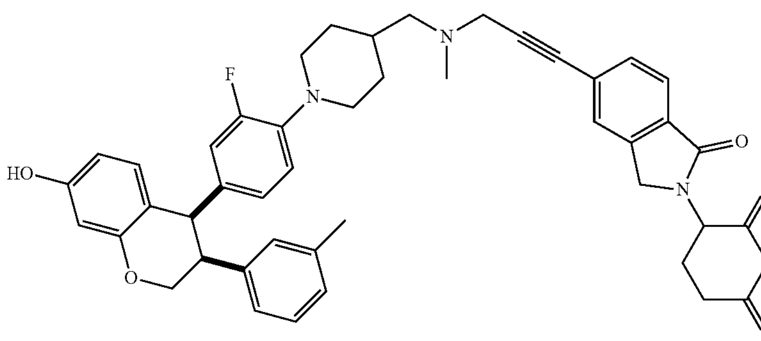 | cis-3-(5-(3-(((1-(2-fluoro-4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione |
| 71 | 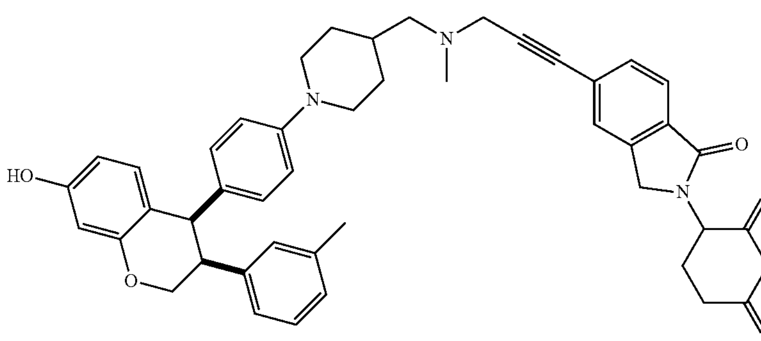 | cis-3-(5-(3-(((1-(4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione |
| 72 | 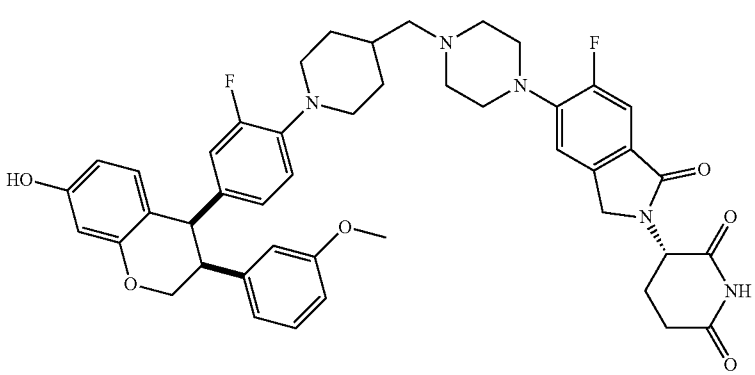 | cis-(S)-3-(6-fluoro-5-(4-((1-(2-fluoro-4-(7-hydroxy-3-(3-methoxy-phenyl)chroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 73 | 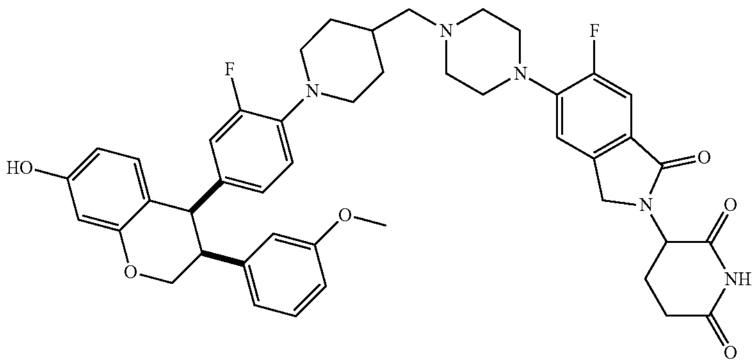 | cis-2-(2,6-dioxo-piperidin-3-yl)-5-fluoro-6-(4-((1-(2-fluoro-4-(7-hydroxy-3-(3-methoxy-phenyl)chroman-4-yl)phenyl)piperidin-4-yl)methyl)piperazin-1-yl)isoindoline-1,3-dione |
| 74 | 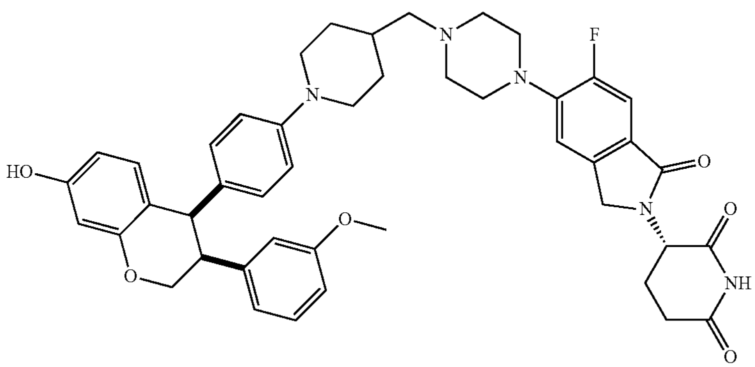 [SMILES: COc1cccc([C@H]2COc3cc(O)ccc3[C@H]2c2ccc(N3CCC(CN4CCN(c5cc6c(cc5F)C(=O)N(C5CCC(=O)NC5=O)C6)CC4)CC3)cc2)c1] | cis-(S)-3-(6-fluoro-5-(4-((1-(4-(7-hydroxy-3-(3-methoxy-phenyl)chroman-4-yl)phenyl)piperidin-4-yl)methyl)piperazin-1-yl)-1-oxoisoindolin-2-yl)piperidine-2,6-dione |
| 75 | 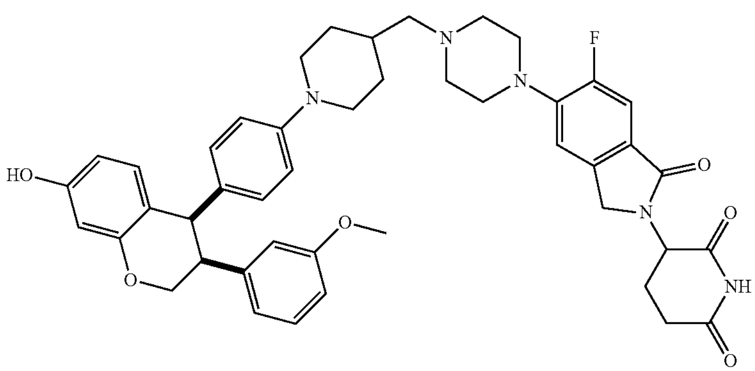 | cis-2-(2,6-dioxopiperidin-3-yl)-5-fluoro-6-(4-((1-(4-(7-hydroxy-3-(3-methoxy-phenyl)chroman-4-yl)phenyl)piperidin-4-yl)methyl)piperazin-1-yl)isoindoline-1,3-dione |
| 76 | 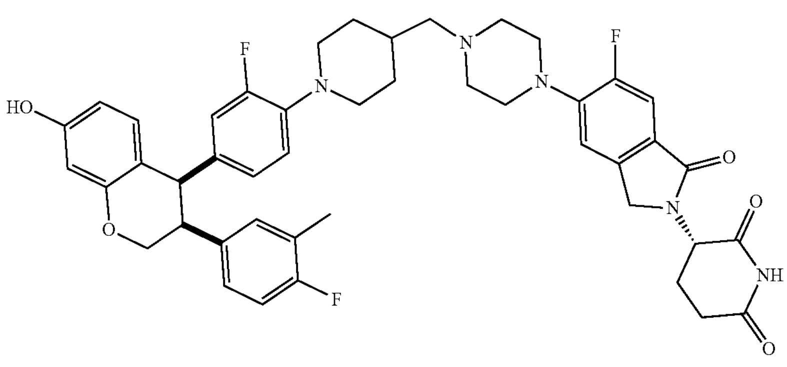 | cis-(S)-3-(6-fluoro-5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 77 | 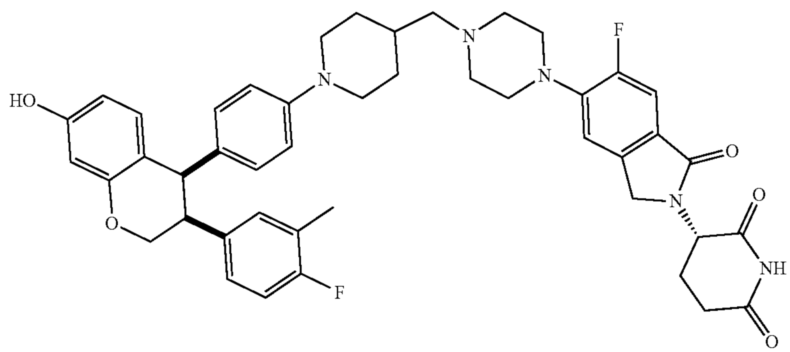 | cis-(S)-3-(6-fluoro-5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |
| 78 | 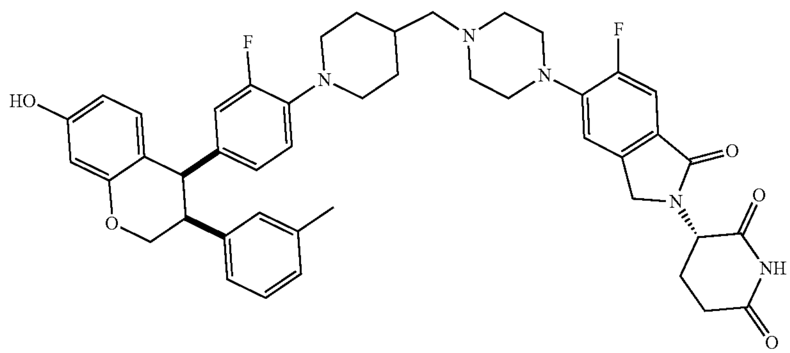 | cis-(S)-3-(6-fluoro-5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 79 | 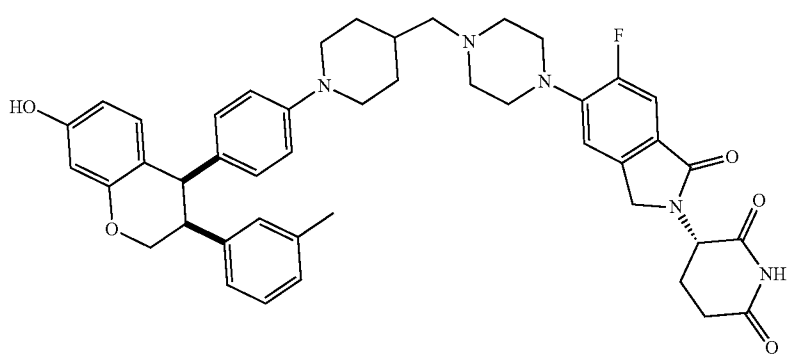 | cis-(S)-3-(6-fluoro-5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 80 | 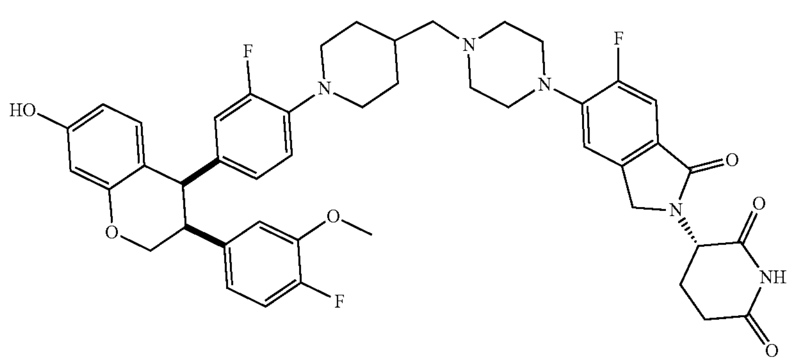 | cis-(S)-3-(6-fluoro-5-(4-((1-(2-fluoro-4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 81 | 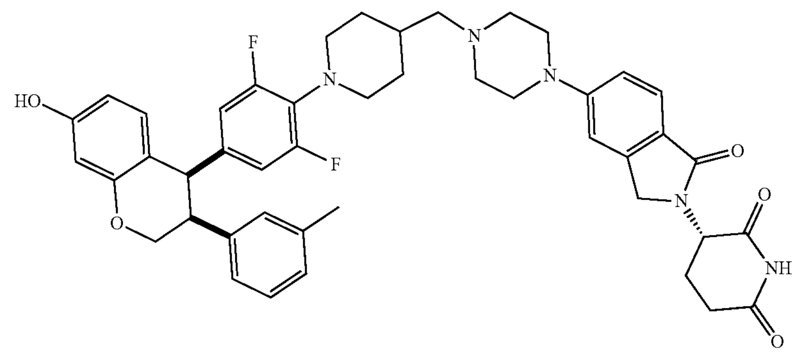 | cis-(S)-3-(5-(4-((1-(2,6-difluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 82 | 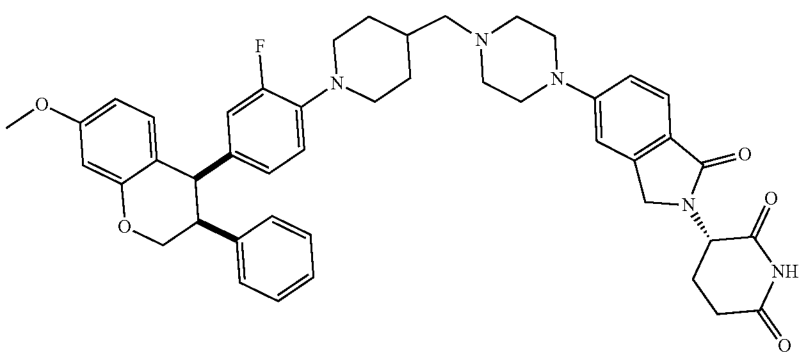 | cis-(S)-3-(5-(4-((1-(2-fluoro-4-(7-methoxy-3-phenylchroman-4-yl)phenyl)piperidin-4-yl)methyl)piperazin-1-yl)-1-oxoisoindolin-2-yl)piperidine-2,6-dione |
| 83 | 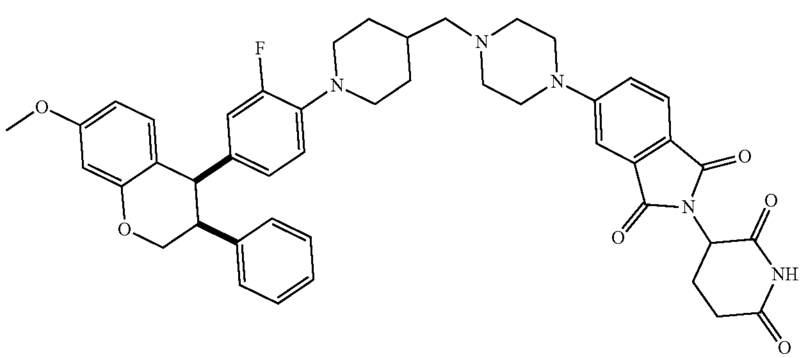 | cis-2-(2,6-dioxo-piperidin-3-yl)-5-(4-((1-(2-fluoro-4-(7-methoxy-3-phenylchroman-4-yl)phenyl)piperidin-4-yl)methyl)piperazin-1-yl)isoindoline-1,3-dione |
| 84 | 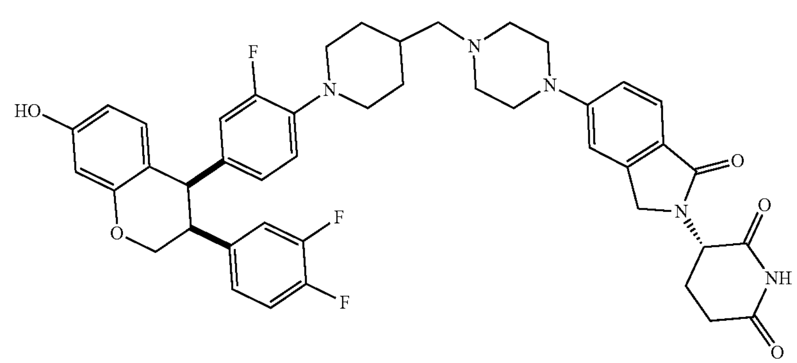 | cis-(S)-3-(5-(4-((1-(4-(3-(3,4-difluorophenyl)-7-hydroxychroman-4-yl)-2-fluoro-phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 85 | 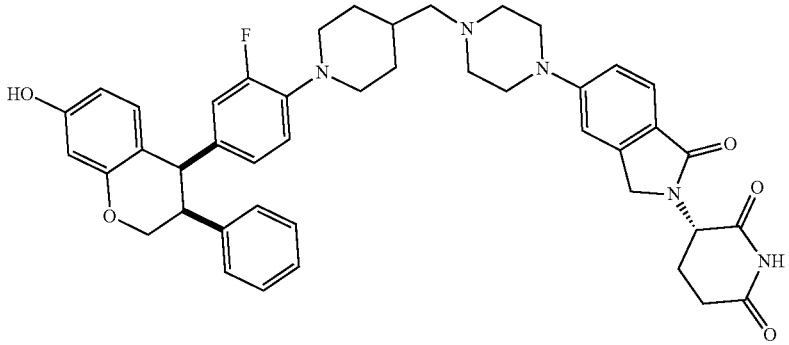 | cis-(S)-3-(5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione |
| 86 | 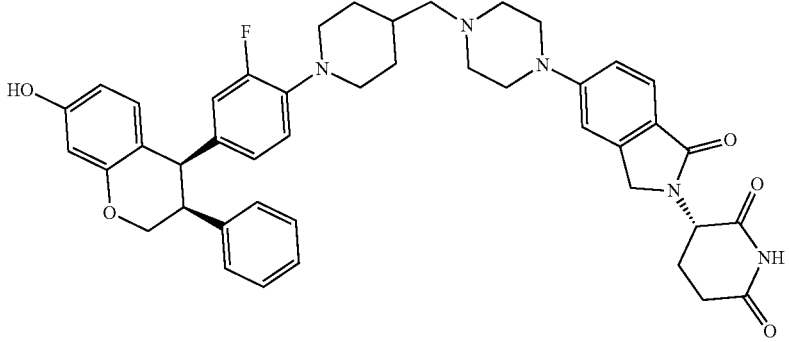 [SMILES: O=C1CC[C@H](N2Cc3cc(N4CCN(CC5CCN(c6ccc([C@@H]7c8ccc(O)cc8OC[C@@H]7c7ccccc7)cc6F)CC5)CC4)ccc3C2=O)C(=O)N1] | (S)-3-(5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 87 | 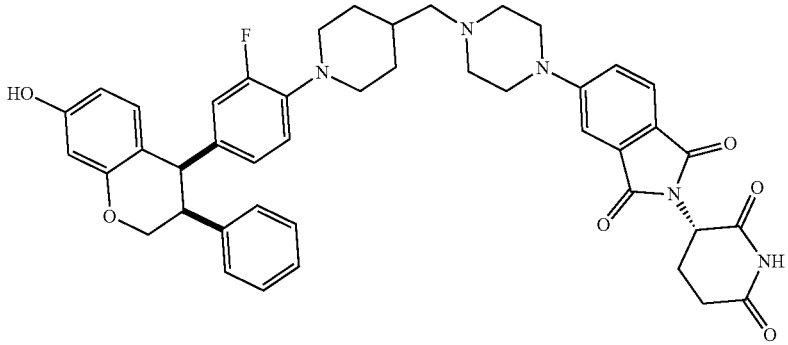 | cis-2-(2,6-dioxo-piperidin-3-yl)-5-(4-((1-(2-fluoro-4-(7-hydroxy-3-phenylchroman-4-yl)phenyl)piperidin-4-yl)methyl)piperazin-1-yl)isoindoline-1,3-dione |
| 88 | 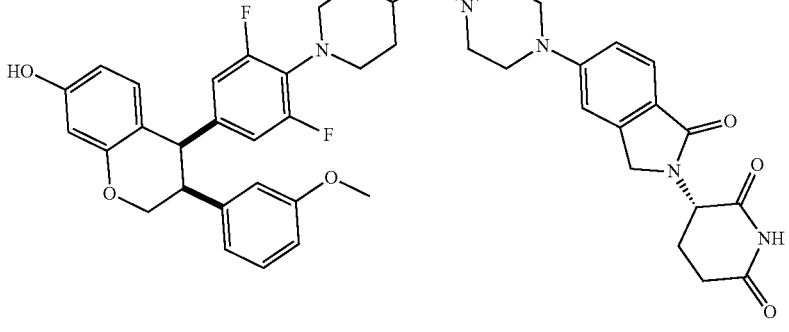 | cis-(S)-3-(5-(4-((1-(2,6-difluoro-4-(7-hydroxy-3-(3-methoxy-phenyl)chroman-4-yl)phenyl)piperidin-4-yl)methyl)piperazin-1-yl)-1-oxoisoindolin-2-yl)piperidine-2,6-dione |

TABLE 1-continued

Exemplary Compound of the Present Disclosure

| Cpd # | Chemical Structure | IUPAC Name |
|---|---|---|
| 89 | | cis-(S)-3-(5-(4-((1-(4-(7-hydroxy-3-(4-methoxy-phenyl)chroman-4-yl)phenyl)piperidin-4-yl)methyl)piperazin-1-yl)-1-oxoisoindolin-2-yl)piperidine-2,6-dione |
| 90 | | cis-(S)-3-(6-fluoro-5-(4-((1-(4-(7-hydroxy-3-(4-methoxy-phenyl)chroman-4-yl)phenyl)piperidin-4-yl)methyl)piperazin-1-yl)-1-oxoisoindolin-2-yl)piperidine-2,6-dione |

Pharmaceutical Compositions

Pharmaceutical compositions of the present disclosure comprise at least one compound of Formula (I), or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I), or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I), or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 2

Equivalent Surface Area Dosage Factors.

| From | Mouse (20 g) | Rat (150 g) | Monkey (3.5 kg) | Dog (8 kg) | Human (60 kg) |
|---|---|---|---|---|---|
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (I), or a tautomer, stereoisomer, pharmaceutically acceptable salt or hydrate thereof, is administered to treat cancer in a subject in need thereof. In some embodiments, the cancer is chosen from breast cancer, lung cancer, ovarian cancer, endometrial cancer, prostate cancer, and esophageal cancer. In some embodiments, the cancer is breast cancer. In some embodiments, the cancer is lung cancer. In some embodiments, the cancer is ovarian cancer. In some embodiments, the cancer is endometrial cancer. In some embodiments, the cancer is prostate cancer. In some embodiments, the cancer is esophageal cancer. In some embodiments, the cancer is positive for ERα. In some embodiments, a compound of Formula (I), or a tautomer, stereoisomer, pharmaceutically acceptable salt or hydrate thereof, is administered as a pharmaceutical composition. In some embodiments, the subject has been previously treated with tamoxifen.

In some embodiments, provided herein is a use of a compound of Formula (I), or a tautomer, stereoisomer, pharmaceutically acceptable salt or hydrate thereof, in a therapeutic treatment. In some embodiments, the therapeutic treatment is for the treatment of breast cancer, lung cancer, ovarian cancer, endometrial cancer, prostate cancer, and esophageal cancer. In some embodiments, the therapeutic treatment is for the treatment of breast cancer. In some embodiments, the therapeutic treatment is for lung cancer. In some embodiments, the therapeutic treatment is for the treatment of ovarian cancer. In some embodiments, the therapeutic treatment is for the treatment of endometrial cancer. In some embodiments, the therapeutic treatment is for the treatment of prostate cancer. In some embodiments, the therapeutic treatment is for the treatment of esophageal cancer. In some embodiments, the therapeutic treatment is for the treatment of estrogen-related diseases and conditions. In some embodiments, the therapeutic treatment is for the treatment of infertility. In some embodiments, the therapeutic treatment is for the treatment of ovulatory dysfunction. In some embodiments, the therapeutic treatment is for the treatment of postmenopausal osteoporosis. In some embodiments, the therapeutic treatment is for the treatment of estrogen-related gynecomastia. In some embodiments, the therapeutic treatment is for the treatment of dyspareunia due to menopause. In some embodiments, the therapeutic treatment is for the treatment of retroperitoneal fibrosis. In some embodiments, the therapeutic treatment is for the treatment of idiopathic sclerosing mesenteritis.

In some embodiments, provided herein is a use of a compound of Formula (I), or a tautomer, stereoisomer, pharmaceutically acceptable salt or hydrate thereof, in the preparation of a medicament. In some embodiments, provided herein is a method of inhibiting cell growth comprising contacting a cell with a compound of Formula (I), or a tautomer, stereoisomer, pharmaceutically acceptable salt or hydrate thereof. In some embodiments, the cell may express ERα.

In one embodiment, a compound of Formula (I), or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula (I), or a tautomer, stereoisomer, pharmaceutically acceptable salt or hydrate thereof, may be administered in combination with a hormone or hormonal analog. In some embodiments, a compound of Formula (I), or a tautomer, stereoisomer, pharmaceutically acceptable salt or hydrate thereof, may be administered in combination with a signal transduction pathway inhibitor. In some embodiments, a compound of Formula (I), or a tautomer, stereoisomer, pharmaceutically acceptable salt or hydrate thereof, may be administered in combination with an antimetabolite neoplastic agent. In some embodiments, a compound of Formula (I), or a tautomer, stereoisomer, pharmaceutically acceptable salt or hydrate thereof, may be administered in combination with a topoisomerase I inhibitor. In some embodiments, a compound of Formula (I), or a tautomer, stereoisomer, pharmaceutically acceptable salt or hydrate thereof, may be administered in combination with a topoisomerase II inhibitor. In some embodiments, a compound of Formula (I), or a tautomer, stereoisomer, pharmaceutically acceptable salt or hydrate thereof, may be administered in combination with an aromatase inhibitor. In some embodiments, a compound of Formula (I), or a tautomer, stereoisomer, pharmaceutically acceptable salt or hydrate thereof, may be administered in combination with one or more anti-cancer agents.

In some embodiments, a compound of Formula (I), or a tautomer, stereoisomer, pharmaceutically acceptable salt or hydrate thereof, may be administered in combination with an anti-cancer agent, wherein the anti-cancer agent is tamoxifen. In some embodiments, a compound of Formula (I), or a tautomer, stereoisomer, pharmaceutically acceptable salt or hydrate thereof, may be administered in combination with an anti-cancer agent, wherein the anti-cancer agent is fulvestrant.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, N.J.:

J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, 3$^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

The following abbreviations have the definitions set forth below:
1. BINAP: 2,2'-bis(diphenylphosphino)-1,1'-binaphthyl
2. CbzCl: benzyloxycarbonyl chloride
3. DCE: 1,2-dichloroethane
4. DCM: dichloromethane
5. DIEA or DIPEA: N,N-diisopropylethylamine
6. DMEM: Dulbecco's Modification of Eagle's Medium
7. DMSO: dimethylsulfoxide
8. DMF: N,N-dimethylformamide
9. EDCI: 1-Ethyl-3-(3-dimethylaminopropyl)carbodiimide
10. ESI-TOF: electrospray ionization time-of-flight mass spectrometry
11. EtOAc: ethyl acetate
12. FBS: fetal bovine serum
13. HOAt: 1-hydroxy-7-azabenzotriazole
14. HPLC: high pressure liquid chromatography
15. HRMS: high resolution mass spectrometry
16. IBX: 2-iodoxybenzoic acid
17. MeOH: methanol
18. MCF-7: Michigan Cancer Foundation-7 breast cancer cell line
19. MTBE: methyl tert-butyl ether
20. NBS: N-bromosuccinimide
21. NMR: nuclear magnetic resonance
22. NCS: N-chlorosuccinimide
23. Pd(dppf)Cl2: bis(diphenylphosphino)ferrocenepalladiumdichloride
24. RPMI: Roswell Park Memorial Institute medium
25. SDS: sodium dodecyl sulfate
26. SFC: Supercritical fluid chromatography
27. TBAB: tetrabutylammonium bromide
28. TBST: tris-buffered saline and Tween 20
29. TEMPO: 2,2,6,6-Tetramethyl-1-piperidinyloxy
30. p-TSA or TsOH p-toluenesulfonic acid
31. THF: tetrahydrofuran Example 1. Synthesis of Compounds of the Present Disclosure Chemistry General Procedures.

HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker spectrometer with 600 MHz or 400 MHz for proton ($^1$H NMR) and 150 MHz for carbon ($^{13}$C NMR); chemical shifts are reported in (5). Preparative HPLC was performed on Agilent Prep 1200 series with UV detector set to 254 nm and 220 nm. Samples were injected onto a Phenomenex Luna 75×30 mm, 5 μm, C18 column at room temperature. The flow rate was 40 mL/min. A linear gradient was used with 10% (or 50%) of MeOH (A) in H$_2$O (with 0.1% TFA) (B) to 100% of MeOH (A). HPLC was used to establish the purity of target compounds. All final compounds were determined to be >95% purity when analyzed according to the HPLC methods described above.

Compounds with structures of Formula (I) claimed in this application can be prepared by connecting two ligands through a linker. In general, the claimed molecules can be approached in a stepwise or modular fashion. The following schemes represent the general methods used in preparing these compounds. However, the synthesis of Formula (I) is not limited to these representative methods, as they can also be prepared by those skilled in the art of synthetic chemistry.

Scheme 1: Synthesis of Compound 1
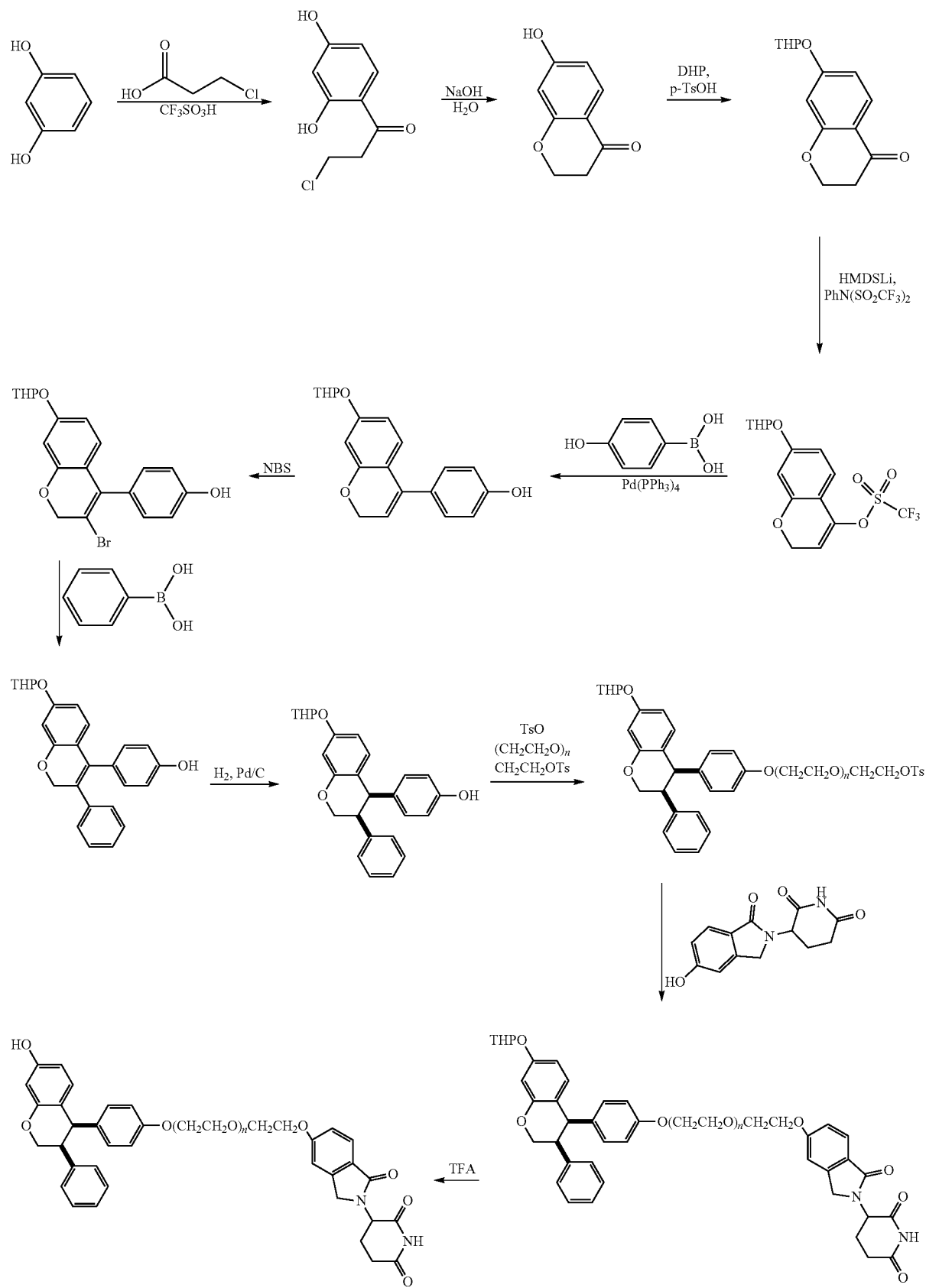

Scheme 2: Synthesis of Compound 2
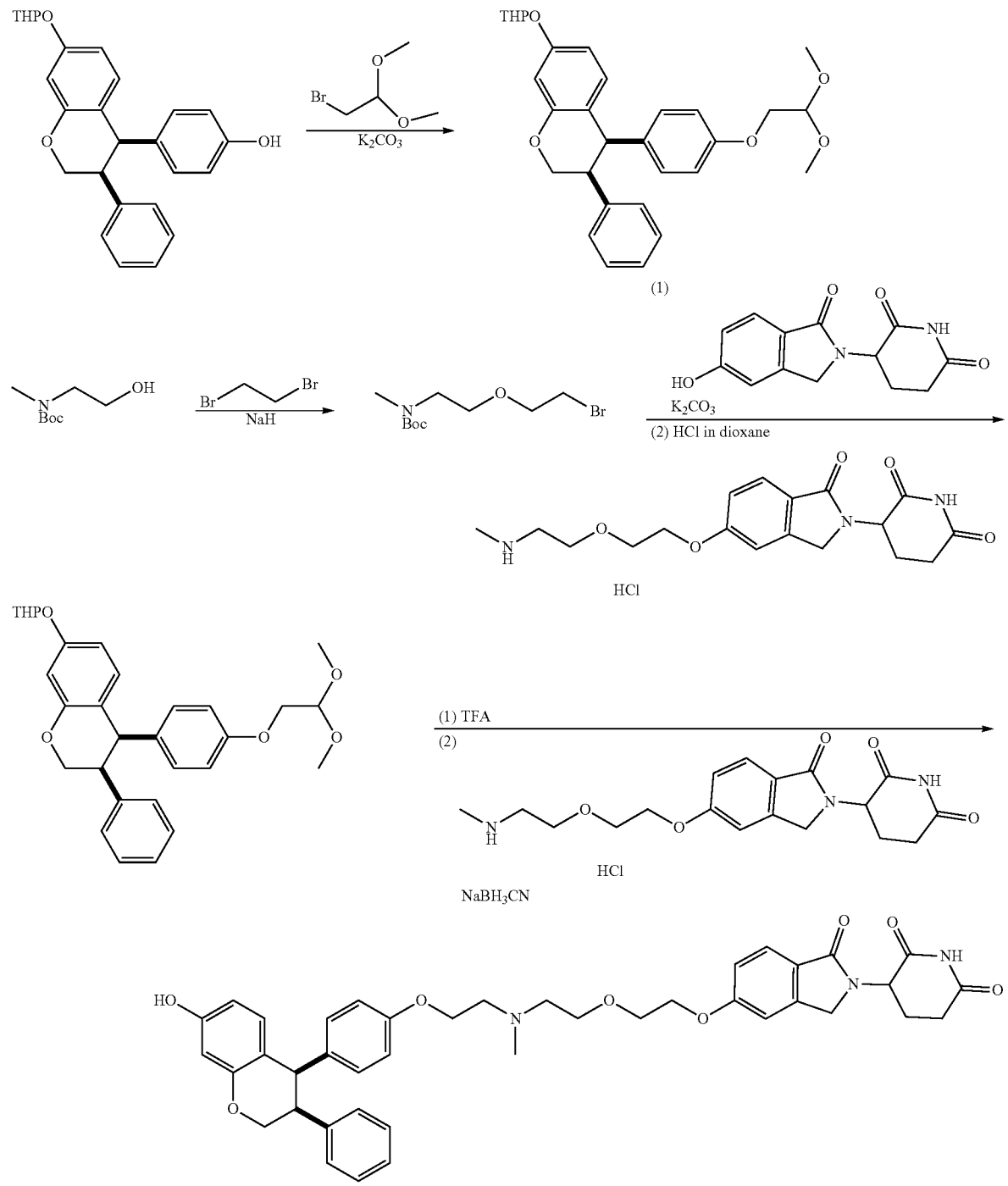
Scheme 3: Synthesis of Compound 3
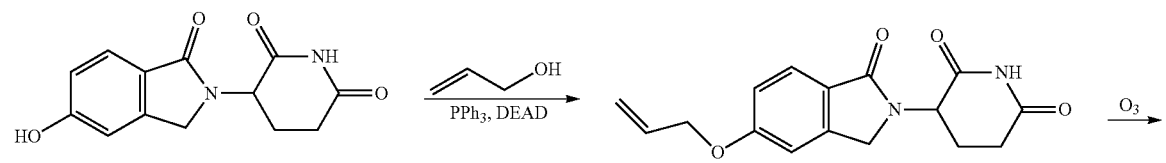

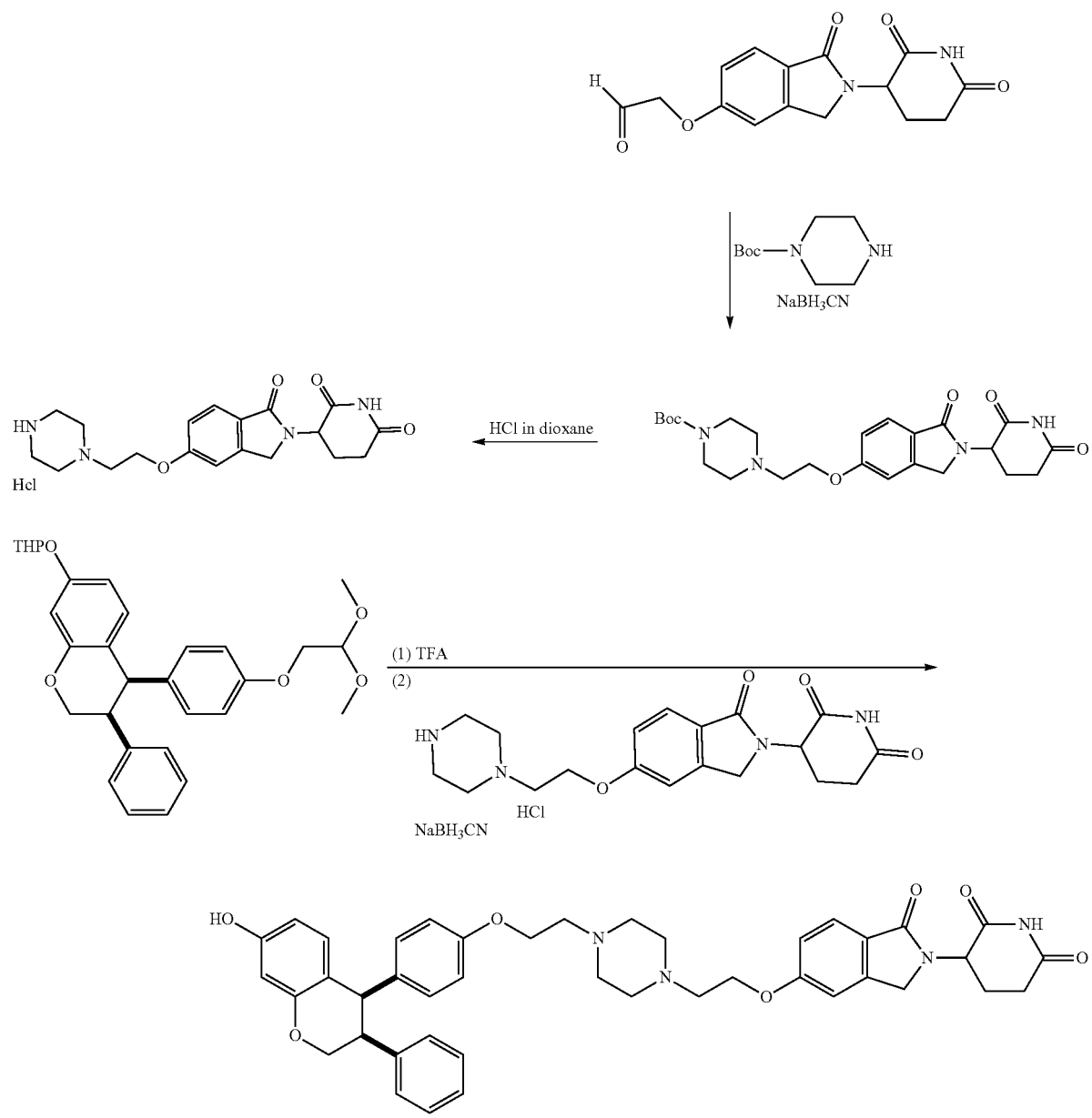
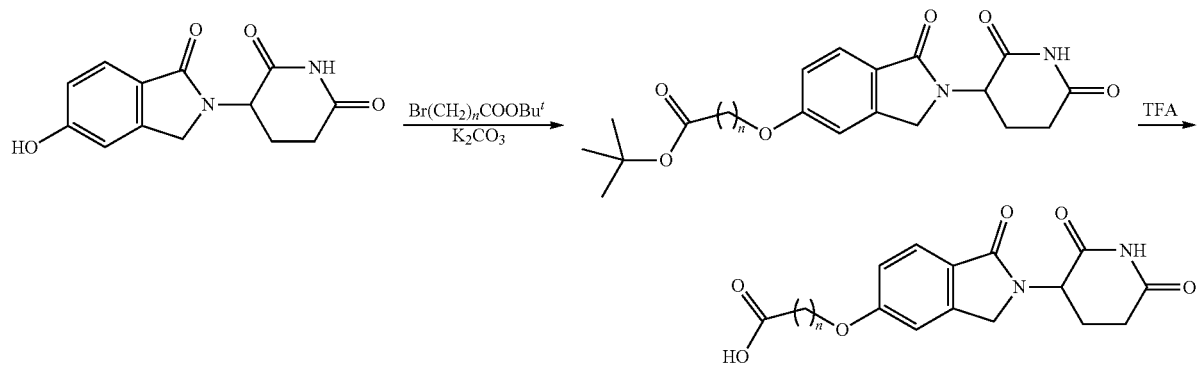
Scheme 4: Synthesis of Compound 4

-continued
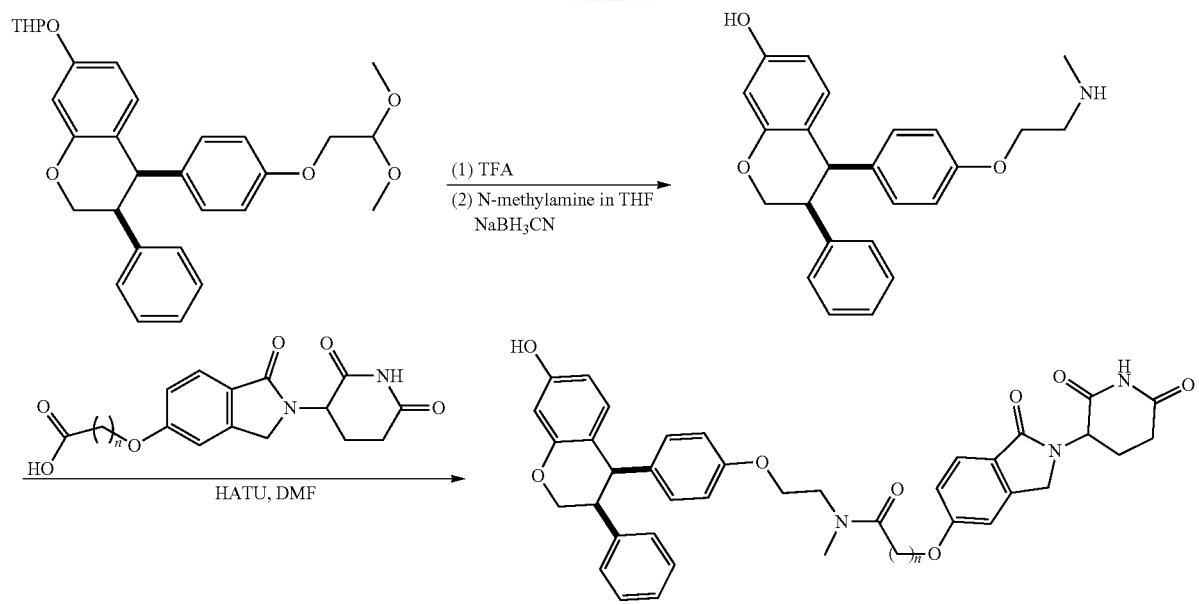
Scheme 5: Synthesis of Compound 5-8
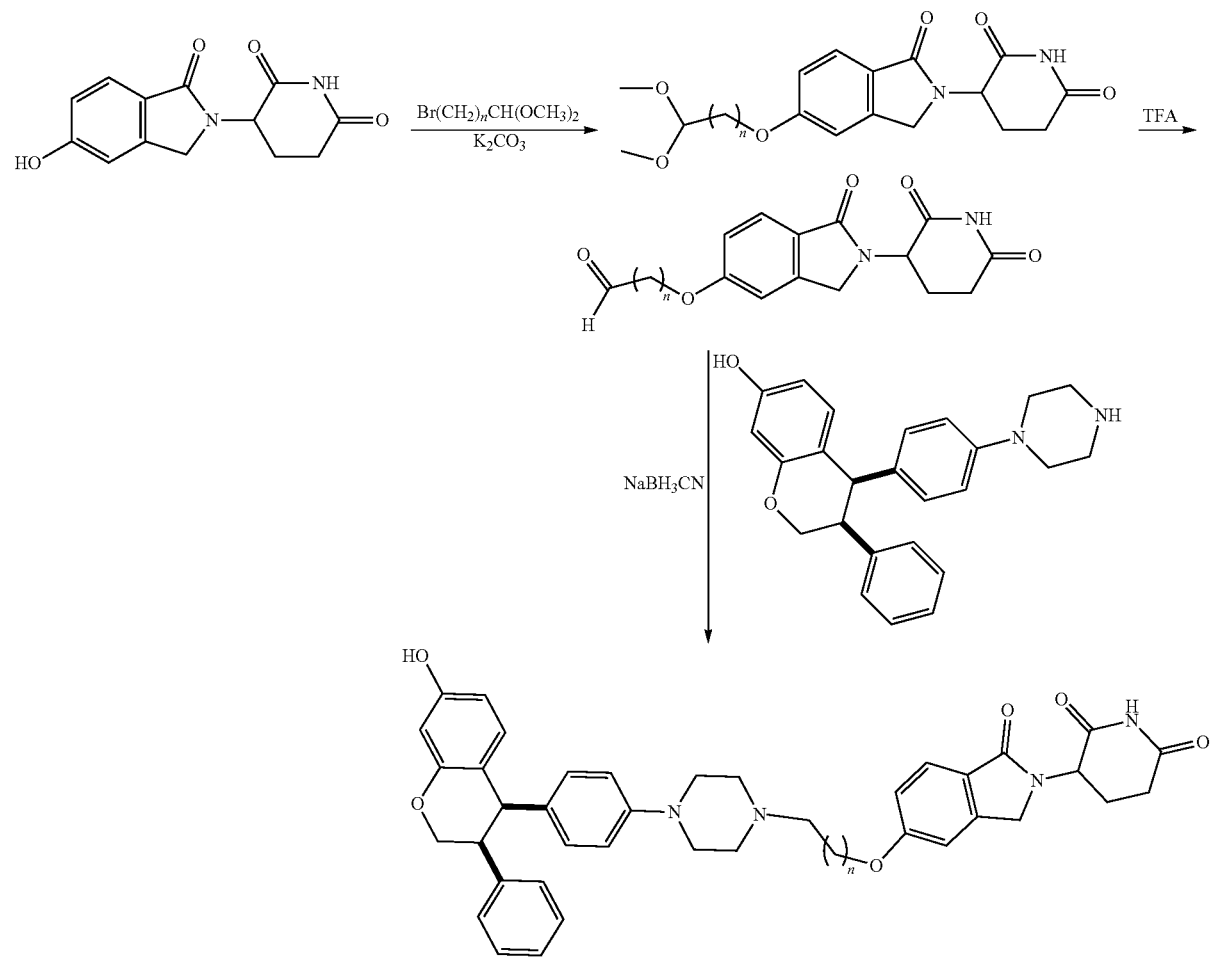
Compound 5

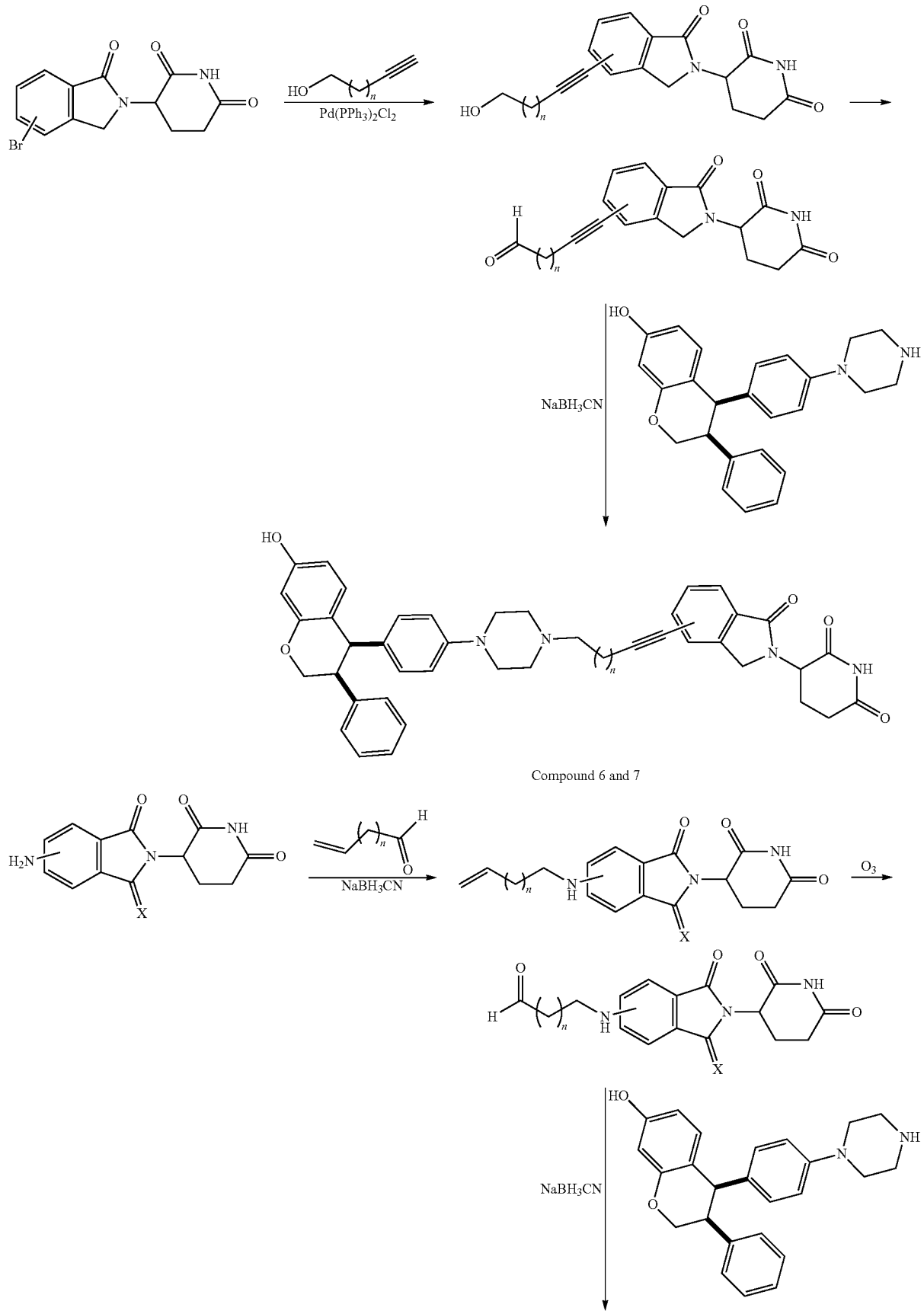

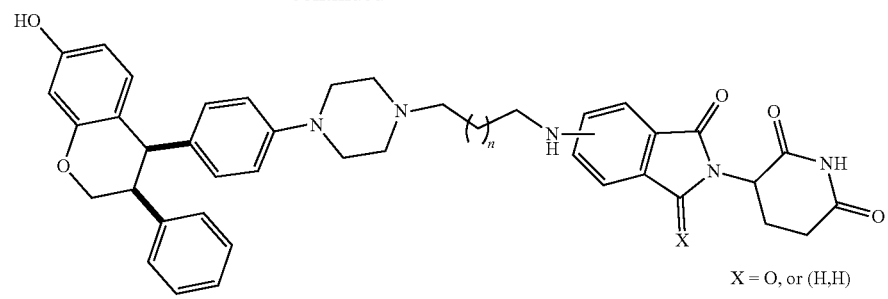
Compound 8
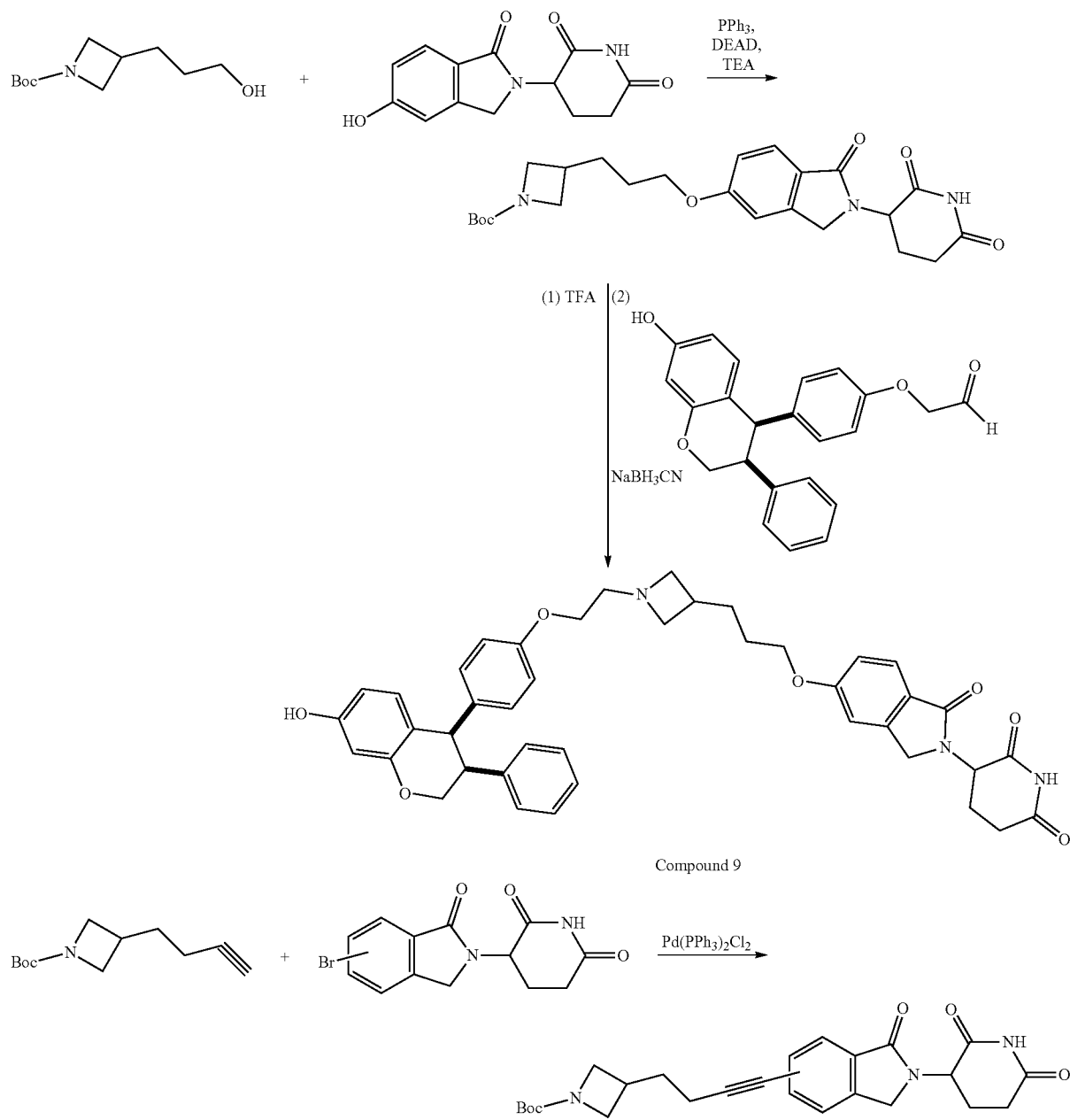
Scheme 6: Synthesis of Compounds 9-11

-continued
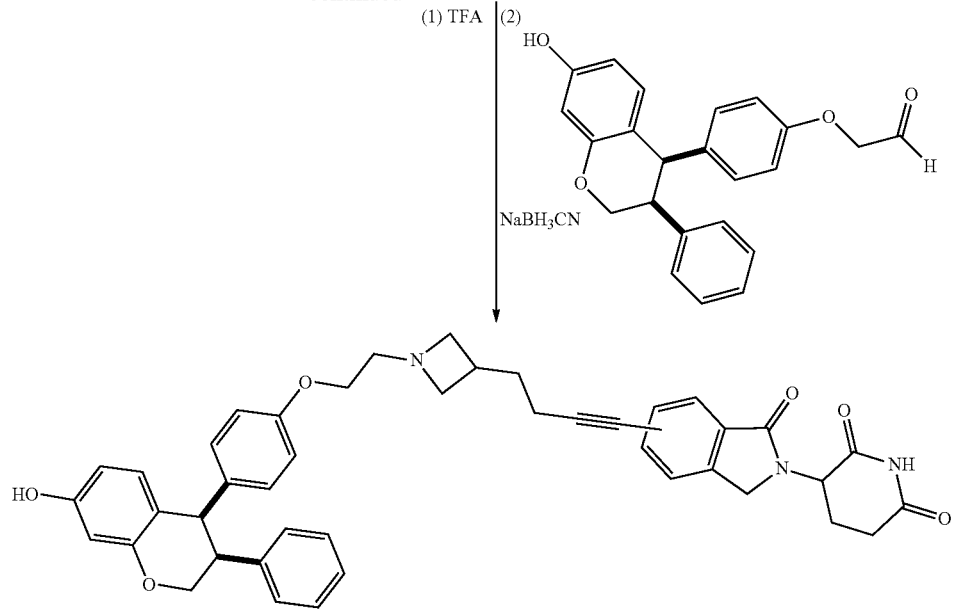
Compound 10 and 11

Scheme 7: Synthesis of Compounds 12-25
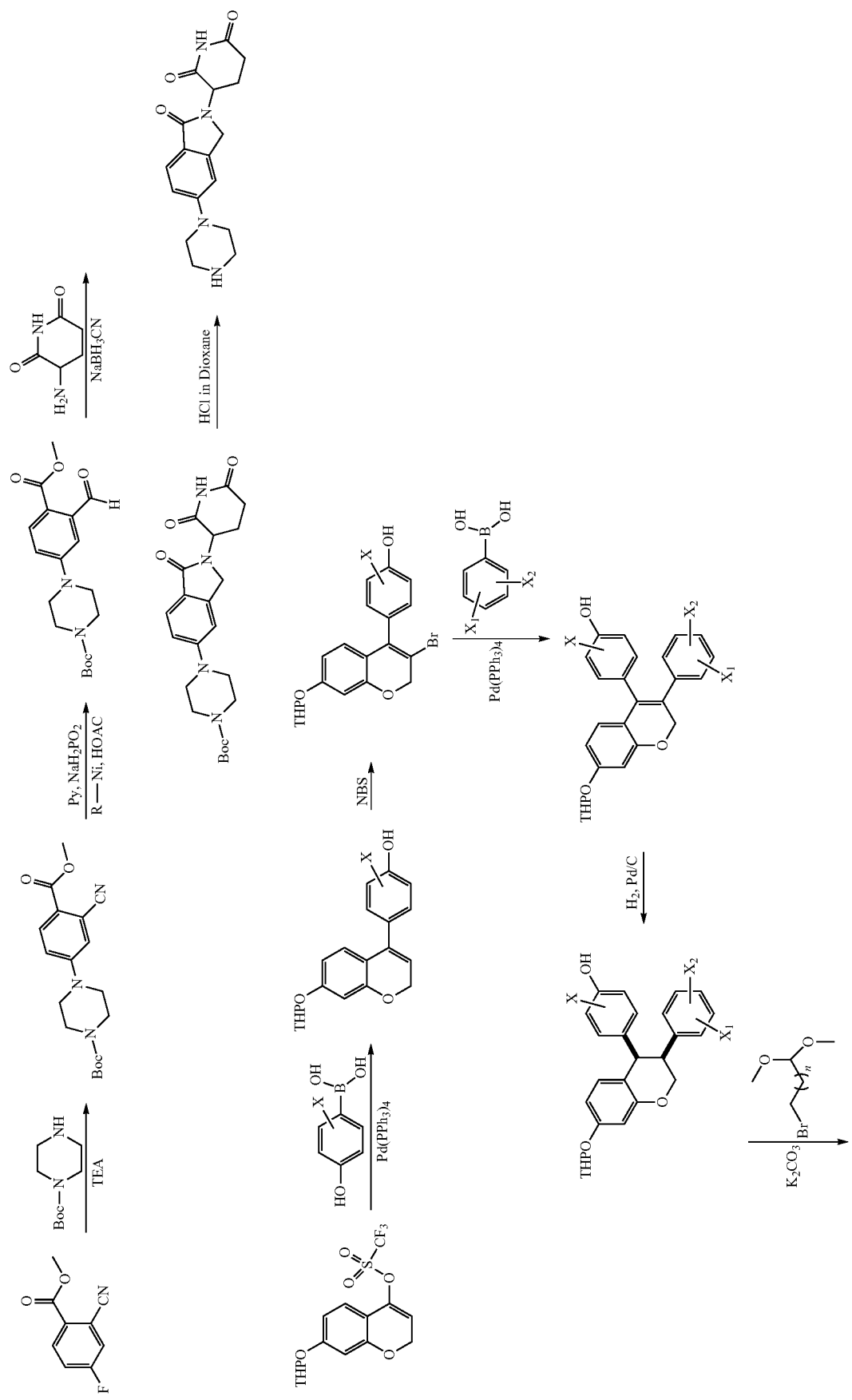

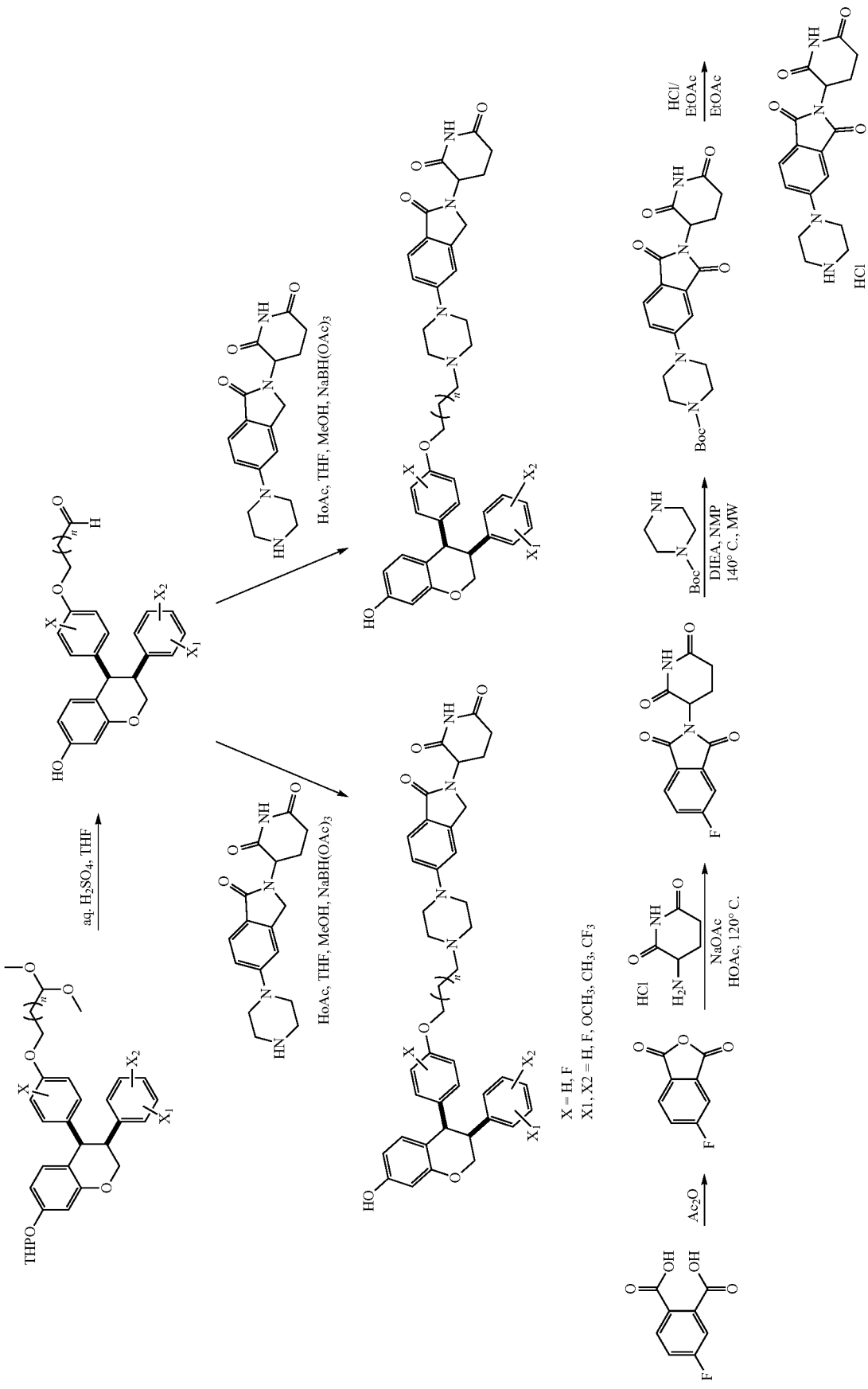

Scheme 8: Synthesis of Compounds 26, 28-31
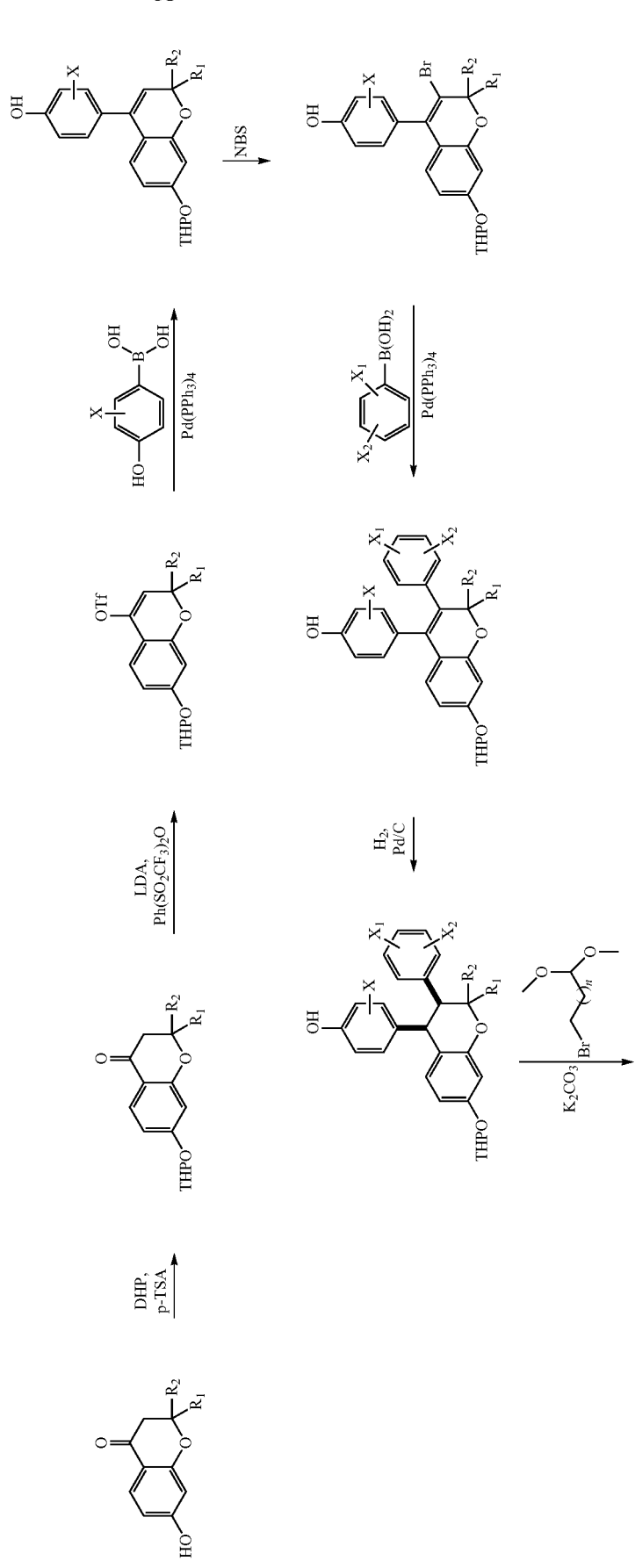

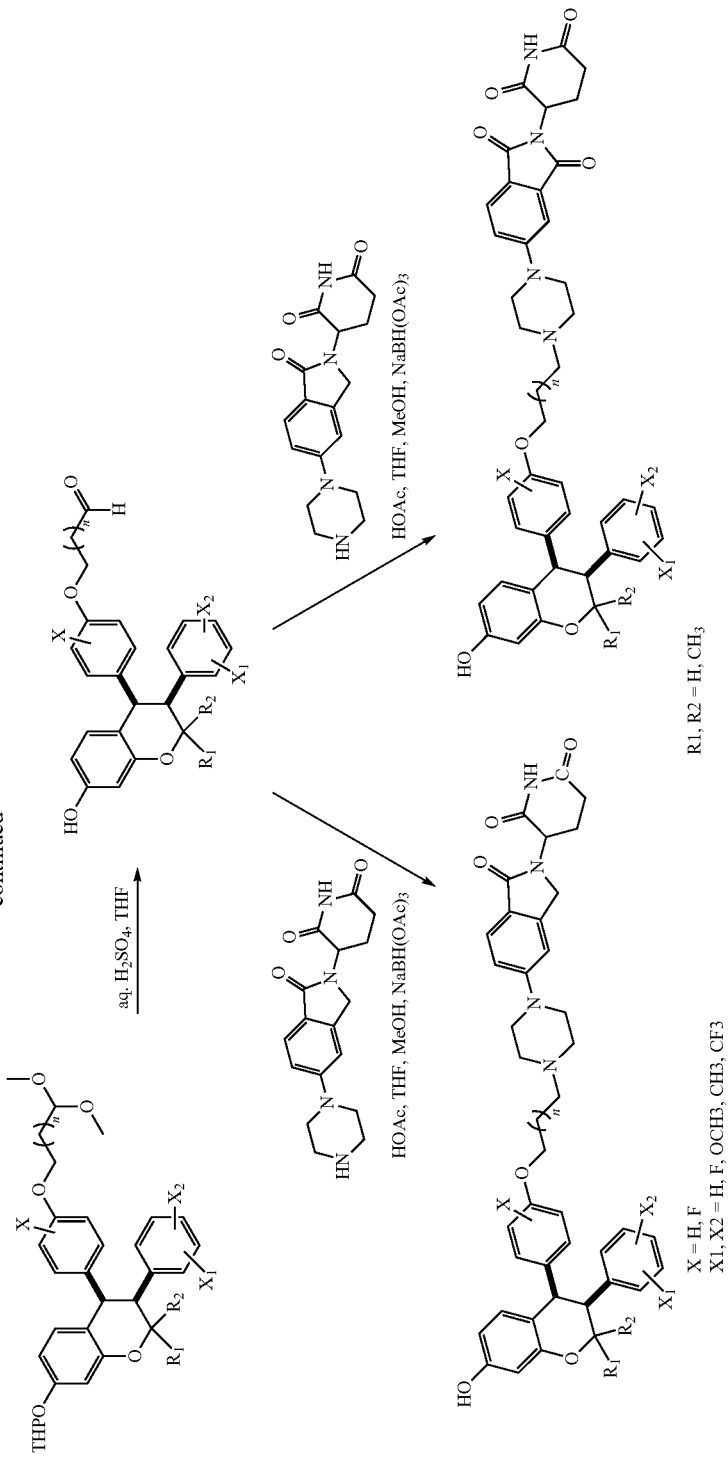

Scheme 9: Synthesis of Compound 27
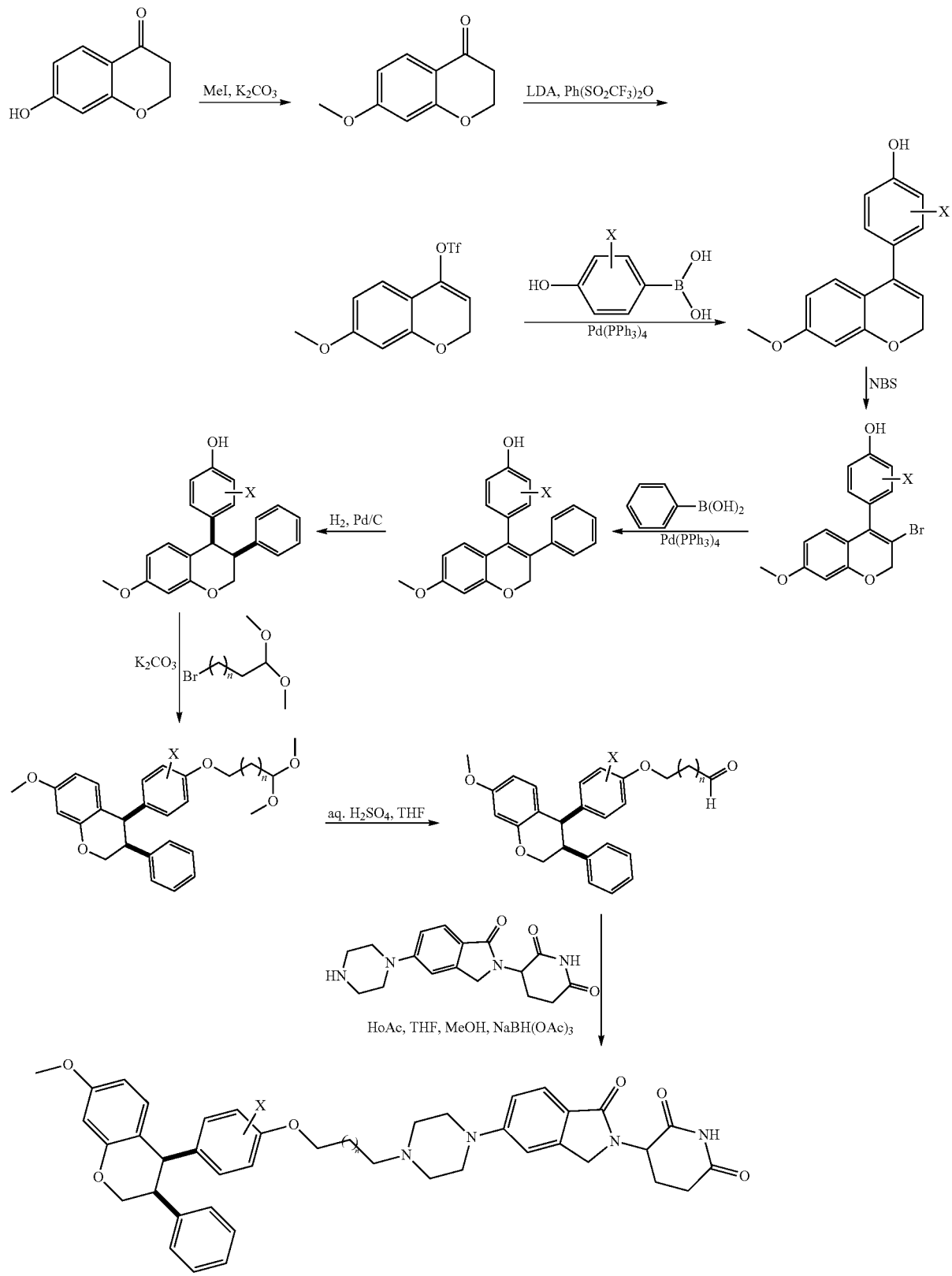
X = H, F

Scheme 10: Synthesis of Compounds 32-36
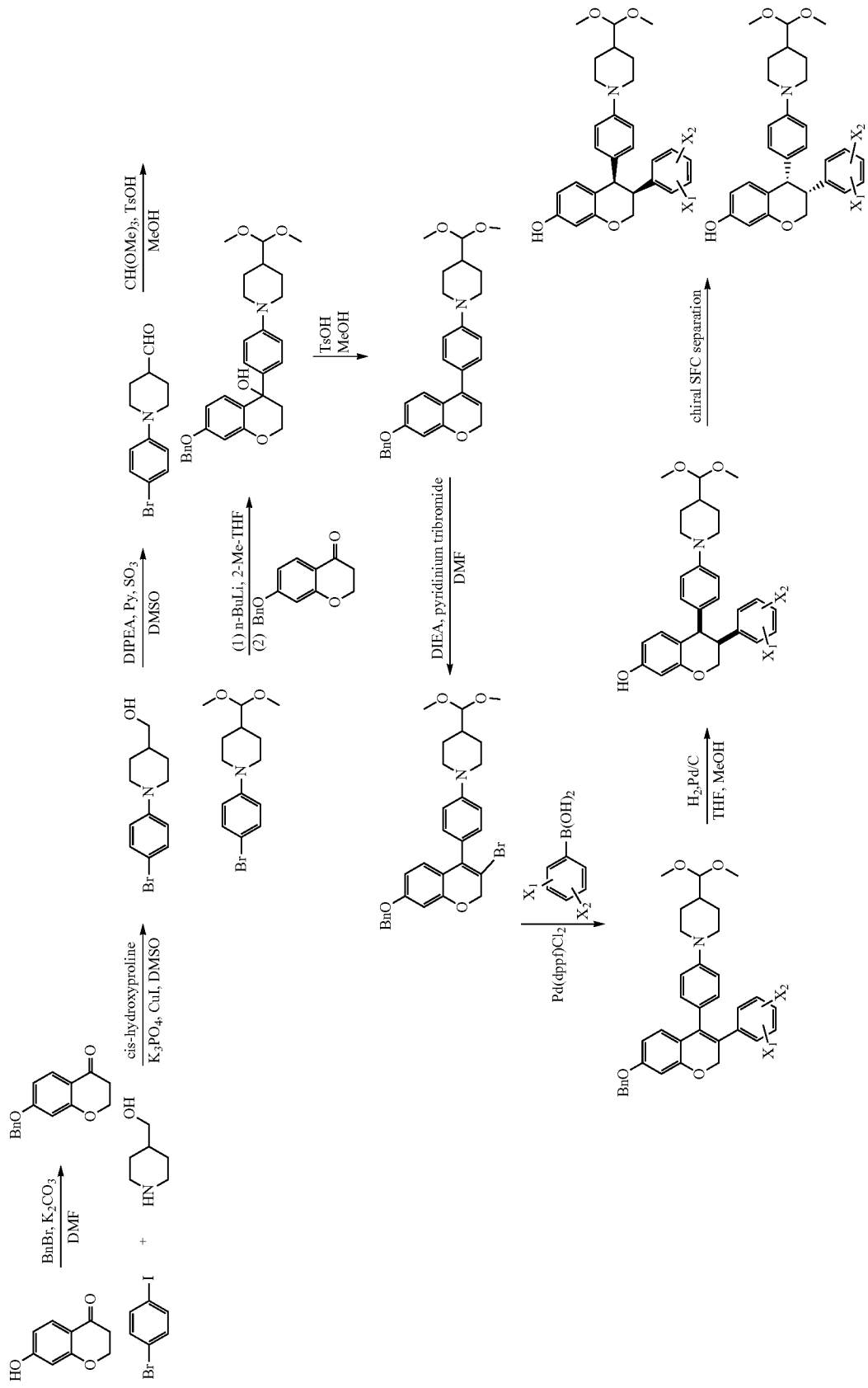

-continued
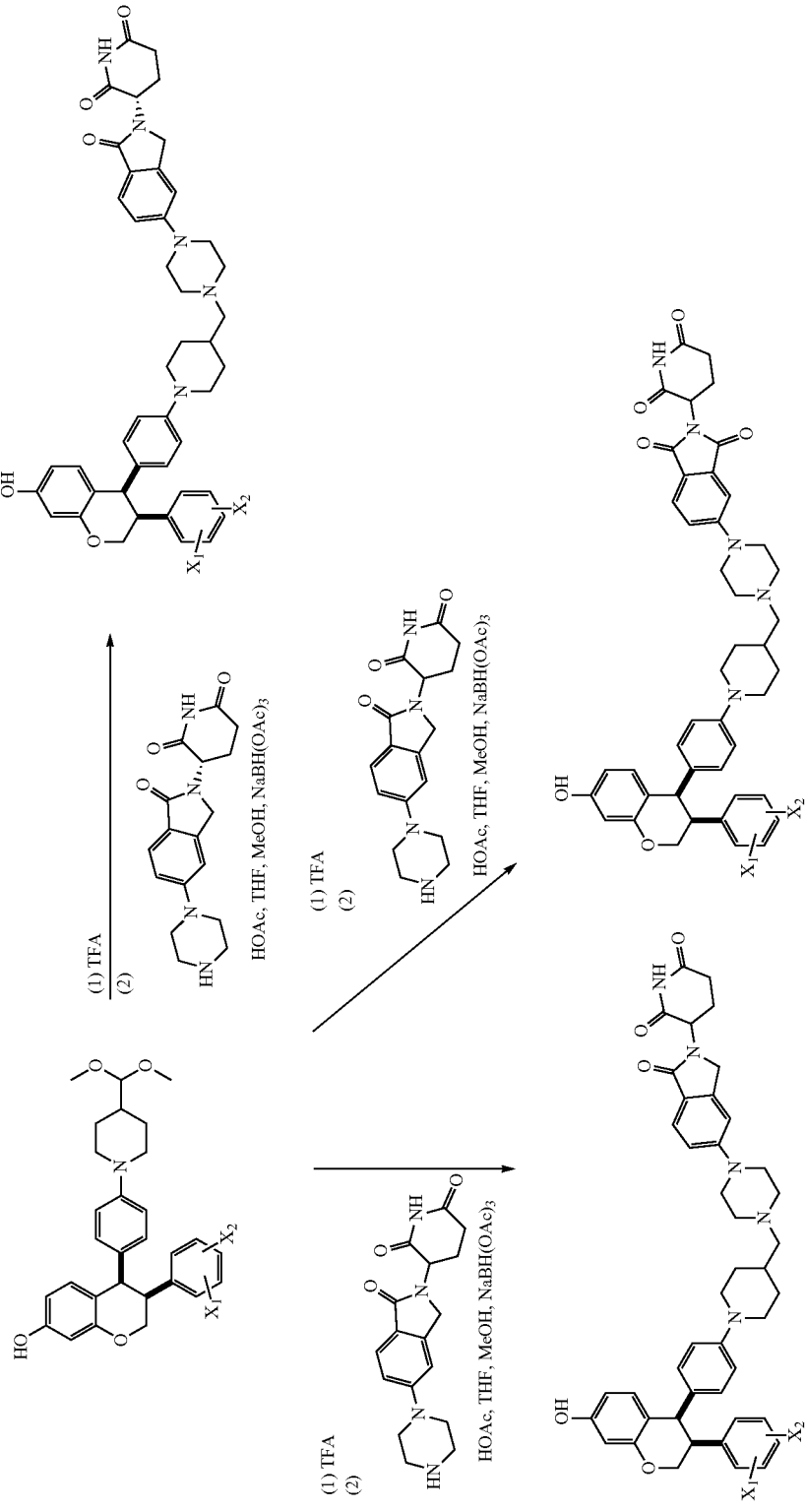

Scheme 11: Synthesis of Compounds 37 and 44.
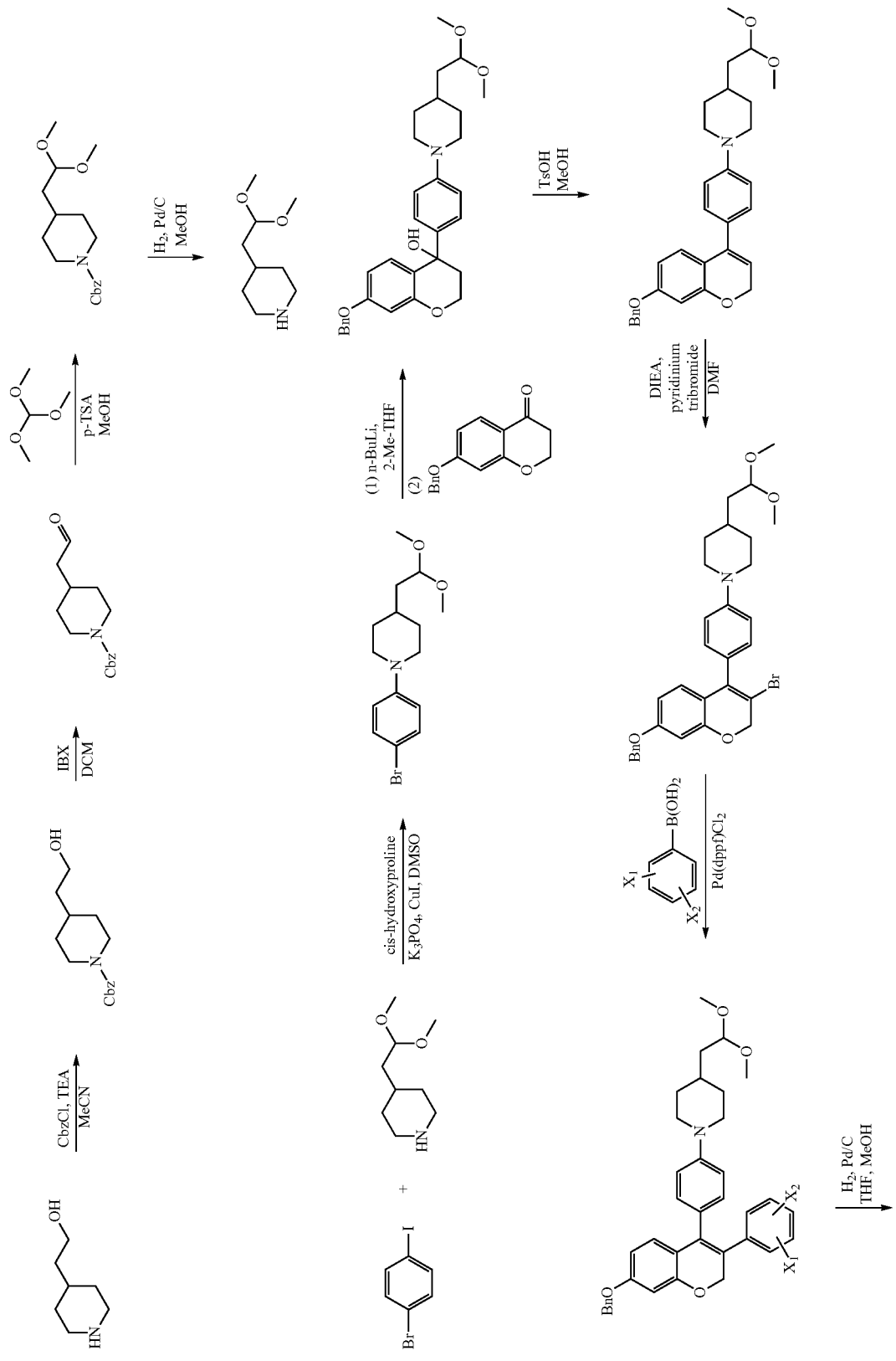

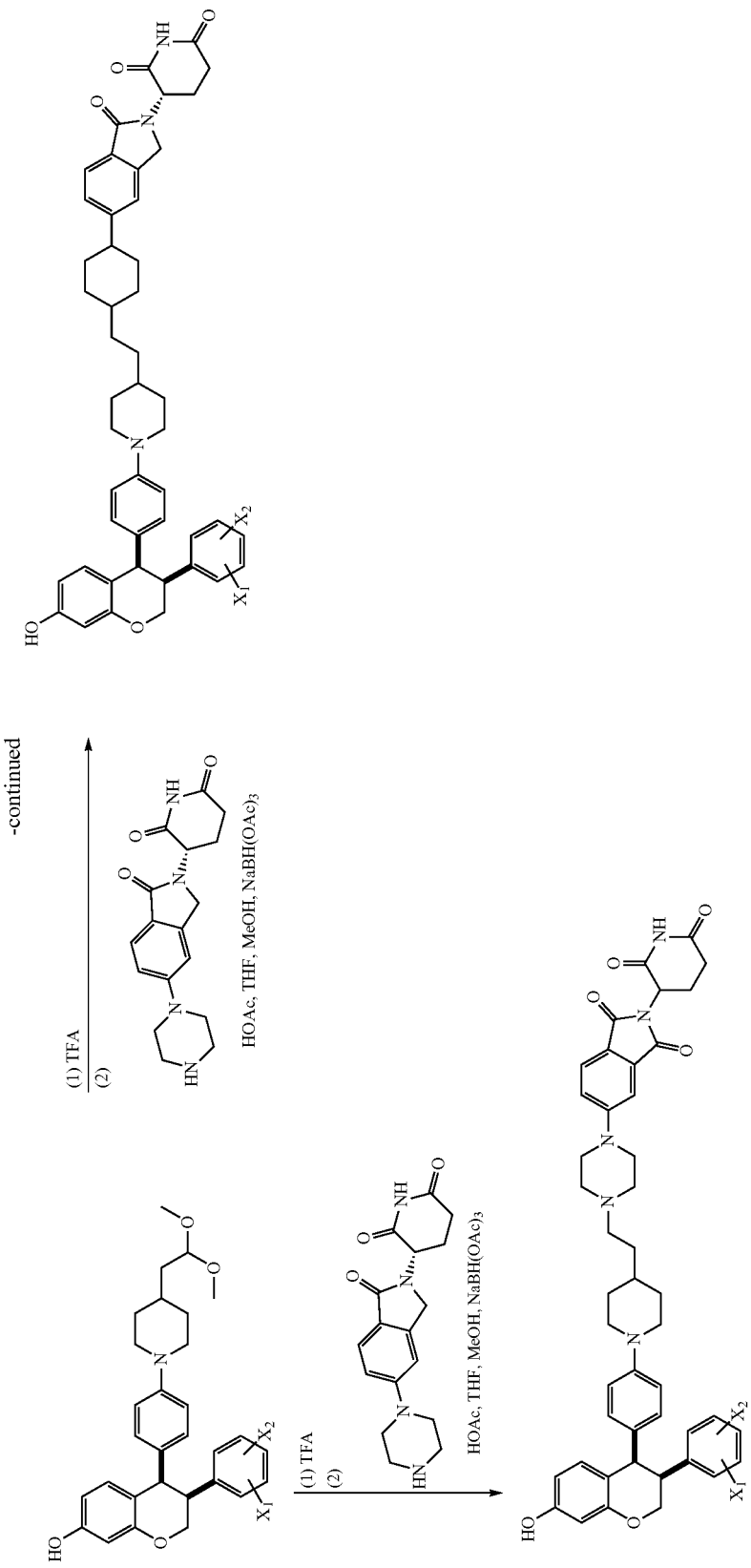

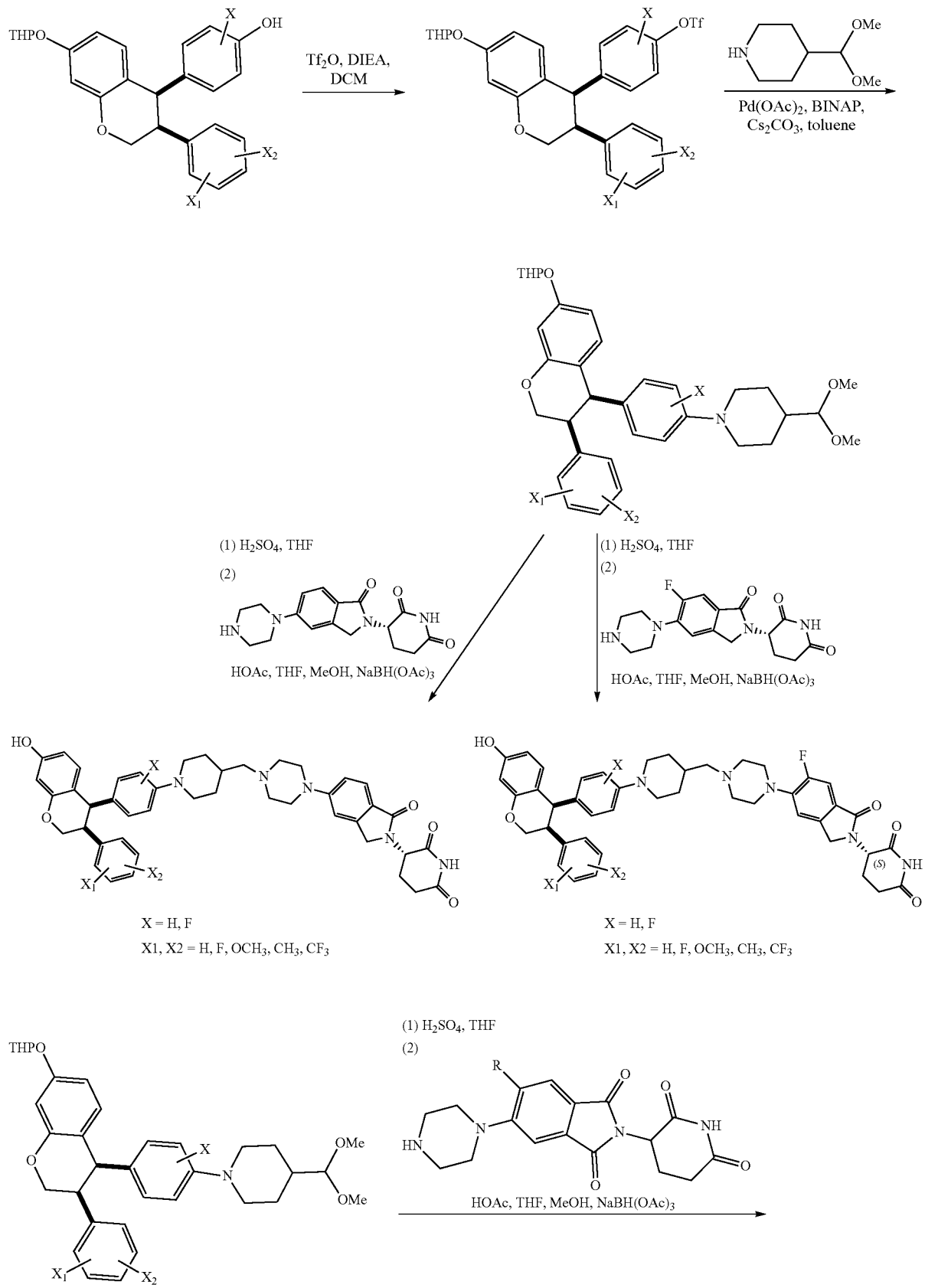
Scheme 12: Synthesis of Compounds 38-43, 45, 50-57, 60-65, 72-80, 84-87, and 89-90.

-continued
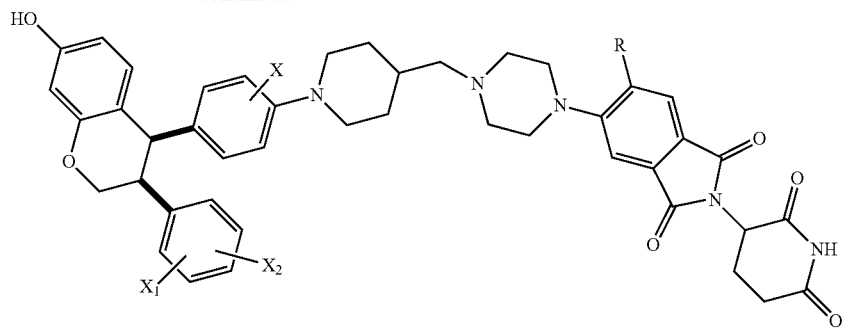
X = H, F
X1, X2 = H, F, OCH3, CH3, CF3
R = H, F
Scheme 13: Synthesis of Compounds 68-71
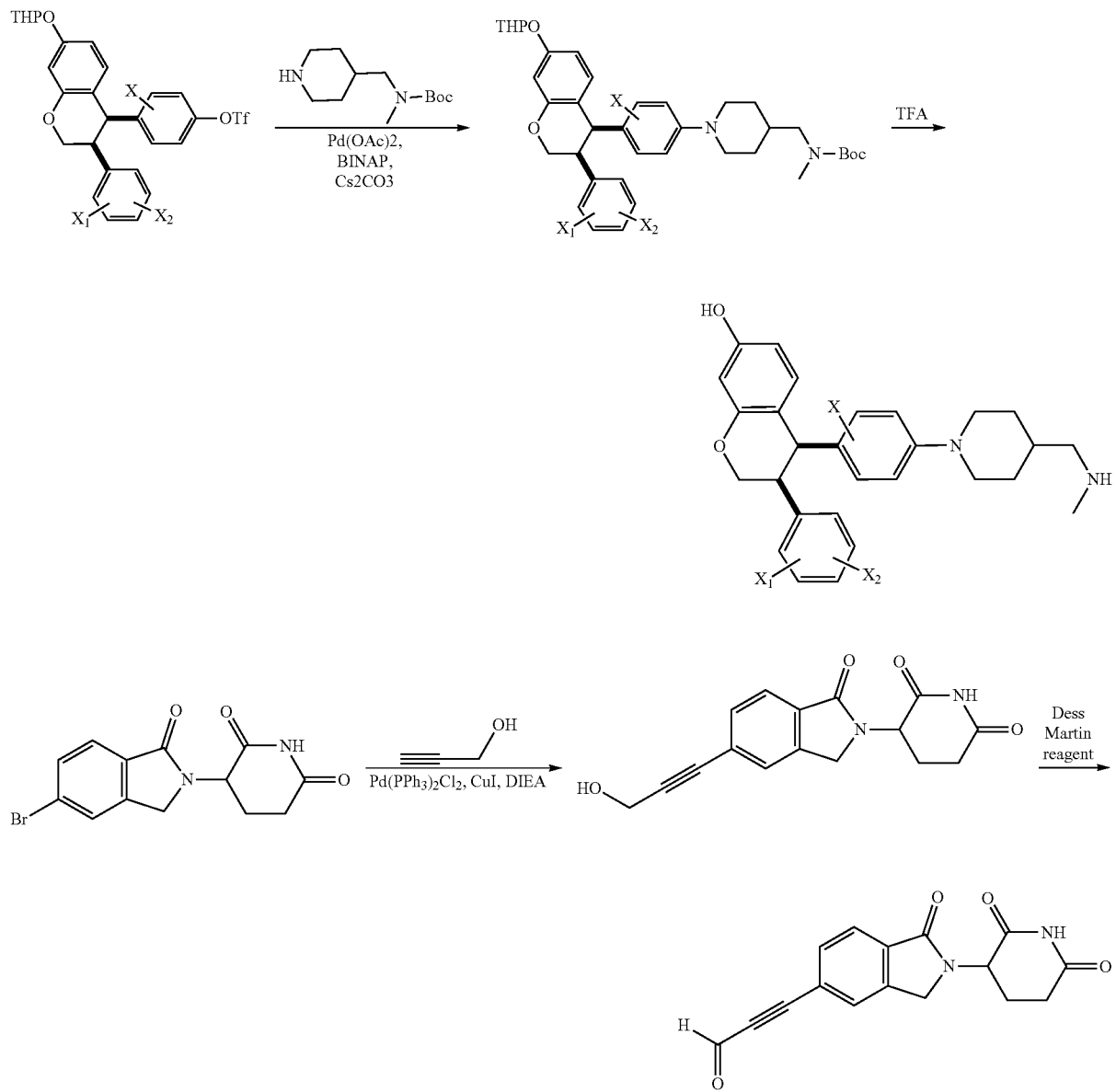

-continued
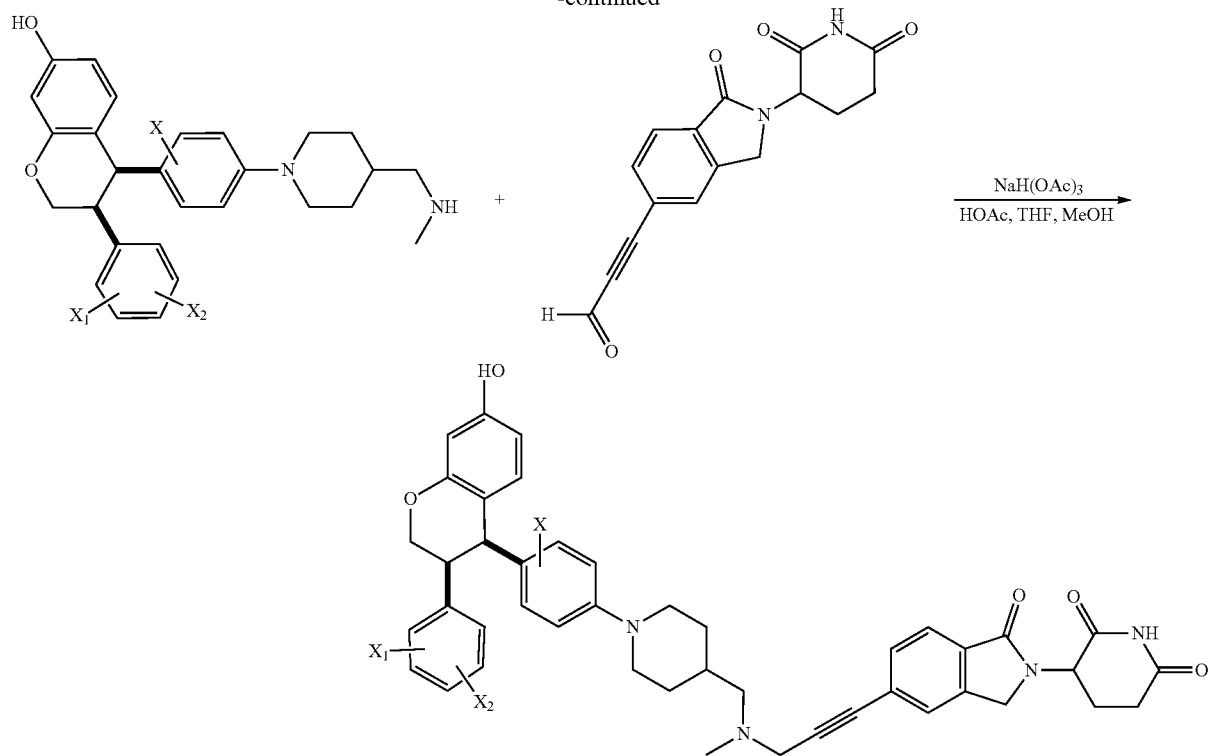
Synthesis of Compounds 46, 47, 48, 49, 58, 59, 66, 67, 81-83 and 88 can follow the schemes as described in Scheme 8, 9 and 12.
Example 1: Synthesis of cis-2-(2,6-dioxopiperidin-3-yl)-5-(4-((1-(4-(7-hydroxy-3-phenylchroman-4-yl)phenyl)piperidin-4-yl)methyl)piperazin-1-yl)isoindoline-1,3-dione (Compound 36)
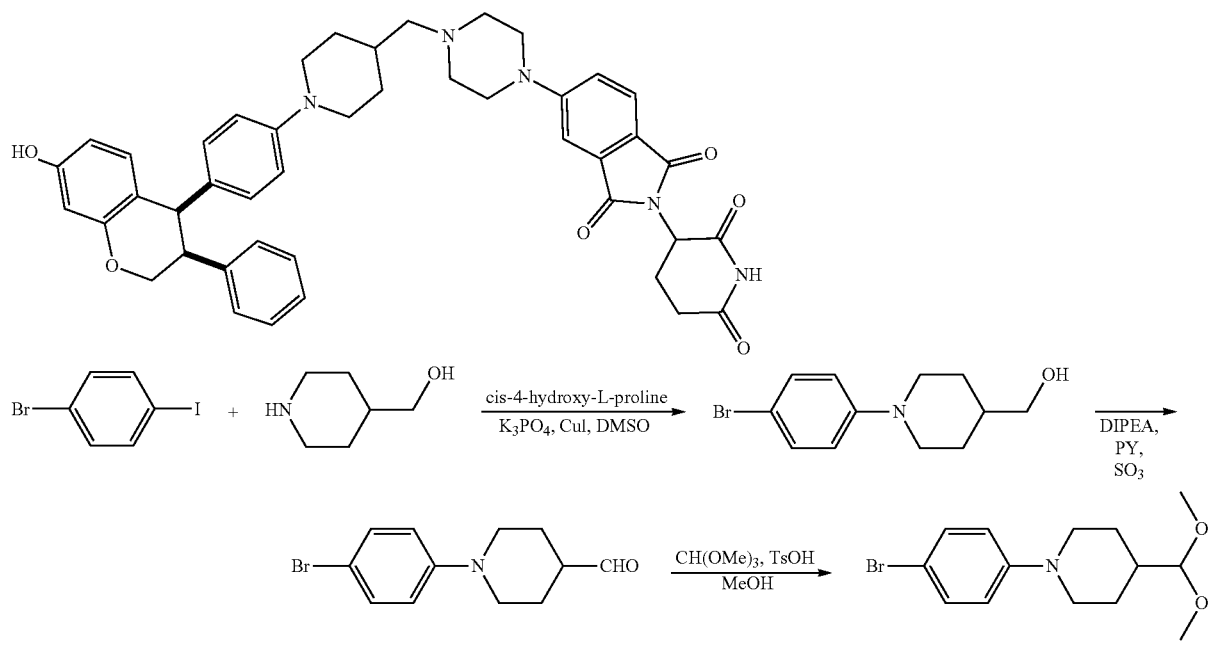

103
104
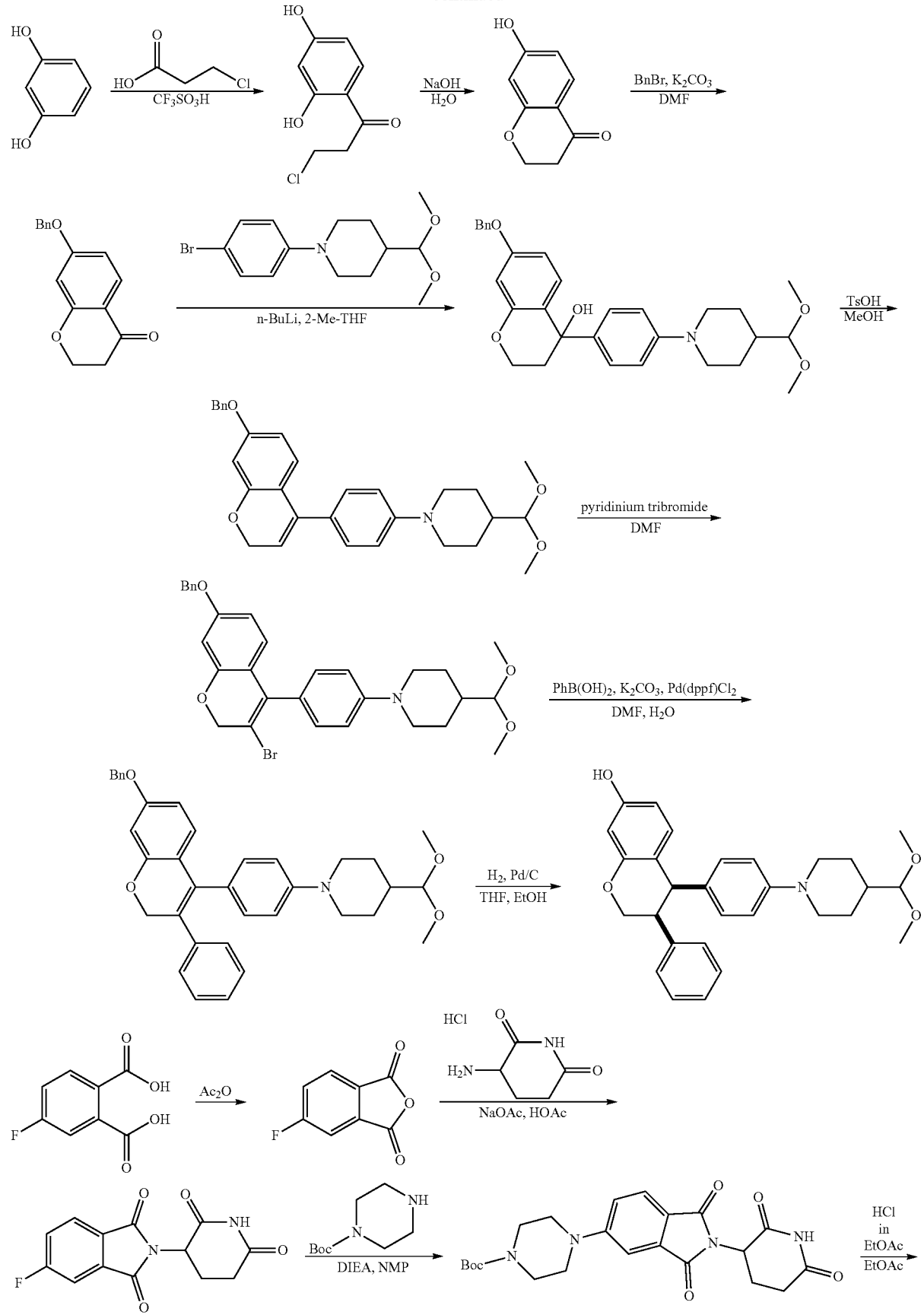
-continued

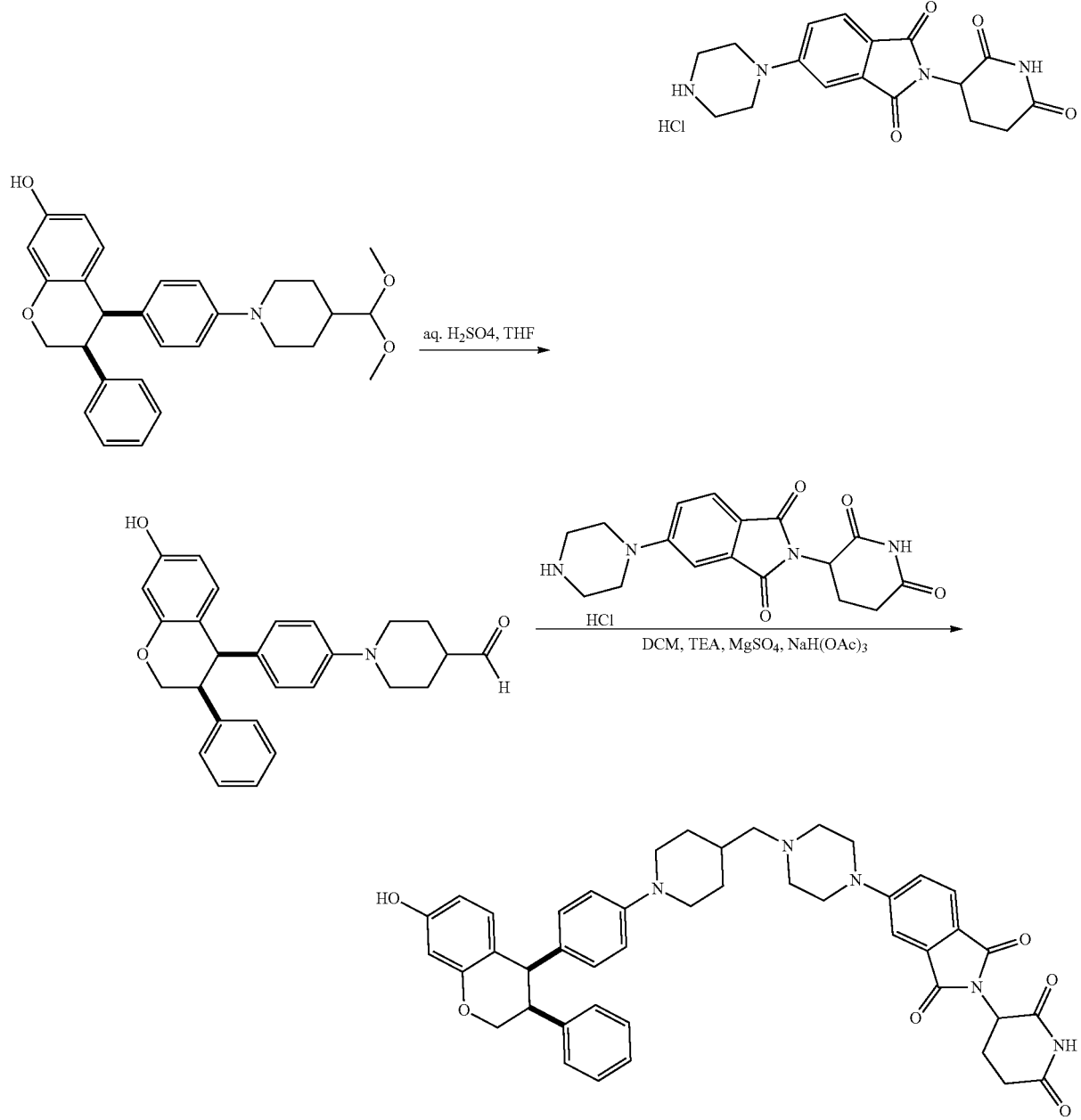

Step 1: Preparation of (1-(4-bromophenyl)piperidin-4-yl)methanol

To a mixture of 1-bromo-4-iodobenzene (100 g, 353 mmol, 1.00 eq) and piperidin-4-ylmethanol (52.8 g, 459 mmol, 1.30 eq) in DMSO (500 mL) was added cis-4-hydroxy-L-proline (9.22 g, 70.5 mmol, 0.200 eq), CuI (13.4 g, 70.5 mmol, 0.200 eq) and $K_3PO_4$ (150 g, 0.705 mol, 2.00 eq). The mixture was stirred at 80° C. for 16 hrs. TLC (petroleum ether:ethyl acetate=3:1, Rf (starting material) =0.80, Rf (product)=0.30) showed the starting material was consumed completely. The mixture was poured into ice water (2.50 L), extracted with EtOAc (1.00 L×2). The organic layer was combined and washed with ammonium hydroxide solution (500 mL×3, 30 mL of ammonium hydroxide in 210 mL of $H_2O$). The organic layer was washed with brine (500 mL), dried over $Na_2SO_4$. The mixture was filtered and the filtrate was concentrated in vacuum to provide (1-(4-bromophenyl)piperidin-4-yl)methanol as an off-white solid.

Step 2: Preparation of 1-(4-bromophenyl)piperidine-4-carbaldehyde

To a solution of (1-(4-bromophenyl)piperidin-4-yl)methanol (80.0 g, 296 mmol, 1.00 eq) in DMSO (220 mL) and DIPEA (193 g, 1.49 mol, 261 mL, 5.00 eq) was added pyridine-sulfur trioxide (143 g, 901 mmol, 3.00 eq) at 0-10° C. The mixture was stirred at 0-10° C. for 2 hrs. TLC (petroleum ether:ethyl acetate=1:1, Rf (starting material)=

0.30, Rf (product)=0.60) showed the starting material was consumed completely. This mixture was poured into ice water (2.00 L), extracted with EtOAc (500 mL×3), the combined organic phase was dried over $Na_2SO_4$, filtered and concentrated in vacuum. The residue was triturated with petroleum ether:MTBE=10:1 (150 mL) and 1-(4-bromophenyl)piperidine-4-carbaldehyde (60.0 g, crude) was obtained as a black brown solid.

Step 3: Preparation of 1-(4-bromophenyl)-4-(dimethoxymethyl)piperidine

To a solution of 1-(4-bromophenyl)piperidine-4-carbaldehyde (60.0 g, 258 mmol, 1.00 eq) and $CH(OMe)_3$ (82.9 g, 780 mmol, 85.5 mL, 3.00 eq) in MeOH (210 mL) was added TsOH (897 mg, 5.21 mmol, 0.020 eq). Then the mixture was stirred at 65° C. for 16 hrs. TLC (petroleum ether:ethyl acetate=5:1, Rf (starting material)=0.30, Rf (product)=0.50) showed the starting material was consumed completely. The resulting mixture was poured into sat. $NaHCO_3$ (100 mL), extracted with EtOAc (100 mL×3), and the combined organic phase was dried over $Na_2SO_4$, filtered and concentrated in vacuum. The residue was purified by flash column silica gel chromatography (ISCO®, 40 g SepaFlash® silica flash column, eluent of 0-100 ethyl acetate/petroleum ether gradient, 60 mL/min). The desired 1-(4-bromophenyl)-4-(dimethoxymethyl)piperidine (70.0 g, crude) was obtained as a white solid. 1H NMR (400 MHz $CDCl_3$) δ 7.32 (d, J=8.9 Hz, 2H), 6.80 (d, J=8.8 Hz, 2H), 4.08 (d, J=7.2 Hz, 1H), 3.66 (br d, J=12.4 Hz, 2H), 3.38 (s, 6H), 2.66 (td, J=12.4, 2.0 Hz, 2H), 1.67-1.91 (m, 3H), 1.45 (qd, J=12.4, 4.1 Hz, 2H).

Step 4: Preparation of 3-chloro-1-(2,4-dihydroxyphenyl)propan-1-one

To a solution of resorcinol (230 g, 2.09 mol, 348 mL, 1.00 eq) and 3-chloropropanoic acid (249 g, 2.30 mol, 1.10 eq) at 40° C. was added $CF_3SO_3H$ (1.10 kg, 7.31 mol, 645 mL, 3.50 eq), then the mixture was stirred at 80° C. for 1 hr. TLC (petroleum ether:ethyl acetate=3:1, Rf (starting material)=0.21, Rf (product)=0.35) showed the starting material was consumed completely. The resulting 3-chloro-1-(2,4-dihydroxyphenyl)propan-1-one (419 g, crude) was used to the next step directly.

Step 5: Preparation of 7-hydroxychroman-4-one

The crude 3-chloro-1-(2,4-dihydroxyphenyl)propan-1-one (419 g, 2.09 mol, 1.00 eq) was mixed with NaOH (584 g, 14.6 mol, 7.00 eq) in $H_2O$ (1.59 L), then the mixture was stirred at 0° C. for 30 min. TLC (petroleum ether:ethyl acetate=3:1, Rf (starting material)=0.40, Rf (product)=0.60) showed the starting material was consumed completely. The reaction mixture was first adjusted with 6 N HCl to pH about 5, then extracted with EtOAc (2×1.50 L). The organic layers were combined, dried over $Na_2SO_4$, filtrated and concentrated under reduced pressure to afford desired crude product (342 g, crude) as a brown gum.

Step 6: Preparation of 7-(benzyloxy)chroman-4-one

To a solution of 7-hydroxychroman-4-one (342 g, 2.08 mol, 1.00 eq) in DMF (1.50 L), was added $K_2CO_3$ (575 g, 4.17 mol, 2.00 eq) and benzylbromide (391 g, 2.29 mol, 272 mL, 1.10 eq), then the mixture was stirred at 15° C. for 12 hr. TLC (petroleum ether:ethyl acetate=3:1, Rf (starting material)=0.20, Rf (product)=0.50) showed the starting material was consumed completely. The mixture was poured into $H_2O$ (7.50 L), extracted with EtOAc (2.00 L×2). The combine organic layer was washed with brine (2.00 L), dried over $Na_2SO_4$, filtered and concentrated in vacuum. The residue was purified by column chromatography ($SiO_2$, petroleum ether:ethyl acetate=15:1 to 8:1) to provide 7-(benzyloxy)chroman-4-one (185 g) as a white solid. LCMS m/z 255 (M+H)+.

Step 7: Preparation of 7-(benzyloxy)-4-(4-(4-(dimethoxymethyl)piperidin-1-yl)phenyl)chroman-4-ol To a solution of 1-(4-bromophenyl)-4-(dimethoxymethyl)piperidine (63.0 g, 200 mmol, 1 eq) in 2-methyl-tetrahydrofunan (440 mL) was added n-BuLi (2.5 M, 96.2 mL, 1.30 eq), the mixture was stirred at −78° C. for 1 hr, then 7-(benzyloxy)chroman-4-one (50.9 g, 200 mmol, 1.00 eq) was added and the mixture was stirred at −78° C. for 1 hr. TLC (petroleum ether:ethyl acetate=3:1, Rf (starting material)=0.50, Rf (product)=0.15) showed the starting material was consumed completely. The mixture was poured into $H_2O$ (300 mL), extracted with EtOAc (50.0 mL×2), and the combined organic layer was washed with brine (50.0 mL), dried over $Na_2SO_4$, filtered and concentrated in vacuum. The crude product was triturated with petroleum ether: EtOAc (500 mL) at 15° C. for 30 min to afford 7-(benzyloxy)-4-(4-(4-(dimethoxymethyl)piperidin-1-yl)phenyl)chroman-4-ol (72.0 g, crude) a as white solid. 1H NMR (400 MHz, $CDCl_3$) δ 7.31-7.46 (m, 5H), 7.25 (d, 2H), 6.87-6.93 (m, 3H), 6.48-6.53 (m, 2H), 5.04 (s, 2H), 4.35-4.42 (m, 1H), 4.20 (dt, J=11.2 Hz, 1H), 4.09 (d, J=7.2 Hz, 1H), 3.72 (br d, J=12.0 Hz, 2H), 3.38 (s, 6H), 2.68 (br t, J=11.2 Hz, 2H), 2.25 (m, 1H), 2.15 (m, 1H), 2.10 (s, 1H, OH), 1.86 (br d, J=13.2 Hz, 2H), 1.75 (ddq, J=11.2 Hz, 1H), 1.46 (br dd, J=12.0 Hz, 2H).

Step 8: Preparation of 1-(4-(7-(benzyloxy)-2H-chromen-4-yl)phenyl)-4-(dimethoxymethyl)piperidine To a solution of 7-(benzyloxy)-4-(4-(4-(dimethoxymethyl)piperidin-1-yl)phenyl)chroman-4-ol (66.0 g, 134 mmol, 1.00 eq) in MeOH (198 mL), was added TsOH (512 mg, 2.70 mmol, 2.07e-2 eq), and the mixture was stirred at 78° C. for 30 min. TLC (petroleum ether:ethyl acetate=3:1, Rf (starting material)=0.30, Rf (product)=0.60) showed the starting material was consumed completely. The mixture was stirred at 25° C. for 30 min, filtered and the cake was dried in vacuum to afford 1-(4-(7-(benzyloxy)-2H-chromen-4-yl)phenyl)-4-(dimethoxymethyl)piperidine (60.0 g, crude) as a white solid. 1H NMR (400 MHz, $CDCl_3$) δ 7.31-7.46 (m, 5H), 7.23 (br d, J=8.2 Hz, 2H), 6.92-7.02 (m, 3H), 6.56 (s, 1H), 6.50 (dd, J=8.3 Hz, 2.3 Hz, 1H), 5.62 (t, J=4.0 Hz, 1H), 5.05 (s, 2H), 4.81 (d, J=3.8 Hz, 2H), 4.11 (d, J=7.1 Hz, 1H), 3.77 (br d, J=12.0 Hz, 2H), 3.39 (s, 6H), 2.72 (t, J=12.4 Hz, 2H), 1.88 (br d, J=13.6 Hz, 2H), 1.74-1.82 (m, 1H), 1.41-1.53 (m, 2H).

Step 9: Preparation of 1-(4-(7-(benzyloxy)-3-bromo-2H-chromen-4-yl)phenyl)-4-(dimethoxymethyl)piperidine To a solution of 1-(4-(7-(benzyloxy)-2H-chromen-4-yl)phenyl)-4-(dimethoxymethyl)piperidine (60.0 g, 139 mmol, 1.00 eq) and DIEA (36.1 g, 279 mmol, 48.7 mL, 2.00 eq) in DMF (300 mL), was added pyridinium tribromide (71.6 g, 223 mmol, 1.60 eq) at 0° C., and the mixture was stirred at 15° C. for 1 hr. TLC (petroleum ether:ethyl acetate=3:1, Rf (starting material)=0.50, Rf (product)=0.60) showed the starting material was consumed completely. The mixture was poured into $H_2O$ (700 mL), extracted with EtOAc (300 mL×2), and the organic layer was washed with brine (300 mL), dried over $Na_2SO_4$, filtered and concentrated in vacuum. The residue was purified by column chromatography ($SiO_2$, petroleum ether:ethyl acetate=30:1 to 0:1) to afford 1-(4-(7-(benzyloxy)-3-bromo-2H-chromen-4-yl)phenyl)-4-(dimethoxymethyl)piperidine (40.0 g, crude) as a yellow oil. LCMS m/z 550.2 and 552.2 [M+H]+; 1H NMR (400 MHz, $CDCl_3$) δ 7.30-7.45 (m, 5H), 7.14 (br d, J=8.4 Hz, 2H), 6.98 (br d, J=8.4 Hz, 2H), 6.67 (d, J=8.6 Hz, 1H), 6.52 (d, J=1.7 Hz, 1H), 6.43 (dd, J=8.7 and 1.7 Hz, 1H), 5.03 (s, 2H), 4.97 (s, 2H), 4.12 (d, J=7.2 Hz, 1H), 3.80 (br d, J=12.4 Hz, 2H), 3.40 (s, 6H), 2.74 (br t, J=11.8 Hz, 2H), 1.89 (brd, J=13.2 Hz, 2H), 1.74-1.84 (m, 1H), 1.43-1.56 (m, 2H).

Step 10: Preparation of 1-(4-(7-(benzyloxy)-3-phenyl-2H-chromen-4-yl)phenyl)-4-(dimethoxymethyl)piperidine To a solution of 1-(4-(7-(benzyloxy)-3-bromo-2H-chromen-4-yl)phenyl)-4-(dimethoxymethyl)piperidine (33.0 g, 59.9 mmol, 1.00 eq) in DMF (140 mL) and $H_2O$ (14 mL), was added phenylboronic acid (10.9 g, 89.9 mmol, 1.50 eq), $K_2CO_3$ (16.5 g, 119 mmol, 2.00 eq) and Pd(dppf)$Cl_2$ (855 mg, 1.17 mmol, 0.02 eq), and the mixture was stirred at 70° C. for 12 hrs. TLC (petroleum ether:ethyl acetate=3:1, Rf (starting material)=0.50, Rf (product)=0.60) showed the starting material was consumed completely. The mixture was poured into $H_2O$ (500 mL), extracted with EtOAc (200 mL×2). The combined organic layer was washed with brine (200 mL), dried over $Na_2SO_4$, filtered and concentrated in vacuum. The crude product was triturated with MeOH (100 mL) at 25° C. for 30 min to afford 1-(4-(7-(benzyloxy)-3-phenyl-2H-chromen-4-yl)phenyl)-4-(dimethoxymethyl)piperidine (30.0 g, crude) as a gray solid.

Step 11: Preparation of cis-4-(4-(4-(dimethoxymethyl)piperidin-1-yl)phenyl)-3-phenylchroman-7-ol To a solution of 1-(4-(7-(benzyloxy)-3-phenyl-2H-chromen-4-yl)phenyl)-4-(dimethoxymethyl)piperidine (30.0 g, 54.7 mmol, 1.00 eq) in THF (30.0 mL) and EtOH (300 mL) was added Pd/C (3.00 g, 10.0% purity) and Pd(OH)$_2$/C (3.00 g, 20.0% purity) under N2 atmosphere. The suspension was degassed and purged with H2 three times. The mixture was stirred under H2 (50 psi) at 60° C. for 12 hrs. TLC (petroleum ether:ethyl acetate=3:1, Rf (starting material)=0.50, Rf (product)=0.20) showed the starting material was consumed completely. The mixture was filtered, and the filtrate was concentrated in vacuum. The crude product was triturated with petroleum ether: EtOAc=10:1 (50.0 mL) at 25° C. for 30 min to afford cis-4-(4-(4-(dimethoxymethyl)piperidin-1-yl)phenyl)-3-phenylchroman-7-ol as an off-white solid. LCMS m/z 460.2 [M+H]+; 1H NMR (400 MHz, $CDCl_3$) δ 7.11-7.20 (m, 3H), 6.82 (d, J=8.3 Hz, 1H), 6.62-6.73 (m, 4H), 6.43-6.51 (m, 3H), 6.35 (dd, J=8.2, 2.5 Hz, 1H), 4.77 (br s, 1H, OH), 4.43 (t, J=11.2 Hz, 1H), 4.17-4.27 (m, 2H), 4.08 (d, J=7.4 Hz, 1H), 3.53-3.65 (m, 3H), 3.37 (s, 6H), 2.57 (t, J=10.8 Hz, 2H), 1.82 (br d, J=12.8 Hz, 2H), 1.66-1.77 (m, 1H), 1.38-1.49 (m, 2H).

Steps 12-15: Preparation of 2-(2,6-dioxopiperidin-3-yl)-5-(piperazin-1-yl)isoindoline-1,3-dione hydrochloride This compound was prepared in four steps as a hydrochloride salt as described in the scheme. LC/MS 343.1 [M+H]+; 1H-NMR (400 MHz, $CD_3OD$) δ ppm 7.76 (d, J=8.36 Hz, 1H), 7.47 (s, 1H), 7.35 (dd, J=8.36, 1.54 Hz, 1H), 5.09 (br dd, J=12.8, 5.40 Hz, 1H), 3.67-3.74 (m, 4H), 3.37-3.42 (m, 4H), 2.63-2.94 (m, 3H), 2.07-2.17 (m, 1H).

Steps 16-17: Preparation of cis-2-(2,6-dioxopiperidin-3-yl)-5-(4-((1-(4-(7-hydroxy-3-phenylchroman-4-yl)phenyl)piperidin-4-yl)methyl)piperazin-1-yl)isoindoline-1,3-dione (compound 36)

To a solution of cis-4-(4-(4-(dimethoxymethyl)piperidin-1-yl)phenyl)-3-phenylchroman-7-ol (50 mg, 0.11 mmol) in 2 mL of THF was added 2M aqueous sulfuric acid (2 mL, 4 mmol). The mixture was stirred at 70° C. for 30 minutes until all starting material was consumed. The mixture was adjusted to pH=9 with 1N NaOH solution and then extracted with ethyl acetate (10 mL×3). The combined organic layer was washed with brine, dried, filtered and concentrated under reduced pressure to give a crude product aldehyde (50 mg). LC/MS m/z 413.9 [M+H]+. The above crude aldehyde (50 mg, 0.09 mmol) was mixed with 2-(2,6-dioxopiperidin-3-yl)-5-(piperazin-1-yl)isoindoline-1,3-dione hydrochloride (37.8 mg, 0.1 mmol), TEA (18.2 mg, 0.18 mmol) in DCM (10 mL) followed by the addition of $MgSO_4$ (108 mg, 0.9 mmol). The reaction mixture was stirred at room temperature for 1 hour. Then NaBH(AcO)$_3$ (47.7 mg, 0.225 mmol) was added portion-wise in 3 hours. The reaction mixture was stirred at room temperature overnight. The resulting mixture was concentrated in vacuum to give a crude product. The crude product was purified by Prep-TLC with MeOH:DCM=1:10 to give the title compound (19.8 mg, 27.6%). LC/MS m/z 740.3 [M+H]+; 1H NMR (400 MHz, DMSO) δ 11.10 (s, 1H, NH), 9.30 (s, 1H, OH), 7.69 (d, J=8.5 Hz, 1H), 7.35 (s, 1H), 7.26 (d, J=7.5 Hz, 1H), 7.19-7.14 (m, 3H), 6.78 (d, J=3.2 Hz, 2H), 6.69-6.60 (m, 3H), 6.39 (d, J=8.2 Hz, 2H), 6.33-6.27 (m, 2H), 5.08 (dd, 1H), 4.33 (t, J=11 Hz, 1H), 4.22-4.17 (m, 2H), 3.60-3.51 (m, 3H), 3.44 (br s, 4H), 2.91-2.85 (m, 1H), 2.64-2.48 (m, 8H), 2.20 (br d, J=7.4 Hz, 2H), 2.06-1.97 (m, 1H), 1.82-1.75 (m, 2H), 1.74-1.61 (m, 1H), 1.16-1.24 (m, 2H); HRMS calculated for $C_{44}H_{45}N_5O_6$ exact mass 739.3370, observed [M+1]+ 740.3421.

Example 2: Synthesis of cis-2-(2,6-dioxopiperidin-3-yl)-5-(4-((1-(2-fluoro-4-(7-hydroxy-3-phenylchroman-4-yl)phenyl)piperidin-4-yl)methyl)piperazin-1-yl)isoindoline-1,3-dione (Compound 87)
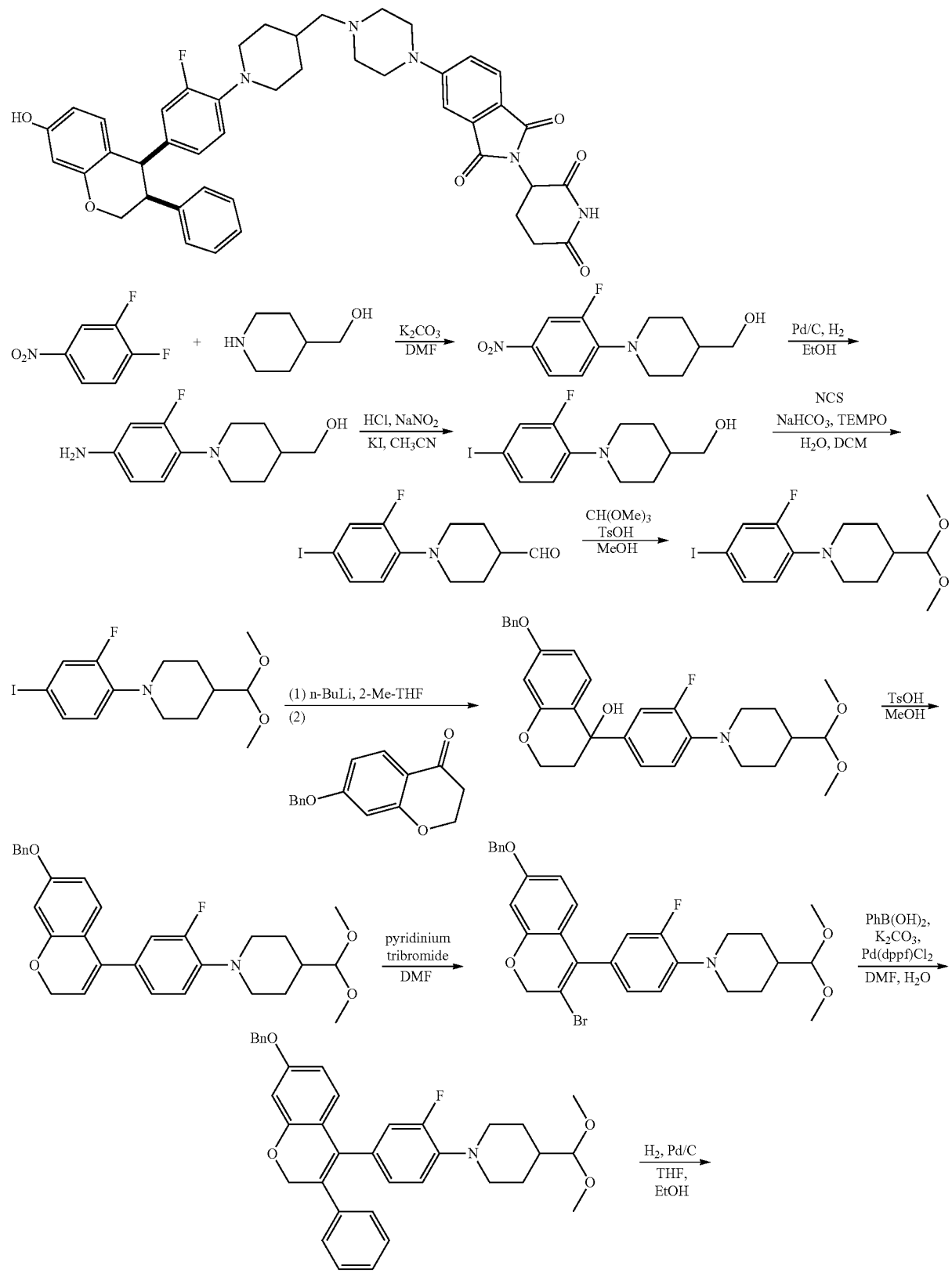

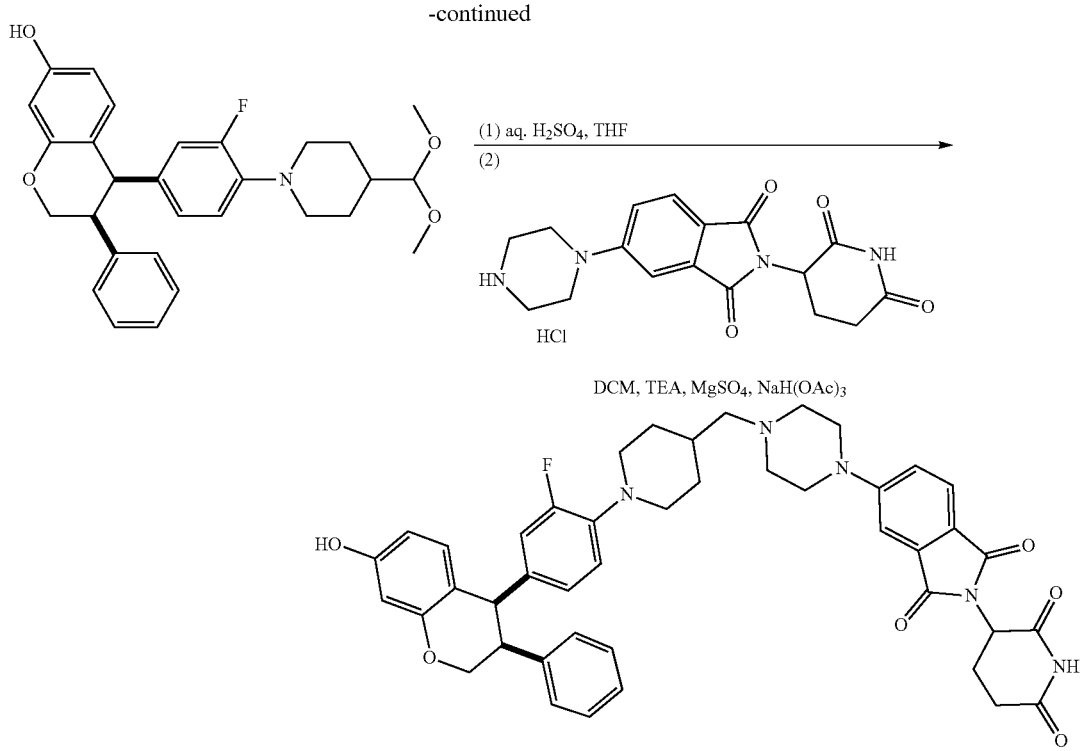

Step 1: Preparation of
(1-(2-fluoro-4-nitrophenyl)piperidin-4-yl)methanol

To a solution of compound 1,2-difluoro-4-nitrobenzene (100 g, 628 mmol, 69.4 mL, 1.00 eq) and K₂CO₃ (130 g, 942 mmol, 1.50 eq) in DMF (500 mL), was added piperidin-4-ylmethanol (76.0 g, 660 mmol, 1.05 eq) at 0° C., then the mixture was stirred at 25° C. for 12 hrs. TLC (petroleum ether:ethyl acetate=3:1, Rf (starting material)=0.50, Rf (product)=0.30) showed the starting material was consumed completely. The mixture was poured into H₂O (2.50 L), stirred for 20 min, filtered and the cake was concentrated in vacuum to provide (1-(2-fluoro-4-nitrophenyl)piperidin-4-yl)methanol (158 g, 621 mmol, 98.8% yield) as a yellow solid.

Step 2: Preparation of
(1-(4-amino-2-fluorophenyl)piperidin-4-yl)methanol

To a solution of (1-(2-fluoro-4-nitrophenyl)piperidin-4-yl)methanol (158 g, 424 mmol, 1.00 eq) in MeOH (1.00 L) was added Pd/C (1.60 g, 10% purity) under argon. The suspension was degassed under vacuum and purged with H₂ several times. The mixture was stirred under H₂ (50 psi) at 50° C. for 12 hr. TLC (petroleum ether:ethyl acetate=3:1, Rf (starting material)=0.30, Rf (product)=0.10) showed the starting material was consumed completely. The mixture was filtered and the filtrate was concentrated in vacuum to provide (1-(4-amino-2-fluorophenyl)piperidin-4-yl)methanol. as a brown solid.

Step 3: Preparation of
(1-(2-fluoro-4-iodophenyl)piperidin-4-yl)methanol

To a solution of (1-(4-amino-2-fluorophenyl)piperidin-4-yl)methanol (90.0 g, 401 mmol, 1.00 eq) in MeCN (360 mL) cooled to 0° C. was added HCl (12 M, 100 mL, 3.00 eq), then NaNO₂ (33.2 g, 481 mmol, 1.20 eq) in H₂O (40.0 mL) was added dropwise at 0° C., the mixture was stirred for 0.5 hr followed by the addition of KI (166 g, 1.00 mol, 2.50 eq) in H₂O (100 mL) at 0° C. The mixture was stirred at 15° C. for 11 hrs. TLC (petroleum ether:ethyl acetate=1:1, Rf (starting material)=0.25, Rf (product)=0.10) showed the starting material was consumed completely. The mixture was filtered and the cake was triturated with sat. NaOH (4M, 500 mL) at 15° C. for 30 min, filtered, and the cake (brown solid) was used into the next step.

Step 4: Preparation of
1-(2-fluoro-4-iodophenyl)piperidine-4-carbaldehyde

To a solution of NaHCO₃ (46.8 g, 558 mmol, 1.70 eq) and Na₂CO₃ (6.05 g, 57.1 mmol, 0.174 eq) in H₂O (750 mL) was added (1-(2-fluoro-4-iodophenyl)piperidin-4-yl)methanol (110 g, 328 mmol, 1 eq) in DCM (750 mL), then TBAB (10.6 g, 33.1 mmol, 0.101 eq), TEMPO (1.29, 8.21 mmol, 0.020 eq) and NCS (54.7 g, 410 mmol, 1.00 eq) were added at 0° C., the mixture was stirred at 0° C. for 1.5 hrs. TLC (petroleum ether:ethyl acetate=3:1, Rf (starting material)=0.25, Rf (product)=0.50) showed the starting material was consumed completely. The mixture was extracted with DCM (500 mL×2). The combined organic layer was washed with saturated Na2SO3 solution (200 mL) and brine (200 mL), dried over Na2SO4, filtered and concentrated under reduced pressure to give 1-(2-fluoro-4-iodophenyl)piperidine-4-carbaldehyde (90.0 g, crude) as a brown solid.

Step 5: Preparation of 4-(dimethoxymethyl)-1-(2-fluoro-4-iodophenyl)piperidine

To a solution of 1-(2-fluoro-4-iodophenyl)piperidine-4-carbaldehyde (90.0 g, 270 mmol, 1.00 eq) in MeOH (600 mL), was added CH(OCH3)3 (43.0 g, 405 mmol, 1.50 eq) and TsOH (6.98 g, 40.5 mmol, 0.150 eq), then the mixture was stirred at 65° C. for 12 hrs. TLC (petroleum ether:ethyl acetate=3:1, Rf (starting material)=0.35, Rf (product)=0.60) showed the starting material was consumed completely. The pH was adjusted to 9 by progressively adding sat. NaHCO$_3$. The mixture was concentrated in vacuum, then the mixture was added to H$_2$O (200 mL), extracted with EtOAc (500 mL×2), the combined organic layer was washed with brine (200 mL), dried over Na$_2$SO$_4$, filtered and concentrated in vacuum. The residue was purified by column chromatography (SiO$_2$, petroleum ether/ethyl acetate=30/1 to 10/1) to afford 4-(dimethoxymethyl)-1-(2-fluoro-4-iodophenyl)piperidine (90.0 g, 237 mmol, 87.7% yield) as a yellow solid.

Step 6: Preparation of 7-(benzyloxy)-4-(4-(4-(dimethoxymethyl)piperidin-1-yl)-3-fluorophenyl)chroman-4-ol To a solution of 1-(4-iodo-2-fluorophenyl)-4-(dimethoxymethyl)piperidine (45 g, 118 mmol, 1.00 eq) in 2-methyl-tetrahydrofuran (225 mL), was added n-BuLi (2.5 M, 61.5 mL, 1.30 eq) at −65° C., the mixture was stirred at −65° C. for 0.5 hr, then 7-(benzyloxy)chroman-4-one (22.5 g, 88.9 mmol, 0.750 eq) in 2-methyl-tetrahydrofuran (100 mL) was added at −65° C., and the mixture was stirred at −65° C. for 2.5 hrs. TLC (petroleum ether:ethyl acetate=3:1, Rf (starting material)=0.50, Rf (product)=0.15) showed the starting material was consumed completely. The same reaction was repeated one more time and two reactions were combined for workup. The mixture was poured into H$_2$O (300 mL), extracted with EtOAc (50.0 mL×2), and the combined organic layer was washed with brine (50.0 ml), dried over Na$_2$SO$_4$, filtered and concentrated in vacuum to afford 7-(benzyloxy)-4-(4-(4-(dimethoxymethyl)piperidin-1-yl)-3-fluorophenyl)chroman-4-ol (85.0 g, crude) as a red solid.

Step 7: Preparation of 1-(4-(7-(benzyloxy)-2H-chromen-4-yl)-2-fluorophenyl)-4-(dimethoxymethyl)piperidine To a solution of 7-(benzyloxy)-4-(4-(4-(dimethoxymethyl)piperidin-1-yl)-3-fluorophenyl)chroman-4-ol (85.0 g, 165 mmol, 1.00 eq) in MeOH (255 mL) was added TsOH (588 mg, 3.42 mmol, 0.021 eq) at 15° C. The mixture was stirred at 75° C. for 0.5 hr. TLC (petroleum ether:ethyl acetate=3:1, Rf (starting material)=0.30, Rf (product)=0.60) showed the starting material was consumed completely. The mixture was stirred at 25° C. for 30 min, filtered and the cake was dried in vacuum to provide 1-(4-(7-(benzyloxy)-2H-chromen-4-yl)-2-fluorophenyl)-4-(dimethoxymethyl)piperidine (75.0 g, 140 mmol, 77.1% yield) as red solid. 1H NMR (400 MHz, CDCl$_3$) δ 7.30-7.46 (m, 5H), 6.88-7.06 (m, 4H), 6.56 (d, J=2.3 Hz, 1H), 6.51 (dd, J=8.6, 2.4 Hz, 1H), 5.64 (t, J=3.9 Hz, 1H), 5.06 (s, 2H), 4.80 (d, J=3.9 Hz, 2H), 4.12 (d, J=7.2 Hz, 1H), 3.53 (br d, J=11.6 Hz, 2H), 3.40 (s, 6H), 2.68 (br t, J=11.2 Hz, 2H), 1.87 (br d, J=12.8 Hz, 2H), 1.76 (m, 1H), 1.45-1.65 (m, 2H).

Step 8: Preparation of 1-(4-(7-(benzyloxy)-3-bromo-2H-chromen-4-yl)-2-fluorophenyl)-4-(dimethoxymethyl)piperidine To a solution of 1-(4-(7-(benzyloxy)-2H-chromen-4-yl)-2-fluorophenyl)-4-(dimethoxymethyl)piperidine (75.0 g, 153 mmol, 1.00 eq) and DIEA (59.0 g, 459 mmol, 80.0 mL, 3.00 eq) in DMF (350 mL) was added pyridinium tribromide (73.0 g, 245 mmol, 1.60 eq) at ° C. under N$_2$. The mixture was stirred at 15° C. for 1 hr. TLC (petroleum ether:ethyl acetate=3:1, Rf (starting material)=0.50, Rf (product)=0.60) showed the starting material was consumed completely. The mixture was poured into H$_2$O (1.00 L), extracted with EtOAc (300 mL) twice, and the organic layer was washed with brine (300 mL), dried over Na$_2$SO$_4$, filtered and concentrated in vacuum. The crude product was triturated with MTBE (250 mL) at room temperature for 30 min to provide 1-(4-(7-(benzyloxy)-3-bromo-2H-chromen-4-yl)-2-fluorophenyl)-4-(dimethoxymethyl)piperidine (90.0 g, crude) as a red solid. 1H NMR (400 MHz, CDCl$_3$) δ 7.31-7.49 (m, 5H), 6.85-7.06 (m, 3H), 6.63 (m, 1H), 6.53 (d, J=2.20 Hz, 1H), 6.44 (dd, J=8.6, 2.4 Hz, 1H), 5.03 (s, 2H), 4.98 (s, 2H), 4.13 (d, J=7.3 Hz, 1H), 3.50-3.62 (m, 2H), 3.40 (s, 6H), 2.71 (br t, J=11.2 Hz, 2H), 1.70-1.93 (m, 3H), 1.56 (qd, J=12.0, 3.6 Hz, 2H).

Step 9: Preparation of 1-(4-(7-(benzyloxy)-3-phenyl-2H-chromen-4-yl)-2-fluorophenyl)-4-(dimethoxymethyl)piperidine To a solution of 1-(4-(7-(benzyloxy)-3-bromo-2H-chromen-4-yl)-2-fluorophenyl)-4-(dimethoxymethyl)piperidine (85.0 g, 148 mmol, 1.00 eq) in DMF (400 mL) and H$_2$O (40.0 mL), was added phenylboronic acid (25.4 g, 208 mmol, 1.40 eq), K$_2$CO$_3$ (45.7 g, 330 mmol, 2.22 eq) and Pd(dppf)Cl$_2$ (2.50 g, 3.429 mmol, 0.023 eq). The mixture was stirred at 70° C. under N$_2$ for 12 hrs. TLC (petroleum ether:ethyl acetate=3:1, Rf (starting material)=0.50, Rf (product)=0.55) showed the starting material was consumed completely. The mixture was poured into H$_2$O (1.50 L), and stirred at 15° C. for 30 min. The solid was filtered and the cake was dried in vacuum to provide 1-(4-(7-(benzyloxy)-3-phenyl-2H-chromen-4-yl)-2-fluorophenyl)-4-(dimethoxymethyl)piperidine (60.0 g, crude) as a red solid. 1H NMR (400 MHz, CDCl$_3$) δ 7.30-7.49 (m, 5H), 7.07-7.22 (m, 3H), 6.98 (d, 2H), 6.72-6.88 (m, 4H), 6.65 (s, 1H), 6.50 (d, 1H), 5.06 (br s, 4H), 4.11 (br dd, J=5.6, 1.2 Hz, 1H), 3.46-3.53 (m, 2H), 3.39 (s, 6H), 2.63 (t, J=11 Hz, 2H), 1.87 (br d, 2H), 1.75 (m, 1H), 1.45-1.63 (m, 2H).

Step 10: Preparation of cis-4-(4-(4-(dimethoxymethyl)piperidin-1-yl)-3-fluorophenyl)-3-phenylchroman-7-ol To a solution of 1-(4-(7-(benzyloxy)-3-phenyl-2H-chromen-4-yl)-2-fluorophenyl)-4-(dimethoxymethyl)piperidine (30.0 g, 53.1 mmol, 1.00 eq) in THF (75.0 mL) and EtOH (300.0 mL) was added Pd/C (3 g, 10% purity) under N2 atmosphere. The suspension was degassed and purged with H$_2$ three times. The mixture was stirred under H$_2$ (50 psi) at 50° C. for 12 hrs. TLC (petroleum ether:ethyl acetate=3:1, Rf (starting material)=0.50, Rf (product)=0.20) showed the starting material was consumed completely. The resulting mixture was filtered, and the filtarte was concentrated in vacuum. The same size of hydrogenation reaction was repeated, and the two reactions were combined for purification. The crude product was triturated with petroleum ether:EtOAc=10:1 (200 mL) at 25° C. for 30 min to provide cis-4-(4-(4-(dimethoxymethyl)piperidin-1-yl)-3-fluorophenyl)-3-phenylchroman-7-ol (50.0 g, 96.8% purity)

as an off-white solid. LCMS m/z 478.2 [M+H]+; 1H NMR (400 MHz, CDCl3) δ 7.12-7.23 (m, 3H), 6.80 (d, J=8.3 Hz, 1H), 6.60-6.73 (m, 3H), 6.46 (d, J=2.4 Hz, 1H), 6.38 (dd, J=8.3, 2.6 Hz, 1H), 6.22-6.30 (m, 2H), 4.72 (br s, 1H), 4.41 (t, J=11.2 Hz, 1H), 4.25 (dd, J=10.8, 2.4 Hz, 1H), 4.19 (d, J=5.2 Hz, 1H), 4.09 (d, J=7.4 Hz, 1H), 3.54-3.61 (m, 1H), 3.37 (s and m, 8H), 2.54 (brt, J=11.8 Hz, 2H), 1.82 (brd, J=12.8 Hz, 2H), 1.65-1.76 (m, 1H), 1.43-1.56 (m, 2H).

Step 11: Preparation of cis-2-(2,6-dioxopiperidin-3-yl)-5-(4-((1-(2-fluoro-4-(7-hydroxy-3-phenylchroman-4-yl)phenyl)piperidin-4-yl)methyl)piperazin-1-yl)isoindoline-1,3-dione (Compound 87)

This step of the reaction was carried out using the same method as described in steps 16-17 of Example 1. LC/MS m/z 758.7 [M+H]+; 1H NMR (400 MHz, DMSO) δ 11.10 (s, 1H), 9.36 (s, 1H), 7.69 (d, J=8.2 Hz, 1H), 7.35 (s, 1H), 7.26 (d, J=7.7 Hz, 1H), 7.22-7.08 (m, 3H), 6.86-6.64 (m, 4H), 6.38-6.26 (m, 3H), 6.15 (d, J=14.0 Hz, 1H), 5.08 (dd, J=13.0, 5.4 Hz, 1H), 4.33 (t, J=11 Hz, 1H), 4.26-4.21 (m, 2H), 3.60-3.52 (m, 1H), 3.49-3.39 (br s, 4H), 3.27-3.18 (m, 2H), 2.93-2.84 (m, 1H), 2.69-2.48 (m, 8H), 2.20 (br d, 2H), 2.07-1.96 (m, 1H), 1.83-1.73 (m, 2H), 1.70-1.60 (m, 1H), 1.16-1.24 (m, 2H); HRMS calculated for C44H44FN5O6 exact mass 757.3276, observed [M+1]+ 758.3336.

Example 3: Synthesis of (S)-3-(6-fluoro-5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 41)

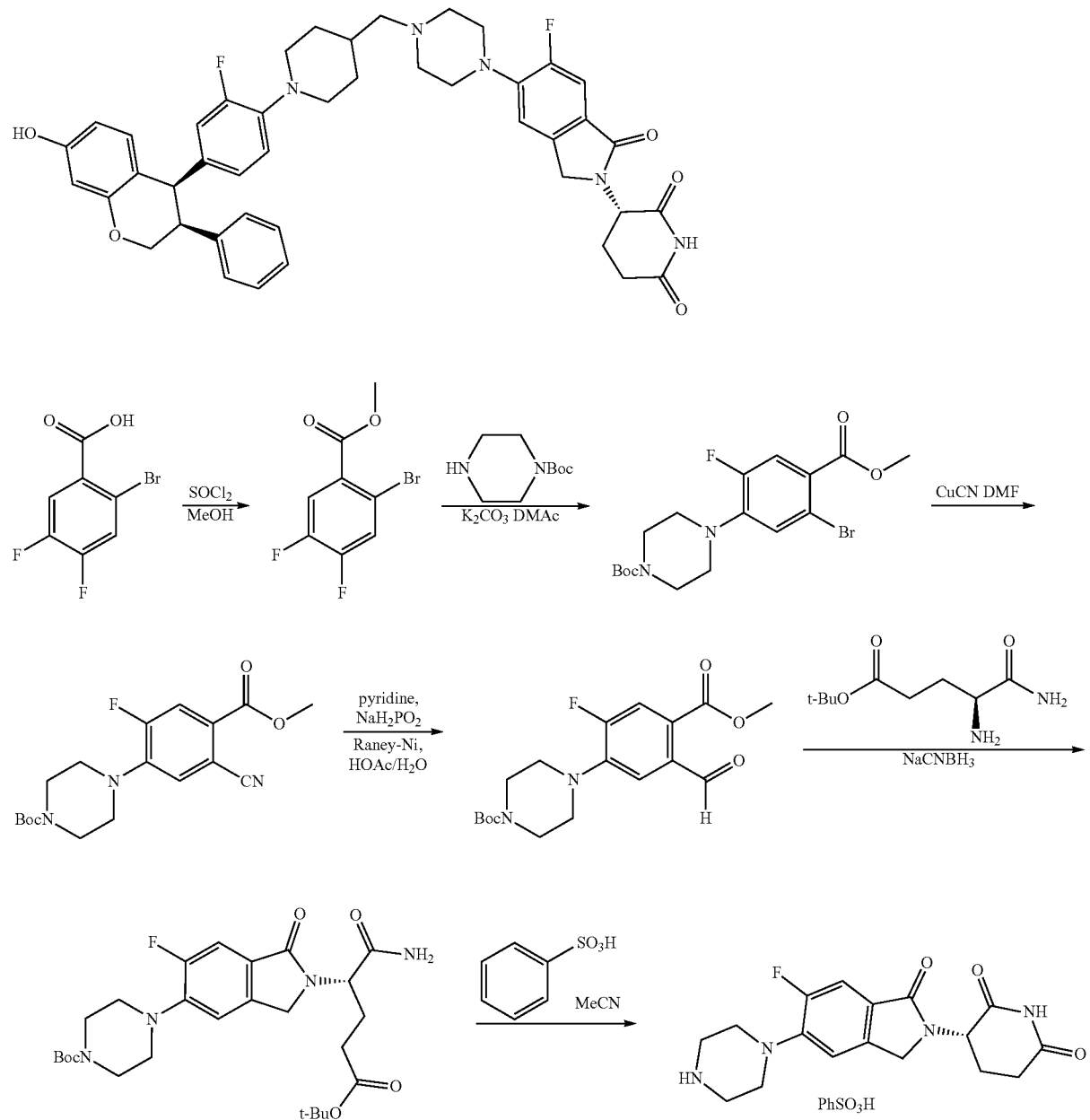

119

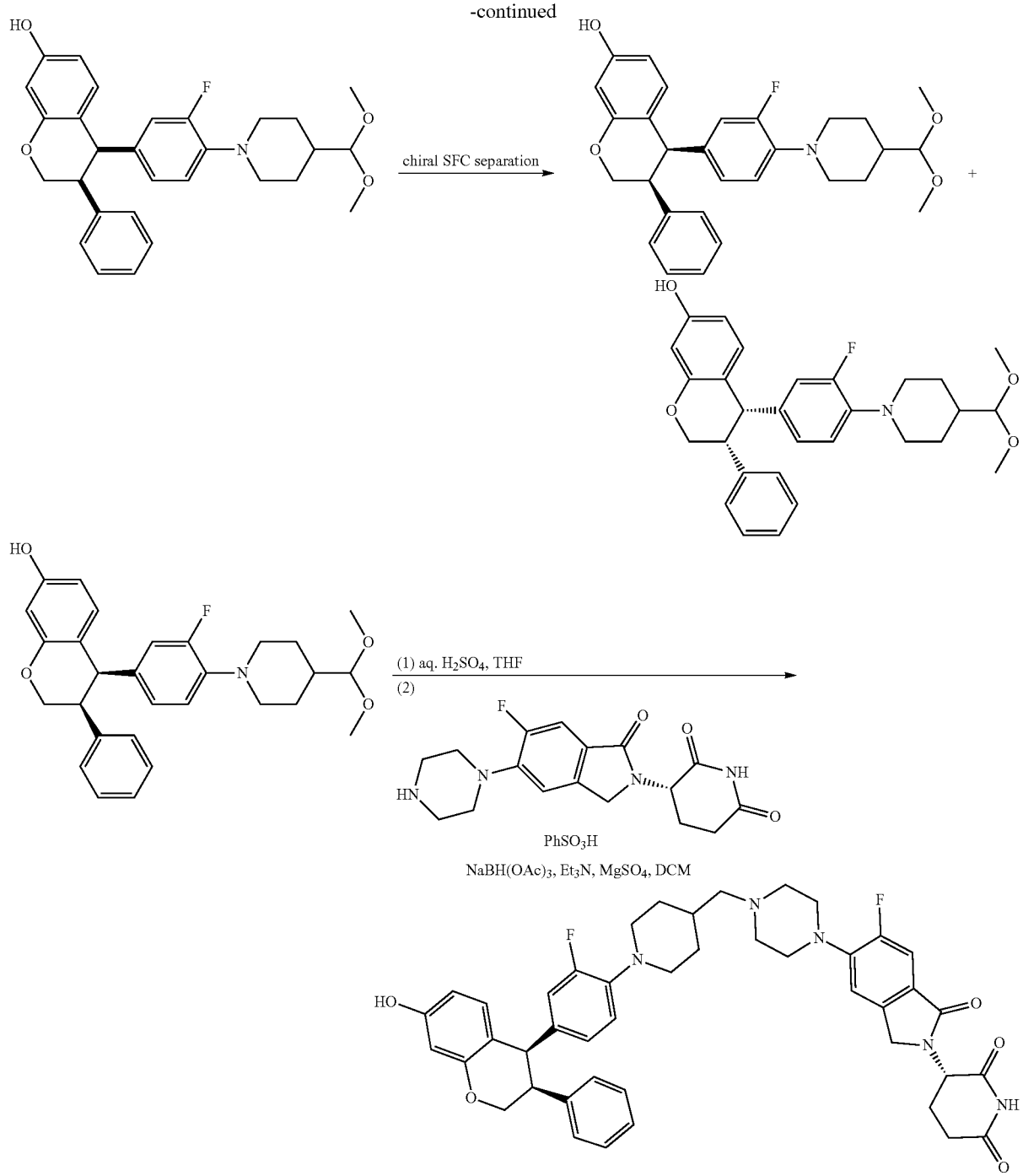

Step 1: Preparation of methyl 2-bromo-4,5-difluorobenzoate

Thionyl chloride (130 g, 1.09 mol) was added slowly to a mixture of 2-bromo-4,5-difluorobenzoic acid (200 g, 0.84 mol) in MeOH (600 mL) at 10° C., the mixture was stirred at 80° C. for 3 h. TLC showed the reaction was completed. The mixture was cooled to room temperature, concentrated, then partitioned between ethyl acetate and water. The organic layer was washed with saturated Na₂CO₃ and brine twice, dried over Na₂SO₄ and concentrated to afford a crude methyl 2-bromo-4,5-difluorobenzoate (210 g, yield: 100%) which was used for the next step without further purification.

Step 2: Preparation of tert-butyl 4-(5-bromo-2-fluoro-4-(methoxycarbonyl)phenyl)piperazine-1-carboxylate A mixture of methyl 2-bromo-4,5-difluorobenzoate (210 g, 0.84 mol), tert-butyl piperazine-1-carboxylate (234 g, 1.25 mol) and K₂CO₃ (173 g, 1.25 mol) in N,N-dimethylacetamide (600 mL) was stirred at 80° C. for 16 h. TLC showed the reaction was completed. The mixture was added to water (2 L) and stirred for 10 min followed by the addition of ethyl acetate. The mixture was partitioned between ethyl acetate and water. The organic layer was washed with water, brine, dried over $Na_2SO_4$ and concentrated to afford tert-butyl 4-(5-bromo-2-fluoro-4-(methoxycarbonyl)phenyl)piperazine-1-carboxylate (315.8 g, yield: 90%).

Step 3: Preparation of tert-butyl 4-(5-cyano-2-fluoro-4-(methoxycarbonyl)phenyl)piperazine-1-carboxylate A mixture of tert-butyl 4-(5-bromo-2-fluoro-4-(methoxycarbonyl)phenyl)piperazine-1-carboxylate (306 g, 0.73 mol) and CuCN (98 g, 1.09 mol) in DMF (1.2 L) was stirred at 100° C. for 16 h. TLC showed the reaction was completed. The mixture was cooled to room temperature. Ethyl acetate (2 L) and ammonium hydroxide (2 L) were added and the mixture was stirred for 30 min. The mixture was filtered. The organic layer was washed with water, dried over $Na_2SO_4$ and concentrated to afford a crude product (254 g). This crude product was taken into petroleum ether (1 L) at reflux. The mixture was filtered and dried in oven at 50° C. to afford tert-butyl 4-(5-cyano-2-fluoro-4-(methoxycarbonyl)phenyl)piperazine-1-carboxylate (215 g, yield: 81%).

Step 4: Preparation of tert-butyl 4-(2-fluoro-5-formyl-4-(methoxycarbonyl)phenyl)piperazine-1-carboxylate To a solution of pyridine (391 g, 4.95 mol), water (200 mL), acetic acid (264 g, 4.4 mol) was added tert-butyl 4-(5-cyano-2-fluoro-4-(methoxycarbonyl)phenyl)piperazine-1-carboxylate (200 g, 0.55 mol) and Raney-nickel (85% in water, 100 g) at room temperature. The resulting mixture was heated to 60° C. Sodium hypophosphite (292 g in 500 mL water) was added dropwise into the mixture. The mixture was stirred for 16 h at 60° C. TLC showed the reaction not completed. The mixture was further stirred for 10 h. The mixture was cooled to room temperature. Ethyl acetate and water were added. The mixture was filtered. The organic layer was washed with water, 1N HCl and brine, dried over $Na_2SO_4$ and concentrated under reduced pressure to afford a crude product (208 g, crude) which was further purified by silica-gel pad to provide 4-(2-fluoro-5-formyl-4-(methoxycarbonyl)phenyl)piperazine-1-carboxylate (86.5 g, yield: 43%).

Step 5: Preparation of tert-butyl (S)-4-(2-(1-amino-5-(tert-butoxy)-1,5-dioxopentan-2-yl)-6-fluoro-1-oxoisoindolin-5-yl)piperazine-1-carboxylate To a solution of tert-butyl 4-(2-fluoro-5-formyl-4-(methoxycarbonyl)phenyl)piperazine-1-carboxylate (81.5 g, 0.22 mol) in methanol (500 mL) was added tert-butyl (S)-4,5-diamino-5-oxopentanoate (54 g, 0.27 mol) at room temperature. Acetic acid (19.8 g, 0.33 mol) was added at 0° C. followed by the addition of sodium cyanoborohydride (27.6 g, 0.44 mol) slowly. The mixture was stirred at room temperature for 16 hours. TLC showed the reaction was completed. The mixture was concentrated and partitioned between ethyl acetate and water. The organic layer was washed with saturated citric acid, brine, dried over $Na_2SO_4$ and concentrated under reduced pressure to afford a crude product which was further purified by silica-gel pad to give tert-butyl (S)-4-(2-(1-amino-5-(tert-butoxy)-1,5-dioxopentan-2-yl)-6-fluoro-1-oxoisoindolin-5-yl)piperazine-1-carboxylate (80 g, yield: 69%).

Step 6: Preparation of (S)-3-(6-fluoro-1-oxo-5-(piperazin-1-yl)isoindolin-2-yl)piperidine-2,6-dione benzenesulfonic acid To a solution of (S)-4-(2-(1-amino-5-(tert-butoxy)-1,5-dioxopentan-2-yl)-6-fluoro-1-oxoisoindolin-5-yl)piperazine-1-carboxylate (67 g, 0.13 mol) in acetonitrile (670 mL) was added benzenesulfonic acid (43 g, 0.26 mol). The mixture was stirred at 80° C. for 16 h. LCMS showed the reaction was complete. The mixture was cooled to room temperature. The mixture was filtered and dried to afford (S)-3-(6-fluoro-1-oxo-5-(piperazin-1-yl)isoindolin-2-yl)piperidine-2,6-dione benzenesulfonic acid (56 g, 86%) as off-white solid. $^1$H NMR (400 MHz, DMSO-d6) δ 1.94-1.99 (m, 1H), 2.35-2.43 (m, 1H), 2.58-2.62 (m, 1H), 2.88-2.91 (m, 1H), 3.30 (br s, 8H), 4.38 (d, J=17.2 Hz, 1H), 4.26 (d, J=17.2 Hz, 1H), 5.08 (dd, J=13.2, 5.2 Hz, 1H), 7.29-7.35 (m, 4H), 7.49 (d, J=8.7 Hz, 1H), 7.60 (m, 2H), 8.72 (s, 2H), 10.99 (s, 1H). LCMS m/z 347.3 [M+1]$^+$.

Step 7: Preparation of (3S,4R)-4-(4-(4-(dimethoxymethyl)piperidin-1-yl)-3-fluorophenyl)-3-phenylchroman-7-ol The racemic cis-4-(4-(4-(dimethoxymethyl)piperidin-1-yl)-3-fluorophenyl)-3-phenylchroman-7-ol prepared from step 10 of Compound 87 (50.0 g, 104 mmol) was separated by chiral SFC (column: DAICEL CHIRALCEL OD (250 mm×30 mm, 10 um); mobile phase: [0.1% $NH_3H_2O$ MeOH]; B %: 60%-60%).

The first fraction collected provided (3R,4S)-4-(4-(4-(dimethoxymethyl)piperidin-1-yl)-3-fluorophenyl)-3-phenylchroman-7-ol (15.0 g, 99.4% purity) as an off-white solid. $[α]_D^{25}$=335.8 (1 g/100 mL in EtOAc); LCMS m/z 478.2 [M+1]$^+$; $^1$H NMR (400 MHz, DMSO-d6) δ 9.34 (s, 1H), 7.12-7.23 (m, 3H), 6.65-6.86 (m, 4H), 6.25-6.35 (m, 3H), 6.13 (d, 1H), 4.30 (t, 1H), 4.23 (m, 2H), 4.07 (d, J=6.4 Hz, 1H), 3.53 (m, 1H), 3.25 (s, 6H), 3.15-3.24 (m, 2H), 2.42-2.50 (m, 2H), 1.57-1.72 (m, 3H), 1.22-1.40 (m, 2H).

The second fraction collected provided (3S,4R)-4-(4-(4-(dimethoxymethyl)piperidin-1-yl)-3-fluorophenyl)-3-phenylchroman-7-ol (16.0 g, 98.1% purity) as a brown solid. $[α]_D^{25}$=−303.9 (0.5 g/100 mL in EtOAc); LCMS m/z 478.2 [M+1]$^+$; $^1$H NMR (400 MHz, DMSO-d6) δ 9.45 (br s, 1H), 7.16 (m, 3H), 6.65-6.80 (m, 4H), 6.25-6.32 (m, 3H), 6.13 (d, J=13.6 Hz, 1H), 4.32 (t, 1H), 4.17-4.27 (m, 2H), 4.07 (d, J=6.4 Hz, 1H), 3.55 (m, 1H), 3.25 (s, 6H), 3.16-3.25 (m, 2H), 2.40-2.50 (m, 2H), 1.57-1.72 (m, 3H), 1.22-1.37 (m, 2H).

Step 8: Preparation of (S)-3-(6-fluoro-5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 41)

The separated (−)-enantiomer from step 7 was first deprotected under the acidic condition and then reacted with the product from step 6 under the same condition as described in step 11 of Compound 87 preparation. LCMS m/z 762.2 [M+H]; $^1$H NMR (400 MHz, DMSO) δ 10.99 (s, 1H), 9.35 (s, 1H), 7.43 (d, J=11.6 Hz, 1H), 7.27-7.16 (m, 4H), 6.82-6.72 (m, 3H), 6.68 (d, J=8.2 Hz, 1H), 6.35-6.28 (m, 3H), 6.15 (d, J=14.1 Hz, 1H), 5.08 (dd, 1H), 4.43-4.18 (m, 5H), 3.63-3.53 (m, 1H), 3.32-3.30 (m, 2H), 3.26-3.20 (m, 2H), 3.12 (br s, 2H), 2.95-2.85 (m, 1H), 2.63-2.48 (m, 7H), 2.42-2.32 (m, 1H), 2.22 (br d, 2H), 2.02-1.91 (m, 1H), 1.81-1.73 (m, 2H), 1.70-1.61 (m, 1H), 1.27-1.20 (m, 2H); HRMS calculated for $C_{44}H_{45}F_2N_5O_5$ exact mass 761.3389, observed [M+1]$^+$ 762.3593.

Example 4: Synthesis of (S)-3-(6-fluoro-5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 42)
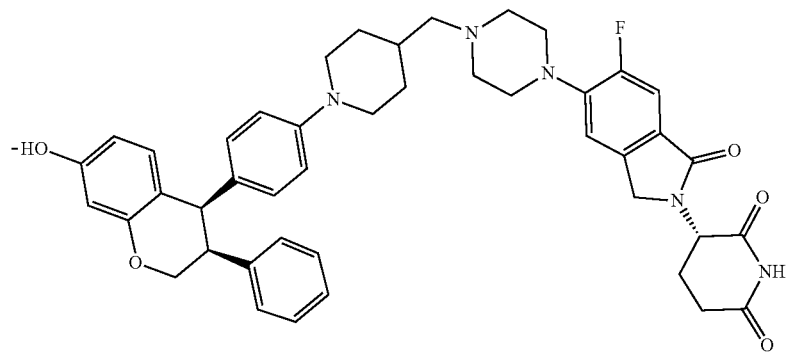
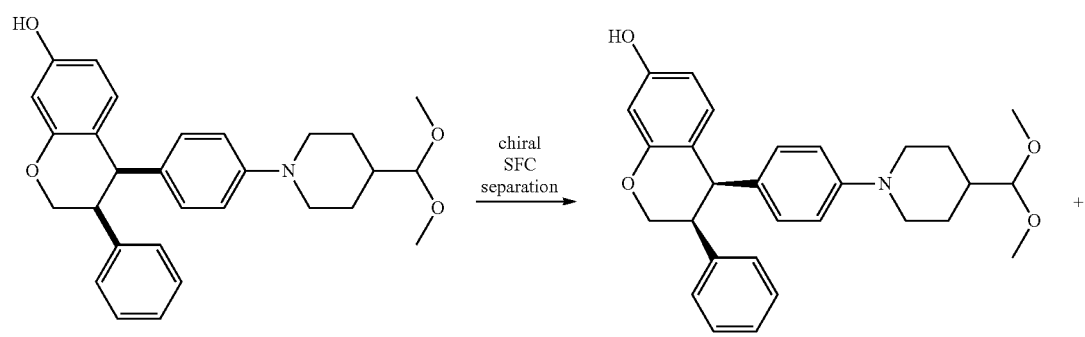
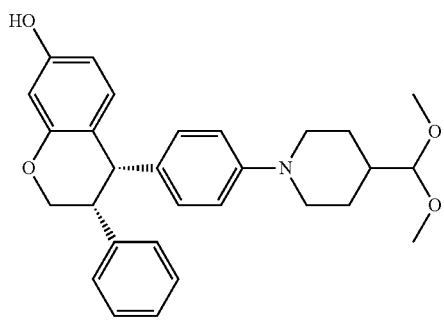
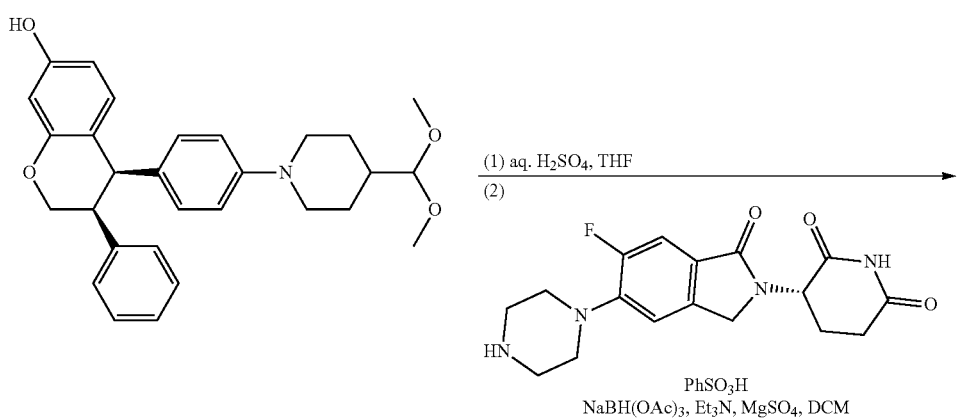

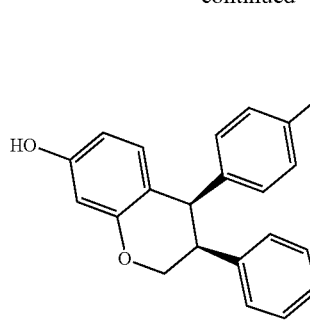
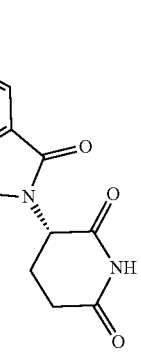

Step 1: Preparation of (3S,4R)-4-(4-(4-(dimethoxymethyl)piperidin-1-yl)phenyl)-3-phenylchroman-7-ol The racemic cis-4-(4-(4-(dimethoxymethyl)piperidin-1-yl)phenyl)-3-phenylchroman-7-ol prepared in step 11 of Compound 36 (49.2 g, 108 mmol) was separated by chiral SFC (column: DAICEL CHIRALCEL OJ (250 mm×50 mm, 10 um); mobile phase: [0.1% NH$_3$H$_2$O MeOH]; B %: 50%-50%, 5.5 min). The first fraction collected provided (3R,4S)-4-(4-(4-(dimethoxymethyl)piperidin-1-yl)phenyl)-3-phenylchroman-7-ol as an off-white solid (19.0 g, 97.8% purity). [α]$_D^{25}$=360.4 (1.34 g/100 mL in EtOAc); LCMS m/z 460.2 [M+1]$^+$; $^1$H NMR (400 MHz, CDCl$_3$) δ 7.11-7.20 (m, 3H), 6.82 (d, J=8.3 Hz, 1H), 6.62-6.73 (m, 4H), 6.43-6.51 (m, 3H), 6.35 (dd, J=8.2, 2.5 Hz, 1H), 4.84 (br s, 1H, OH), 4.43 (t, J=11.2 Hz, 1H), 4.17-4.27 (m, 2H), 4.08 (d, J=7.4 Hz, 1H), 3.53-3.65 (m, 3H), 3.37 (s, 6H), 2.58 (dt, 2H), 1.82 (br d, J=12.8 Hz, 2H), 1.66-1.77 (m, 1H), 1.38-1.49 (m, 2H). The second fraction collected provided (3S,4R)-4-(4-(4-(dimethoxymethyl)piperidin-1-yl)phenyl)-3-phenylchroman-7-ol as an off-white solid (19.0 g, 99.8% purity). [α]$_D^{25}$=−386.8 (0.39 g/100 mL in EtOAc); LCMS m/z 460.2 [M+1]$^+$; $^1$H NMR (400 MHz, CDCl$_3$) δ 7.11-7.20 (m, 3H), 6.82 (d, J=8.3 Hz, 1H), 6.62-6.73 (m, 4H), 6.43-6.51 (m, 3H), 6.35 (dd, J=8.2, 2.5 Hz, 1H), 4.79 (br s, 1H, OH), 4.43 (t, J=11.2 Hz, 1H), 4.17-4.27 (m, 2H), 4.07 (d, J=7.4 Hz, 1H), 3.53-3.65 (m, 3H), 3.37 (s, 6H), 2.58 (dt, 2H), 1.82 (br d, J=12.8 Hz, 2H), 1.66-1.77 (m, 1H), 1.35-1.49 (m, 2H).

Step 2: Preparation of (S)-3-(6-fluoro-5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 42)

This compound was prepared using the separated (−)-enantiomer from step 1 under the same condition as described for the synthesis of compound 41. LCMS m/z 744.2 [M+H]$^+$; $^1$H NMR (400 MHz, DMSO) δ 10.99 (s, 1H), 9.29 (s, 1H), 7.43 (d, J=11.3 Hz, 1H), 7.27-7.12 (m, 4H), 6.80-6.74 (m, 2H), 6.69-6.59 (m, 3H), 6.38 (d, J=8.1 Hz, 2H), 6.33-6.24 (m, 2H), 5.08 (dd, 1H), 4.42-4.15 (m, 5H), 3.67-3.50 (m, 3H), 3.23 (m, 2H), 3.12 (br s, 2H), 2.95-2.85 (m, 1H), 2.67-2.50 (m, 7H), 2.41-2.30 (m, 1H), 2.20 (br d, 2H), 2.02-1.90 (m, 1H), 1.82-1.74 (m, 2H), 1.69-1.60 (m, 1H), 1.26-1.10 (m, 2H); HRMS calculated for C$_{44}$H$_{46}$FN$_5$O$_5$ exact mass 743.3483, observed [M+1]$^+$ 744.3681.

Example 5: Synthesis of (S)-3-(5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 86)

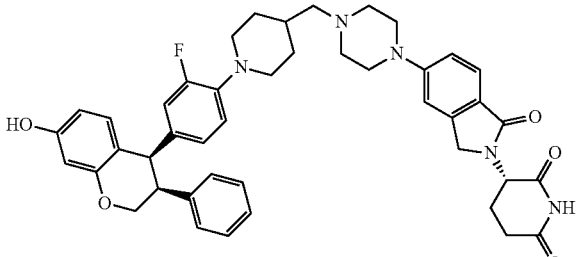

This compound was prepared using the same method as for the preparation of compound 41. The desired compound was obtained as a neutral form of a white solid after purification. LCMS m/z 743.7 [M+H]$^+$; $^1$H NMR (400 MHz, DMSO) δ 10.97 (s, 1H), 9.37 (s, 1H), 7.52 (d, J=8.2 Hz, 1H), 7.17 (m, 3H), 7.07 (s, 1H), 7.06 (d, J=8.2 Hz, 1H), 6.84-6.71 (m, 3H), 6.69 (d, J=8.3 Hz, 1H), 6.37-6.27 (m, 3H), 6.16 (br d, J=12 Hz, 1H), 5.06 (dd, J=12.5 Hz, 4.2 Hz, 1H), 4.40-4.18 (m, 5H), 3.57 (m, 1H), 3.32-3.17 (m, 6H), 2.96-2.87 (m, 1H), 2.60-2.48 (m, 7H), 2.40-2.33 (m, 1H), 2.22 (br d, 2H), 2.00-1.90 (br d, 1H), 1.80-1.75 (m, 2H), 1.70-1.60 (m, 1H), 1.28-1.20 (m, 2H); HRMS calculated for C$_{44}$H$_{46}$FN$_5$O$_5$ exact mass 743.3483, observed [M+1]$^+$ 744.3567.

Example 6: Synthesis of (S)-3-(5-(4-((1-(2-fluoro-4-((3R,4S)-7-hydroxy-3-phenylchroman-4-yl)phenyl)piperidin-4-yl)methyl)piperazin-1-yl)-1-oxoisoindolin-2-yl)piperidine-2,6-dione (Compound 45)

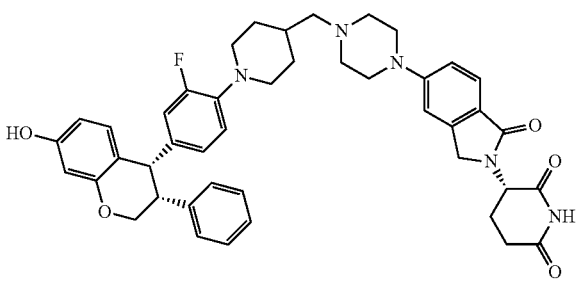

This compound was prepared using the same method as for the preparation of compound 41. LCMS m/z 743.5 [M+H]+; 1H NMR (400 MHz, DMSO) δ 10.97 (s, 1H), 9.37 (s, 1H), 7.53 (d, J=7.4 Hz, 1H), 7.20-7.06 (m, 5H), 6.82-6.78 (m, 2H), 6.78-6.72 (m, 1H), 6.69 (d, J=8.3 Hz, 1H), 6.34-6.29 (m, 3H), 6.16 (d, J=14.3 Hz, 1H), 5.06 (dd, J=13.2, 4.8 Hz, 1H), 4.43-4.09 (m, 5H), 3.59-3.54 (m, 1H), 3.34-3.19 (m, 6H), 2.94-2.86 (m, 1H), 2.69-2.48 (m, 7H), 2.46-2.31 (m, 1H), 2.20 (br, 2H), 1.98-1.92 (m, 1H), 1.85-1.60 (m, 3H), 1.29-1.20 (m, 2H); HRMS calculated for C44H46FN5O5 exact mass 743.3483, observed [M+1]+ 744.3567.

Example 7: Synthesis of (S)-3-(5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione (Compound 33)

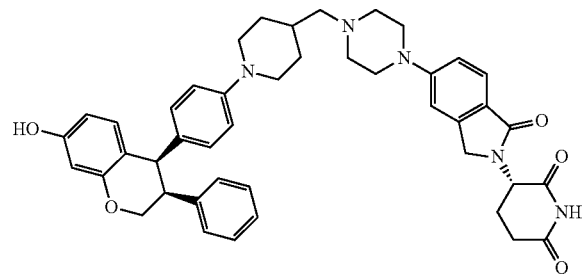 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)ccc3C2=O)C(=O)N1]

This compound was prepared using the same method as for the preparation of compound 41. LCMS m/z 725.7 [M+H]+; 1H NMR (400 MHz, DMSO) δ 10.98 (s, 1H), 9.31 (s, 1H), 7.53-7.51 (m, 1H), 7.25-7.02 (m, 5H), 6.77 (m, 2H), 6.73-6.60 (m, 3H), 6.40 (d, J=8.3 Hz, 2H), 6.33-6.25 (m, 2H), 5.06 (dd, 1H), 4.39-4.31 (m, 2H), 4.26-4.17 (m, 3H), 3.64-3.50 (m, 3H), 3.28-3.25 (br s, 4H), 2.94-2.89 (m, 1H), 2.64-2.48 (m, 7H), 2.41-2.33 (m, 1H), 2.19 (br, 2H), 2.00-1.93 (m, 1H), 1.86-1.60 (m, 3H), 1.29-1.12 (m, 2H); HRMS calculated for C44H47N5O5 exact mass 725.3577, observed [M+1]+ 726.3675.

Example 8: Synthesis of (S)-3-(5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione (Compound 34)

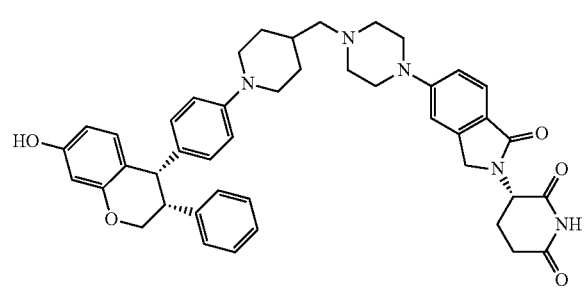 [SMILES: O=C1CC[C@H](N2Cc3cc(N4CCN(CC5CCN(c6ccc([C@H]7c8ccc(O)cc8OC[C@H]7c7ccccc7)cc6)CC5)CC4)ccc3C2=O)C(=O)N1]

This compound was prepared using the same method as for the preparation of compound 41. LCMS m/z 725.5 [M+H]+; 1H NMR (400 MHz, DMSO) δ 10.97 (s, 1H), 9.32 (s, 1H), 7.62-7.58 (m, 1H), 7.34-7.30 (m, 1H), 7.19-7.06 (m, 4H), 6.83-6.74 (m, 2H), 6.72-6.54 (m, 3H), 6.40 (d, J=7.5 Hz, 2H), 6.35-6.20 (m, 2H), 5.07 (br d, J=8.8 Hz, 1H), 4.39-4.30 (m, 2H), 4.27-4.14 (m, 3H), 3.64-3.51 (m, 3H), 3.31-3.27 (m, 4H), 2.94-2.87 (m, 1H), 2.70-2.54 (m, 7H), 2.40-2.31 (m, 1H), 2.24-2.15 (m, 2H), 2.03-1.65 (m, 4H), 1.30-1.20 (m, 2H); HRMS calculated for C44H47N5O5 exact mass 725.3577, observed [M+1]+ 726.3702.

Example 9: Synthesis of cis-(S)-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione (Compound 32)

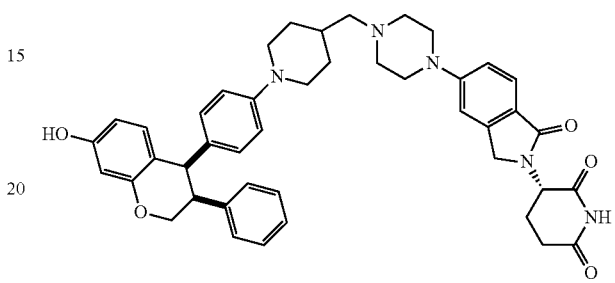

This compound was prepared using the same method as for the preparation of compound 41. LCMS m/z 725.5 [M+H]+; 1H NMR (400 MHz, DMSO) δ 10.97 (s, 1H), 9.31 (s, 1H), 7.62-7.51 (m, 1H), 7.23-7.04 (m, 5H), 6.81-6.74 (m, 2H), 6.71-6.58 (m, 3H), 6.39 (d, J=8.1 Hz, 2H), 6.32 (d, J=2.2 Hz, 1H), 6.31-6.26 (m, 1H), 5.06 (dd, J=13.1, 4.4 Hz, 1H), 4.34 (t, J=11.1 Hz, 2H), 4.28-4.15 (m, 3H), 3.66-3.47 (m, 3H), 3.33-3.26 (m, 4H), 2.96-2.86 (m, 1H), 2.70-2.48 (m, 7H), 2.46-2.31 (m, 1H), 2.20 (br s, 2H), 2.02-1.60 (m, 4H), 1.30-1.15 (m, 2H); HRMS calculated for C44H47N5O5 exact mass 725.3577, observed [M+1]+ 726.3641.

Example 10: cis-(S)-3-(5-(4-((1-(2-fluoro-4-(7-hydroxy-3-phenylchroman-4-yl)phenyl)piperidin-4-yl)methyl)piperazin-yl)-1-oxoisoindolin-2-yl)piperidine-2,6-dione (Compound 85)

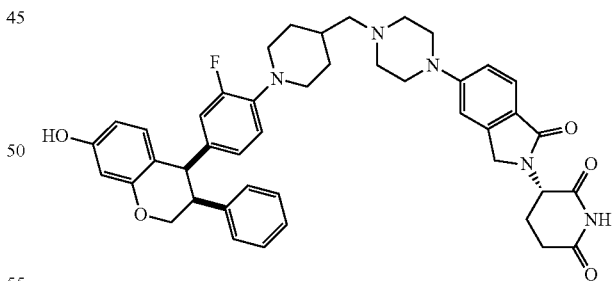

This compound was prepared using the same method as for the preparation of compound 41. LCMS m/z 744.3 [M+H]+; 1H NMR (400 MHz, DMSO) δ 10.96 (s, 1H), 9.37 (s, 1H), 7.57-7.49 (m, 1H), 7.21-7.04 (m, 5H), 6.83-6.67 (m, 4H), 6.37-6.27 (m, 3H), 6.16 (d, J=14.6 Hz, 1H), 5.06 (dd, J=13.3, 5.0 Hz, 1H), 4.41-4.16 (m, 5H), 3.59-3.54 (m, 1H), 3.34-3.16 (m, 6H), 2.95-2.86 (m, 1H), 2.69-2.48 (m, 7H), 2.44-2.33 (m, 1H), 2.20 (br s, 2H), 1.99-1.90 (m, 1H), 1.82-1.74 (m, 1H), 1.72-1.60 (m, 1H), 1.25-1.15 (m, 2H); HRMS calculated for C44H46FN5O5 exact mass 743.3483, observed [M+H]+ 744.3530.

Example 11: Synthesis of cis-(S)-3-(5-(4-((1-(2-fluoro-4-(3-(4-fluoro-3-methylphenyl)-7-hydroxy-chroman-4-yl)phenyl)piperidin-4-yl)methyl)piper-azin-1-yl)-1-oxoisoindolin-2-yl)piperidine-2,6-dione (Compound 60)
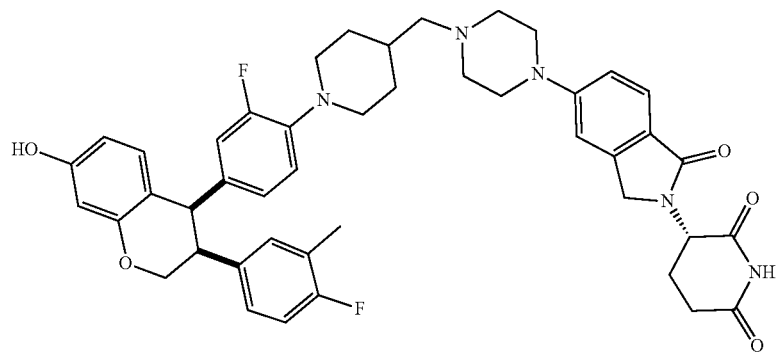
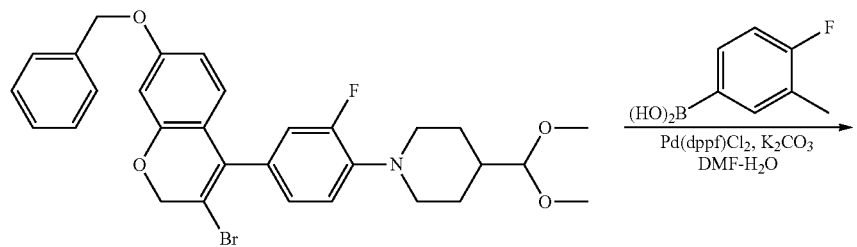
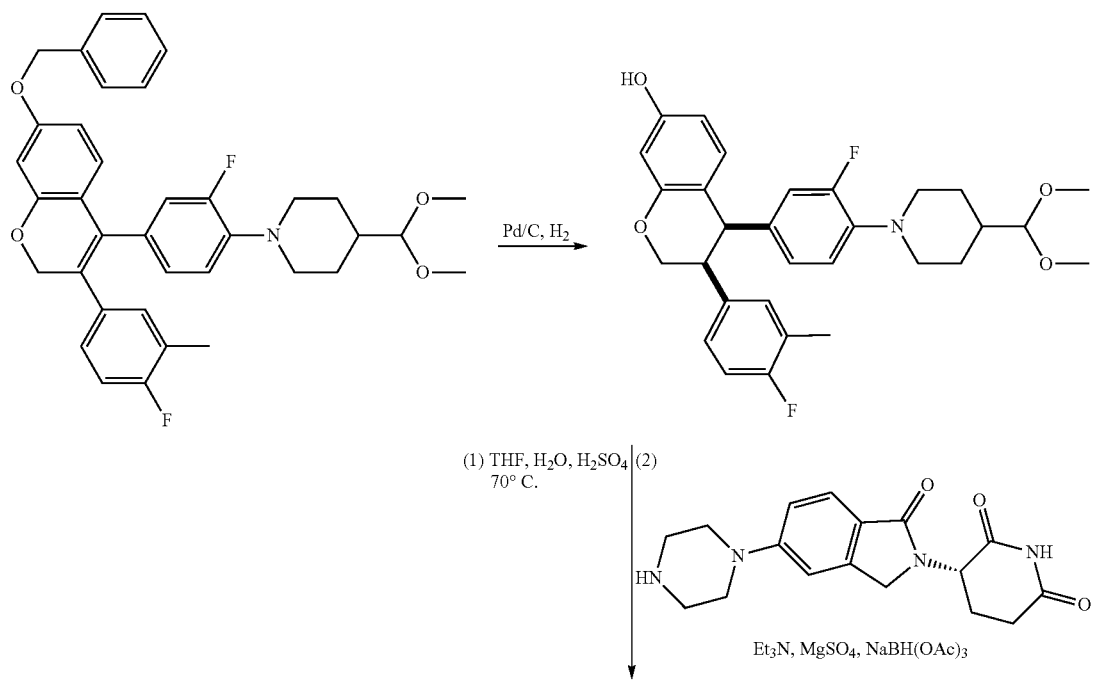

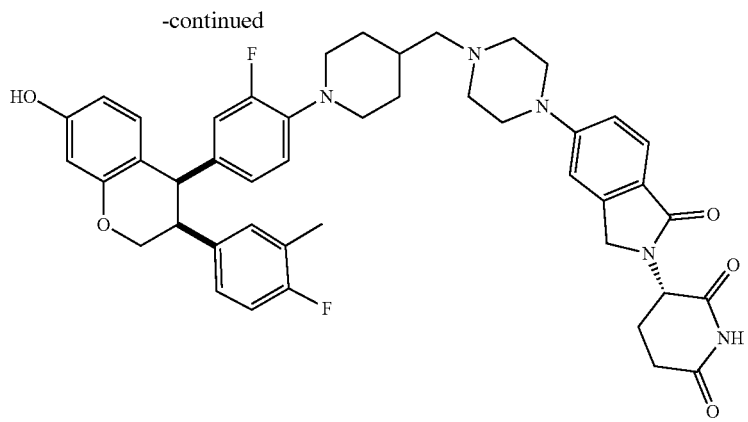

Step 1: Preparation of 1-(4-(7-(benzyloxy)-3-(4-fluoro-3-methylphenyl)-2H-chromen-4-yl)-2-fluorophenyl)-4-(dimethoxymethyl)piperidine To a solution of 1-{4-[7-(benzyloxy)-3-bromo-2H-chromen-4-yl]-2-fluorophenyl}-4-(dimethoxymethyl)piperidine (200 mg, 0.35 mmol), (4-fluoro-3-methylphenyl)boranediol (80.82 mg, 0.52 mmol) and potassium carbonate (145.12 mg, 1.05 mmol) in DMF and H₂O (10 mL/10 mL) stirred under nitrogen atmosphere at room temperature was added 1,1'-Bis(diphenylphosphino)ferrocenepalladiumdichloride (25.60 mg, 0.034 mmol). The reaction mixture was stirred at 90° C. under nitrogen atmosphere for 12 hours. The resulting mixture was evaporated in vacuo to give the crude product which was dissolved in DCM (200 mL), washed with water (20 mL), and evaporated in vacuo. The resulting residue was purified by preparative TLC (petroleum ether/ethyl acetate=2:1) to obtain desired product as a brown solid (150 mg, 0.29 mmol, 71.3% yield).

Step 2: Preparation of cis-4-(4-(4-(dimethoxymethyl)piperidin-1-yl)-3-fluorophenyl)-3-(4-fluoro-3-methylphenyl)chroman-7-ol To a solution of 1-(4-(7-(benzyloxy)-3-(4-fluoro-3-methylphenyl)-2H-chromen-4-yl)-2-fluorophenyl)-4-(dimethoxymethyl)piperidine (130 mg, 0.26 mmol) in THF (20 mL) stirred at room temperature was added palladium/carbon (553.38 mg, 5.2 mmol). The reaction mixture was stirred under hydrogen atmosphere at room temperature for 1 hour. The reaction mixture was filtered, and the filtrate was concentrated to give the desired product as a yellow solid (130 mg, 0.25 mmol, 85.3% yield). LCMS m/z 509.7 [M+1]⁺.

Step 3: Preparation of cis-(S)-3-(5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione (Compound 60)

A solution of 4-(4-(4-(dimethoxymethyl)piperidin-1-yl)-3-fluorophenyl)-3-(4-fluoro-3-methylphenyl)chroman-7-ol (100 mg, 0.2 mmol)) in THF (5 mL) and water (5 ml, with 10% H₂SO₄) was stirred at 70° C. for 1 h. The reaction mixture was dissolved in DCM (200 mL), adjusted pH to 10 with aqueous sodium hydroxide solution (2 M), and the organic layer was evaporated in vacuo to give desired product as a yellow solid (80 mg, 0.17 mmol, 86.3% yield). LCMS m/z 463.7 [M+1]⁺. To this solid (30 mg, 0.06 mmol) was added (S)-3-(1-oxo-5-(piperazin-1-yl)isoindolin-2-yl)piperidine-2,6-dione benzenesulfonate (29.19 mg, 0.06 mmol) and triethylamine (30.35 mg, 0.3 mmol) in DCM (5 mL). The mixture was stirred at room temperature following the addition of MgSO₄ (72.00 mg, 0.60 mmol). The reaction mixture was further stirred at room temperature for 2 h followed by the addition of sodium triacetoxyborohydride portion-wise (38.15 mg, 0.18 mmol) at 0° C. The resulting mixture was stirred at room temperature for 2 h and then filtered. The filtrate was evaporated in vacuo to give the crude product which was purified by preparative TLC (DCM:MeOH=10:1) to obtain the desired product as white solid (20 mg, 0.03 mmol, 50.0% yield). LCMS m/z 775.5 [M+1]⁺; ¹H NMR (400 MHz, DMSO) b=10.95 (s, 1H), 9.36 (s, 1H), 7.52 (d, J=8.3 Hz, 1H), 7.10-7.01 (m, 2H), 6.93 (t, J=9.0 Hz, 1H), 6.77 (t, J=8.8 Hz, 1H), 6.68 (d, J=8.2 Hz, 1H), 6.64-6.59 (m, 2H), 6.36-6.25 (m, 3H), 6.20 (d, J=14.1 Hz, 1H), 5.06 (dd, 1H), 4.36-4.12 (m, 5H), 3.59-3.47 (m, 1H), 3.30-3.19 (m, 6H), 2.90-2.86 (m, 1H), 2.68-2.48 (m, 7H), 2.38-2.29 (m, 1H), 2.23-2.20 (br d, 2H), 2.08 (s, 3H), 2.01-1.92 (m, 1H), 1.79-1.76 (m, 2H), 1.70-1.62 (m, 1H), 1.26-1.15 (m, 2H); HRMS calculated for C45H47F2N5O5 exact mass 775.3545, observed [M+1]⁺ 776.3584

Example 12: Synthesis of cis-(S)-3-(5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione (Compound 52)

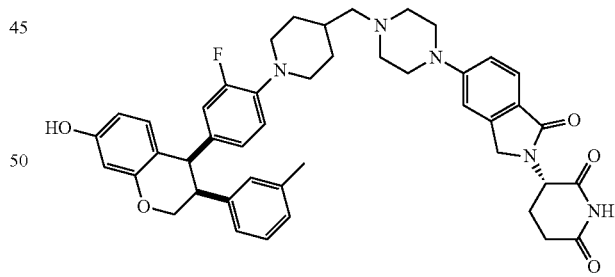

This compound was synthesized according to the same procedure as described in Example 11. LC/MS: 757.5 [M+1]⁺; ¹H NMR (400 MHz, DMSO) b=10.95 (s, 1H), 9.35 (s, 1H), 7.52 (d, J=8.1 Hz, 1H), 7.16-7.02 (m, 3H), 6.98 (d, J=7.8 Hz, 1H), 6.75 (t, J=8.9 Hz, 1H), 6.68 (d, J=8.2 Hz, 1H), 6.58 (d, J=7.4 Hz, 1H), 6.51 (s, 1H), 6.30-6.24 (m, 3H), 6.16 (d, J=13.9 Hz, 1H), 5.06 (dd, 1H), 4.38-4.10 (m, 5H), 3.52-3.47 (m, 1H), 3.30-3.20 (m, 6H), 2.95-2.87 (m, 1H), 2.72-2.48 (m, 7H), 2.42-2.30 (m, 1H), 2.22-2.19 (br, 2H), 2.15 (s, 3H), 1.99-1.90 (m, 1H), 1.78 (m, 2H), 1.70-1.63 (m, 1H), 1.25-1.10 (m, 2H); HRMS calculated for C45H48FN5O5 exact mass 757.3639, observed [M+1]⁺ 758.3681.

Example 13: Synthesis of cis-(S)-3-(5-(4-((1-(4-(3-(3,4-difluorophenyl)-7-hydroxychroman-4-yl)-2-fluorophenyl)piperidin-4-yl)methyl)piperazin-1-yl)-1-oxoisoindolin-2-yl)piperidine-2,6-dione (Compound 84)

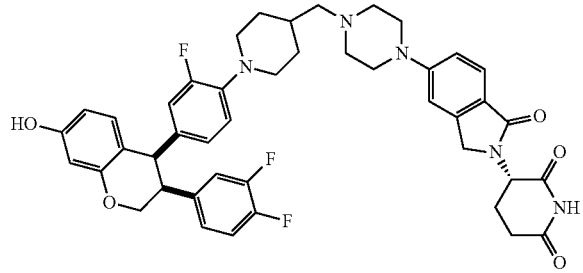

This compound was synthesized according to the same procedure as described in Example 11. LC/MS: m/z 779.4 [M+1]$^+$; $^1$H NMR (400 MHz, DMSO) δ=10.95 (s, 1H), 9.38 (s, 1H), 7.53-7.51 (m, 1H), 7.28-7.21 (m, 1H), 7.08-7.04 (m, 2H), 6.88-6.74 (m, 2H), 6.69-6.66 (m, 2H), 6.34-6.23 (m, 4H), 5.06 (dd, 1H), 4.35-4.15 (m, 5H), 3.65-3.54 (m, 1H), 3.33-3.23 (m, 6H), 2.98-2.84 (m, 1H), 2.62-2.41 (m, 7H), 2.38-2.34 (m, 1H), 2.20 (br d, 2H), 2.03-1.93 (m, 1H), 1.80-1.69 (m, 2H), 1.68-1.60 (m, 1H), 1.26-1.16 (m, 2H); HRMS calculated for C44H44F3N5O5 exact mass 779.3295, observed [M+1]$^+$ 780.3345.

Example 14: Synthesis of cis-(S)-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione (Compound 56)

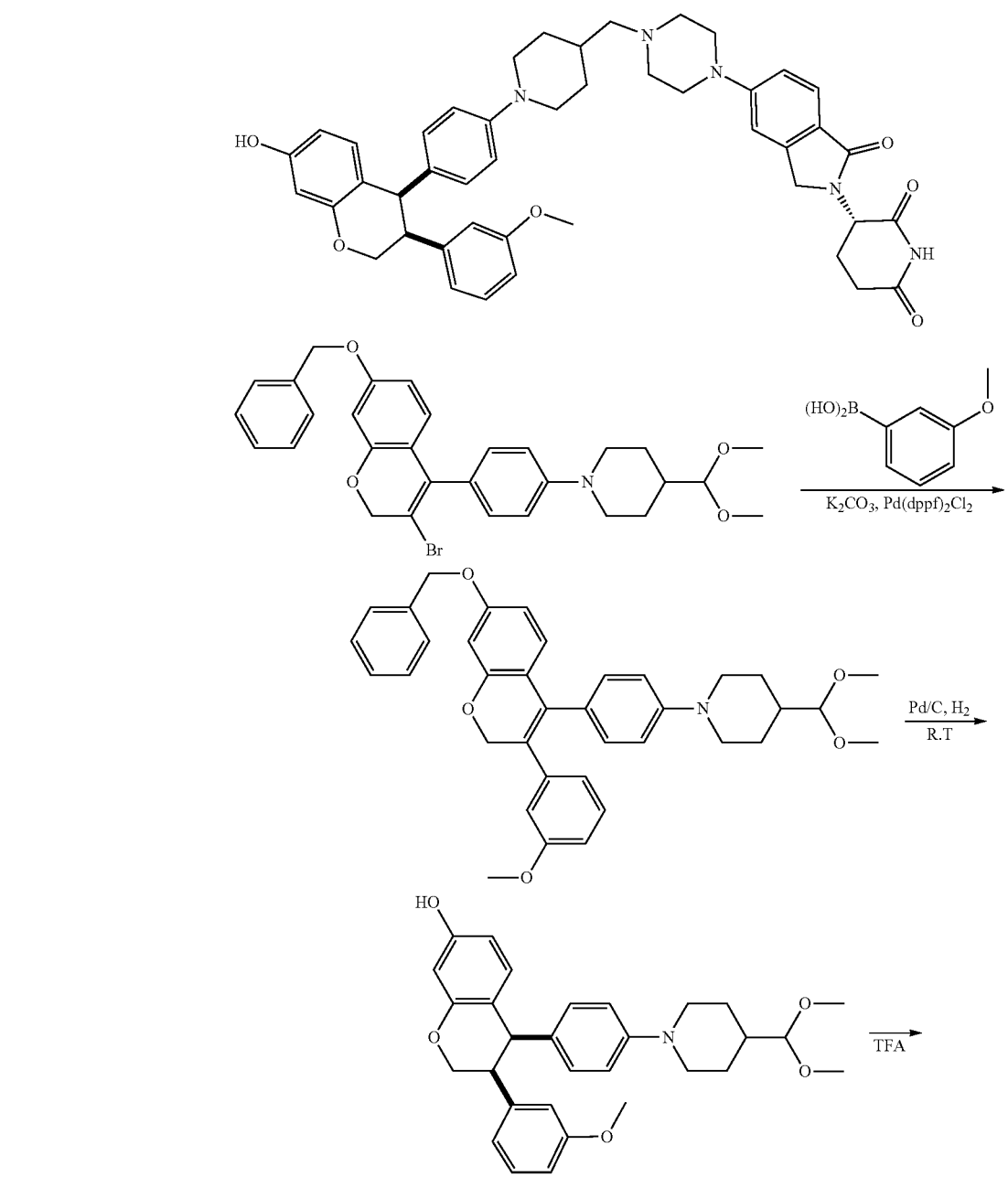

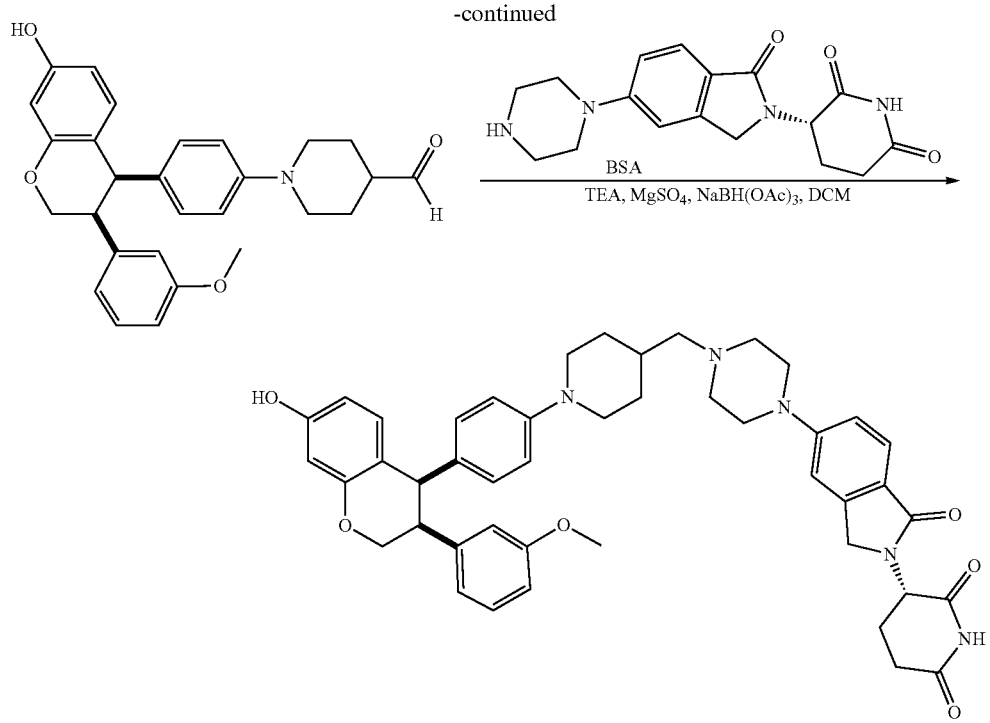

Step 1: Preparation of 1-(4-(7-(benzyloxy)-3-(3-methoxyphenyl)-2H-chromen-4-yl)phenyl)-4-(dimethoxymethyl)piperidine To a solution of 1-{4-[7-(benzyloxy)-3-bromo-2H-chromen-4-yl]phenyl}-4-(dimethoxymethyl)piperidine (100 mg, 0.18 mmol), 3-methoxyphenylboronic acid (41.02 mg, 0.27 mmol) and potassium carbonate (74.63 mg, 0.54 mmol) in DMF/H₂O (20 mL, DMF/H₂O=5:1) stirred under nitrogen at room temperature was added 1,1'-Bis(diphenylphosphino)ferrocenepalladiumdichloride (26.34 mg, 0.036 mmol). The reaction mixture was stirred under nitrogen at 60° C. for 5 hours. The reaction mixture was filtered and evaporated in vacuo to give a crude product. The crude product was dissolved in DCM (200 mL), washed with water (20 mL), and the organic layer was dried over sodium sulfate, filtered and evaporated in vacuo. The resulting residue was purified by preparative TLC (PE:EA=5:1) to give the desired product (80 mg, 0.14 mmol, 76.1% yield) as yellow solid. LC/MS: 578.1 [M+1]$^+$.

Step 2: Preparation of cis-4-(4-(4-(dimethoxymethyl)piperidin-1-yl)phenyl)-3-(3-methoxyphenyl)chroman-7-ol To a solution of 1-{4-[7-(benzyloxy)-3-(3-methoxyphenyl)-2H-chromen-4-yl]phenyl}-4-(dimethoxymethyl)piperidine (100 mg, 0.17 mmol) in THF (15 mL) stirred under hydrogen at room temperature was added palladium/carbon (180 mg). The reaction mixture was stirred at room temperature for 24 hours. The reaction mixture was filtered and evaporated in vacuo to give the desired product (80 mg, 0.16 mmol, 96.1%) as yellow solid. LC/MS: 489.9 [M+1]$^+$.

Step 3: Preparation of cis-1-(4-(7-hydroxy-3-(3-methoxyphenyl)chroman-4-yl)phenyl)piperidine-4-carbaldehyde A solution of cis-4-(4-(4-(dimethoxymethyl)piperidin-1-yl)phenyl)-3-(3-methoxyphenyl)chroman-7-ol (100 mg, 0.2 mmol) in THF/H₂SO₄ (10% aq) (20 mL, THF/H₂SO$_{4=1/1}$) was stirred at 70° C. for 2 hours. The reaction mixture was adjusted to pH about 12 with sodium hydroxide solution (2 mol/L), extracted with DCM (200 mL), dried over sodium sulphate, and evaporated in vacuo to give the desired product (80 mg, 0.18 mmol, 88% yield) as yellow solid. LC/MS: 443.3[M+1]$^+$.

Step 4: Preparation of cis-(S)-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione (Compound 56)

A solution of cis-1-(4-(7-hydroxy-3-(3-methoxyphenyl)chroman-4-yl)phenyl)piperidine-4-carbaldehyde (50 mg, 0.11 mmol), (S)-3-(1-oxo-5-(piperazin-1-yl)isoindolin-2-yl)piperidine-2,6-dione benzenesulphonic acid (24.32 mg, 0.05 mmol), TEA (0.25 mmol) and MgSO₄ (60 mg, 0.5 mmol) in DCM (5 mL) was stirred under nitrogen at room temperature for 30 minutes. Then sodium triacetoxyborohydride (31.79 mg, 0.15 mmol) was added at 0° C. portion-wise. The reaction mixture was stirred at room temperature for 2 hours. The reaction mixture was filtered, the organic layer was washed with water, extracted with DCM (50 mL) to give the crude product. The residue was purified by preparative TLC (DCM:MeOH=10:1) to give the desired product (45 mg, 0.06 mmol, 53%) as a white solid. LC/MS: 756.2 [M+1]$^+$; $^1$H NMR (400 MHz, DMSO) δ 10.95 (s, 1H), 9.27 (s, 1H), 7.52 (d, J=8.6 Hz, 1H), 7.15-6.99 (m, 3H), 6.74-6.59 (m, 4H), 6.42 (d, J=8.6 Hz, 2H), 6.37 (d, J=7.6 Hz, 1H), 6.34-6.16 (m, 3H), 5.06 (dd, 1H), 4.41-4.15 (m, 5H), 3.61-3.52 (m, 5H), 3.50-3.44 (m, 1H), 3.28 (br s, 4H), 2.98-2.84 (m, 1H), 2.66-2.51 (m, 7H), 2.37-2.31 (m, 1H), 2.19 (br d, 2H), 2.02-1.90 (m, 1H), 1.80-1.73 (m, 2H), 1.69-1.60 (m, 1H), 1.25-1.16 m, 2H); HRMS calculated for C45H49N5O6 exact mass 755.3683, observed [M+H]$^+$ 756.3753.

Example 15: Synthesis of cis-(S)-3-(5-(4-((1-(4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione (Compound 63)

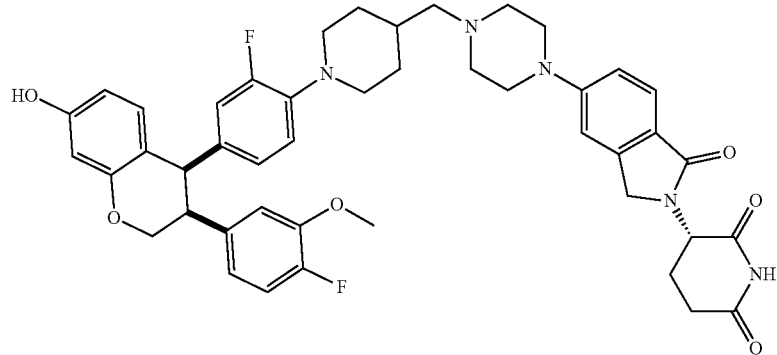

This compound was prepared using the same method as described in Example 14 except 4-fluoro-3-methylphenylboronic acid was used. The crude product from the final reductive amination step was purified by preparative TLC to give the desired compound (65 mg, 0.084 mmol, 38.9% yield) as a white solid. LC/MS: 773.6 [M+1]$^+$; $^1$H NMR (400 MHz, DMSO) δ 10.95 (s, 1H), 9.29 (s, 1H), 7.53 (d, J=8.4 Hz, 1H), 7.12-7.03 (m, 2H), 6.98 (dd, J=11.5, 8.3 Hz, 1H), 6.68 (dd, J=8.5, 2.5 Hz, 3H), 6.44 (d, J=8.5 Hz, 2H), 6.41-6.33 (m, 2H), 6.33-6.25 (m, 2H), 5.05 (dd, J=13.2, 5.0 Hz, 1H), 4.37-4.25 (m, 2H), 4.24-4.18 (m, 1H), 4.18-4.10 (m, 2H), 3.61-3.48 (m, 6H), 3.28 (br s, 4H), 2.96-2.83 (m, 1H), 2.64-2.51 (m, 7H), 2.46-2.29 (m, 1H), 2.20 (br s, 2H), 2.01-1.93 (m, 1H), 1.83-1.74 (m, 2H), 1.73-1.63 (br, 1H), 1.27-1.12 (m, 2H); HRMS calculated for C45H48FN5O6 exact mass 773.3589, observed [M+1]$^+$ 774.3818.

Example 16: Synthesis of cis-(S)-3-(6-fluoro-5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione (Compound 74)

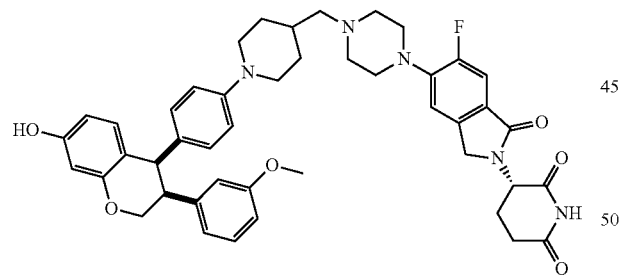

This compound was prepared using the same method as described in Example 14 except (S)-3-(6-fluoro-1-oxo-5-(piperazin-1-yl)isoindolin-2-yl)piperidine-2,6-dione benzenesulfonate was used in the final step of reductive amination. The crude product was purified by preparative TLC (DCM:MeOH=10:1) to give the desired product (25 mg, 48% yield) as white solid. LC/MS: 774.1 [M+1]$^+$; $^1$H NMR (400 MHz, DMSO) b 10.97 (s, 1H), 9.28 (s, 1H), 7.42 (d, J=11.6 Hz, 1H), 7.22 (d, J=7.3 Hz, 1H), 7.05 (t, J=7.9 Hz, 1H), 6.75-6.58 (m, 4H), 6.45-6.33 (m, 3H), 6.30-6.15 (m, 3H), 5.08 (dd, 1H), 4.38-4.09 (m, 5H), 3.58 (s, 3H), 3.57-3.52 (m, 2H), 3.52-3.43 (m, 1H), 3.21-3.04 (m, 4H), 2.99-2.85 (m, 1H), 2.69-2.53 (m, 7H), 2.49-2.28 (m, 1H), 2.20 (brd, 2H), 2.02-1.94 (m, 1H), 1.80-1.60 (m, 3H), 1.30-1.10 (m, 2H); HRMS calculated for C45H48FN5O6 exact mass 773.3589, observed [M+1]$^+$ 774.3688.

Example 17: Synthesis of cis-(S)-3-(5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione (Compound 89)

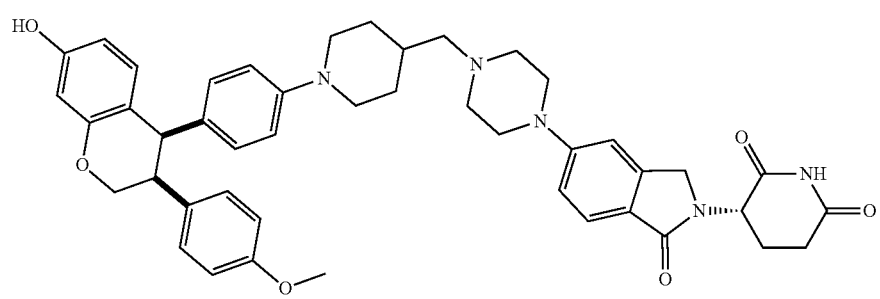

This compound was prepared using the same method as described in Example 14 except 4-methoxyphenylboronic acid was used. The crude product from the final step of reductive amination was purified by preparative TLC (DCM:MeOH=5:1) to give the desired compound as a white solid. LC/MS: 756.2 [M+1]$^+$; $^1$H NMR (400 MHz, DMSO) δ=10.94 (s, 1H), 9.26 (s, 1H), 7.52 (d, J=8.5, 1H), 7.05 (m, 2H), 6.79-6.56 (m, 7H), 6.40 (d, J=8.6, 2H), 6.33-6.23 (m, 2H), 5.08-5.01 (m, 1H), 4.36-4.11 (m, 5H), 3.68 (s, 3H), 3.60-3.52 (m, 2H), 3.48-3.42 (m, 1H), 3.31-3.25 (m, 4H), 2.95-2.84 (m, 1H), 2.67-2.42 (m, 7H), 2.46-2.28 (m, 1H), 2.19 (br d, 2H), 2.00-1.92 (m, 1H), 1.77 (m, 2H), 1.69-1.63 (m, 1H), 1.27-1.10 (m, 2H); HRMS calculated for C45H49N5O6 exact mass 755.3683, observed [M+1]$^+$ 756.3763.

Example 18: Synthesis of cis-(S)-3-(6-fluoro-5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione (Compound 90)

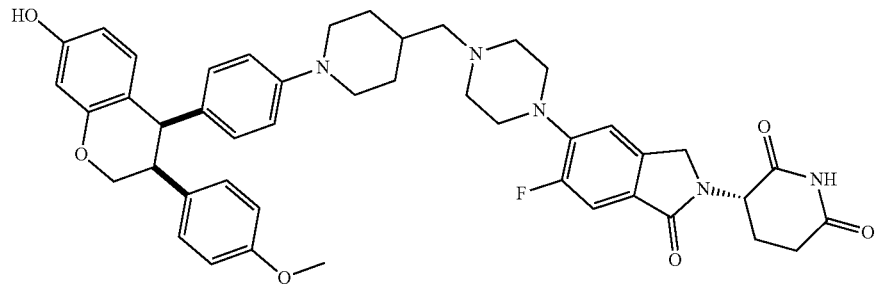

This compound was prepared using the same method as described in Example 17 except (S)-3-(6-fluoro-1-oxo-5-(piperazin-1-yl)isoindolin-2-yl)piperidine-2,6-dione benzenesulfonate was used in the final step of reductive amination. The crude product was purified by preparative TLC (DCM:MeOH=10:1) to give desired compound as a white solid. LC/MS: 774.2 [M+1]*; $^1$H NMR (400 MHz, DMSO) δ 10.98 (s, 1H), 9.30 (s, 1H), 7.43 (d, J=11.5 Hz, 1H), 7.24 (d, J=7.3 Hz, 1H), 6.77-6.57 (m, 7H), 6.40 (d, J=8.5 Hz, 2H), 6.34-6.20 (m, 2H), 5.05 (dd, 1H), 4.45-4.12 (m, 5H), 3.68 (s, 3H), 3.58-3.48 (m, 3H), 3.26-3.05 (m, 4H), 2.95-2.87 (m, 1H), 2.69-2.46 (m, 7H), 2.45-2.28 (m, 1H), 2.22 (br, 2H), 2.03-1.95 (m, 1H), 1.79-1.65 (m, 3H), 1.30-1.16 (m, 2H); HRMS calculated for C45H48FN5O6 exact mass 773.3589, observed [M+1]$^+$774.3648.

Example 19: ERα Degradative Activity of Compounds of the Present Disclosure in T47D. MCF7 and CAMA1 Cells T47D cells were plated in 24-well plates at 1.5×10$^5$ cells/well in the RPMI growth medium containing 10% FBS and 1× Penicillin Streptomycin. MCF7 cells were plated in 24-well plates at 1.5×10$^5$ cells/well in the DMEM growth medium containing 10% FBS and 1× Penicillin Streptomycin. CAMA1 cells were plated in 24-well plates at 2×10$^5$ cells/well in the RPMI growth medium containing 20% FBS and 1× Penicillin Streptomycin. They were then incubated at 37° C. overnight. The following day, the test compound was administered to the cells by using 1000× compound stock solution prepared in DMSO at various concentrations. After administration of the compound, the cells were then incubated at 37° C. for 6 hours.

Upon completion, the cells were washed with PBS and protein was collected in Laemmli sample buffer (1×; VWR International). Proteins in cell lysate were separated by SDS-PAGE and transferred to Odyssey nitrocellulose membranes (Licor) with Iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-ER (Cell Signaling, 8644) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-mouse IgG (1:20,000, Licor) or IRDye® 800CW goat anti-rabbit IgG (1:20,000, Licor) for 1 hour. After TBS-T washes, membranes were rinsed in TBS and scanned on Odyssey® CLx Imaging System (Licor). The bands were quantified using Image Studio™ Software (Licor).

Figure 2A:
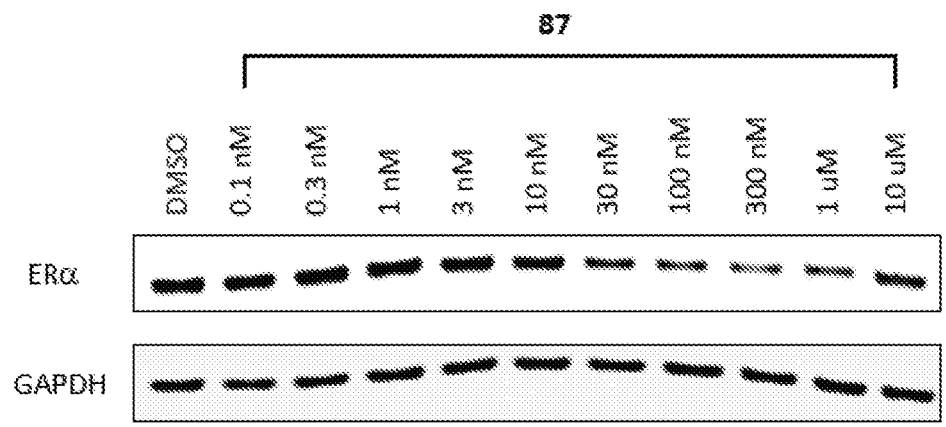
FIGS. 2A and 2B illustrate the ERα degradative activity of exemplary Compounds 87 and 84 of the present disclosure in a T47D cell line 6 hours after administration.
Figure 2B:
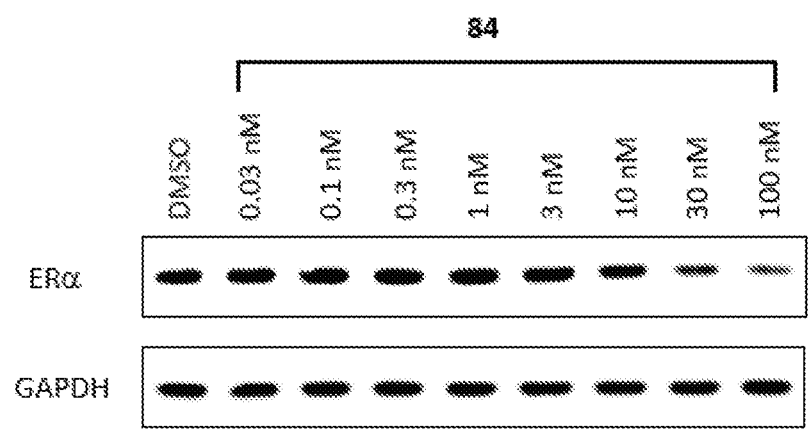
Figure 4A:
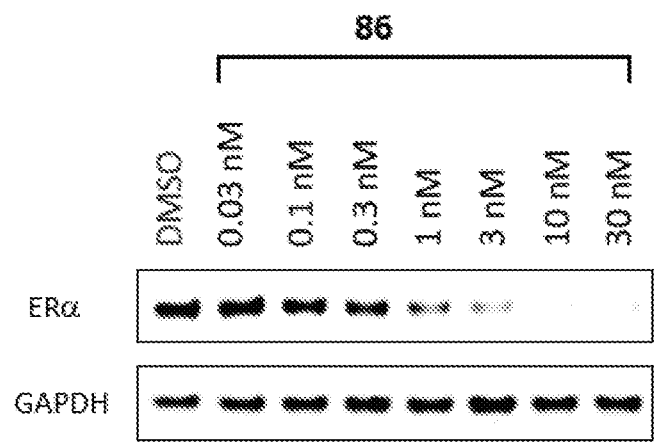
FIGS. 4A and 4B illustrate the ERα degradative activity of exemplary Compounds 86 and 33 of the present disclosure in a T47D cell line 6 hours after administration.
Figure 4B:
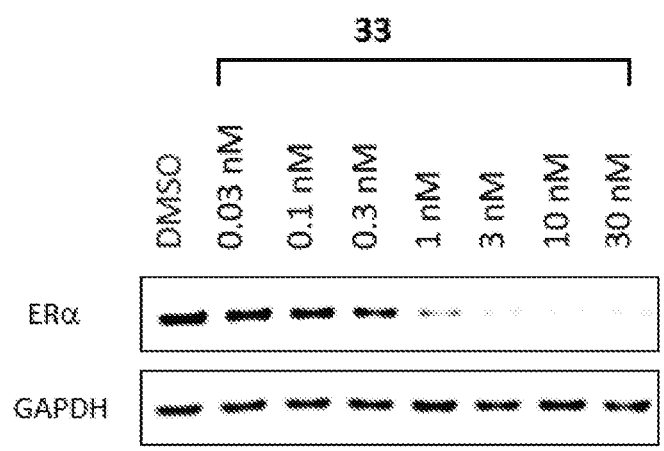
Figure 6A:
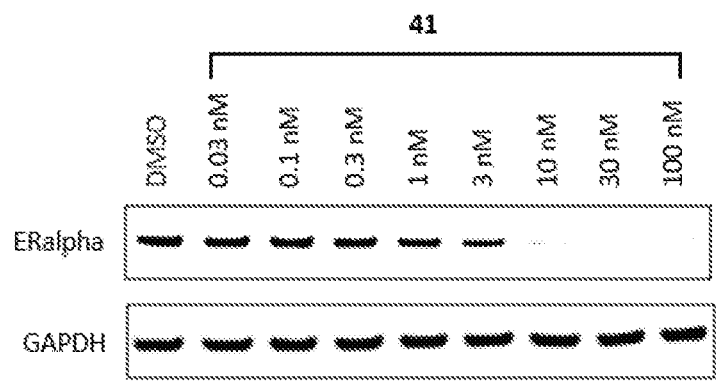
FIGS. 6A, 6B and 6C illustrate the ERα degradative activity of exemplary Compounds 41, 42 and 63 of the present disclosure in a T47D cell line 6 hours after administration.
Figure 6B:
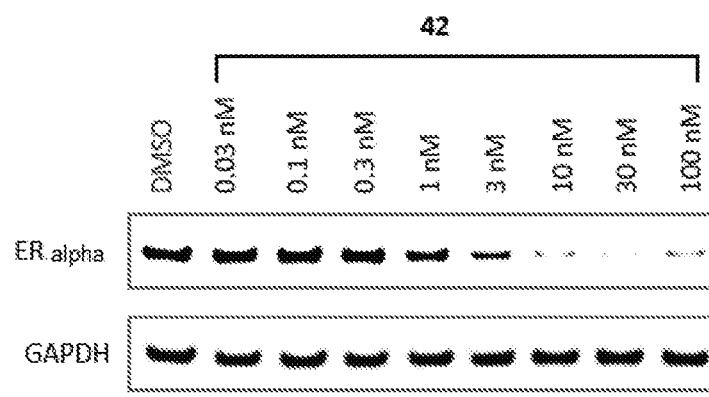
Figure 6C:
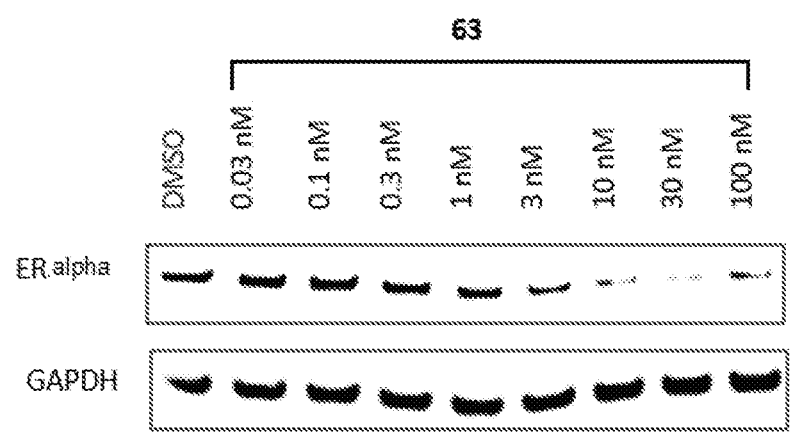
Figure 7A:
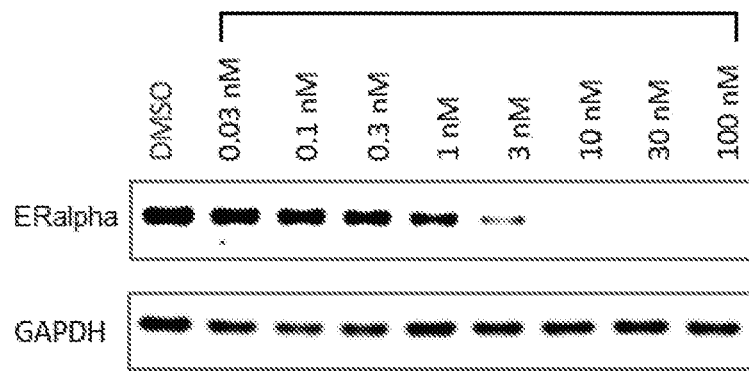
FIGS. 7A, 7B, 7C and 7D illustrate the ERα degradative activity of exemplary Compounds 89, 56, 90 and 74 of the present disclosure in a T47D cell line 6 hours after administration.
Figure 7B:
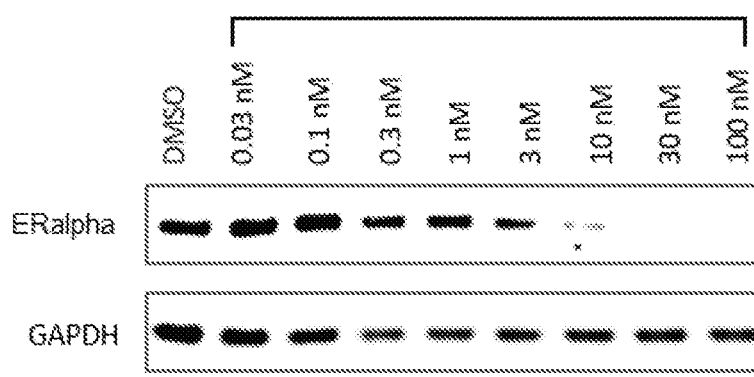
Figure 7C:
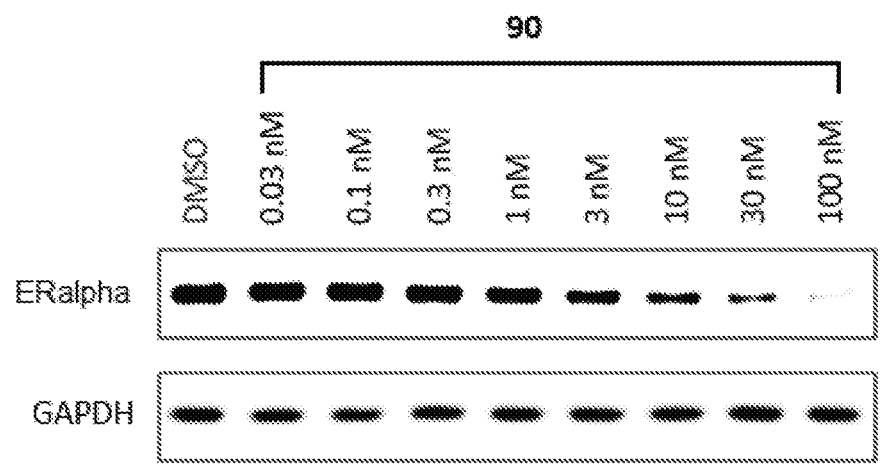
Figure 7D:
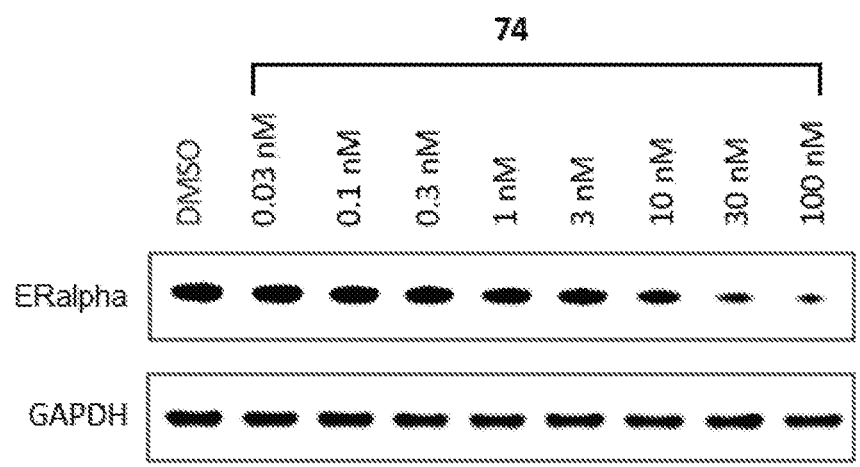

FIGS. 1A to 1D illustrate the ERα degradative activity of exemplary Compounds 85, 60, 32 and 52 of the present disclosure in a T47D cell line 6 hours after administration. FIGS. 2A and 2B illustrate the ERα degradative activity of exemplary Compounds 87 and 84 of the present disclosure in a T47D cell line 6 hours after administration. FIGS. 4A and 4B illustrate the ERα degradative activity of exemplary Compounds 86 and 33 of the present disclosure in a T47D cell line 6 hours after administration. FIG. 6A to 6C illustrate the ERα degradative activity of exemplary Compounds 41, 42 and 63 of the present disclosure in a T47D cell line 6 hours after administration. FIG. 7A to 7D illustrate the ERα degradative activity of exemplary Compounds 89, 56, 90 and 74 of the present disclosure in a T47D cell line 6 hours after administration.

Table 3 illustrates the ERα degradative activity of exemplary compounds of the present disclosure in T47D cell line 6 hours after administration.

TABLE 3

| ERα degradative activity of exemplary compounds in T47D cell line | |
|---|---|
| Compound # | DC50 (nM) in T47D |
| 32 | 2.4 |
| 33 | 0.3 |
| 34 | >100 |
| 36 | >10 |
| 41 | 4 |
| 42 | 1.1 |
| 45 | >100 |
| 52 | 5.6 |
| 56 | 1.7 |

TABLE 3-continued

ERα degradative activity of exemplary
compounds in T47D cell line

| Compound # | DC50 (nM) in T47D |
|---|---|
| 60 | 6.5 |
| 63 | 2.1 |
| 74 | 7.3 |
| 84 | 9.3 |
| 85 | 3 |
| 86 | 0.5 |
| 87 | 12.6 |
| 89 | 0.7 |
| 90 | 9.6 |

Figure 3A:
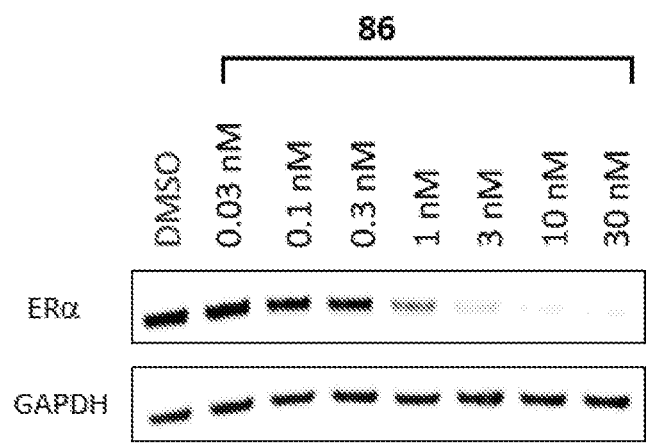
FIGS. 3A and 3B illustrate the ERα degradative activity of exemplary Compounds 86 and 33 of the present disclosure in a MCF7 cell line 6 hours after administration.
Figure 3B:
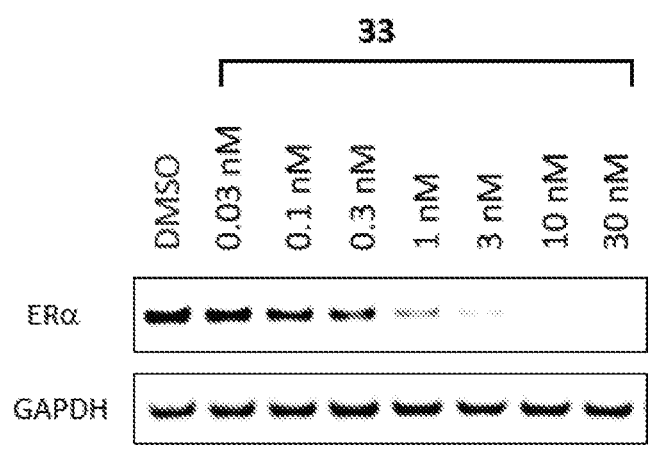

FIGS. 3A and 3B illustrate the ERα degradative activity of exemplary Compounds 86 and 33 of the present disclosure in a MCF7 cell line 6 hours after administration.

Figure 5A:
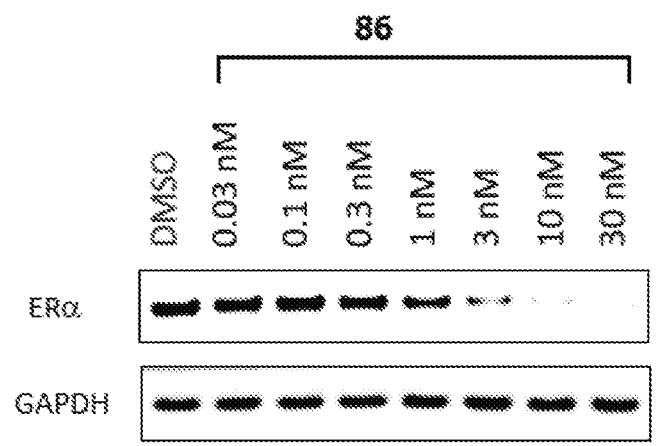
FIGS. 5A and 5B illustrate the ERα degradative activity of exemplary Compounds 86 and 33 of the present disclosure in a CAMA-1 cell line 6 hours after administration.
Figure 5B:
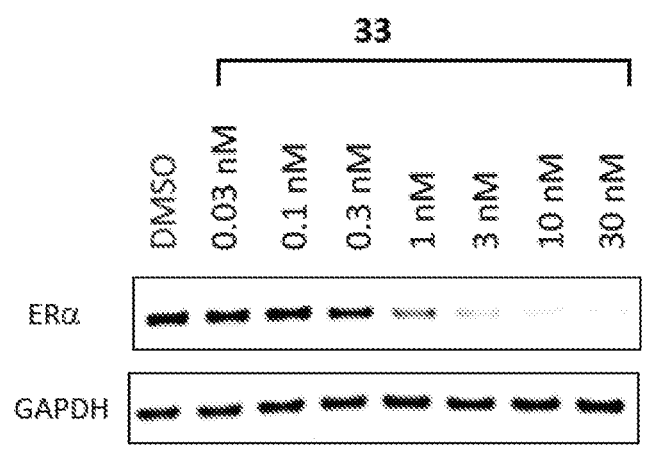

FIGS. 5A and 5B illustrate the ERα degradative activity of exemplary Compounds 86 and 33 of the present disclosure in a CAMA1 cell line 6 hours after administration.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula (I), a stereoisomer or a mixture of stereoisomers, a pharmaceutically acceptable salt, or hydrate thereof:

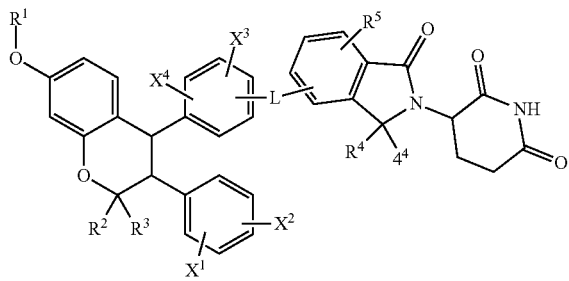

Formula (I)

wherein:
$R^1$ is selected from H, $C_1$-$C_6$ acyl or $C_1$-$C_6$ alkyl, each of which is substituted with 0, 1, 2, or 3 $R^6$;
$R^2$ and $R^3$ are each independently selected from H, $C_1$-C3 alkyl, or $C_1$-$C_3$ haloalkyl, each of which is substituted with 0, 1, 2, or 3 $R^6$;
each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo;
$R^5$ is selected from halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^6$;
$X^1$ and $X^2$ are each independently selected from H, halogen, cyano, $C_1$-$C_6$ alkyl, $C_1$-$C_6$ alkoxyl, or $C_1$-$C_6$ haloalkyl each of which is substituted with 0, 1, 2, or 3 $R^6$;
$X^3$ and $X^4$ are each independently selected from H or halo;
L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is substituted with 0, 1, 2, or 3 $R^6$;
each $R^6$ is independently selected from $C_1$-$C_6$ alkyl, halo, cyano, and hydroxy,
each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

2. The compound according to claim 1, or a pharmaceutically acceptable salt thereof, wherein $R^1$ is selected from H or methyl.

3. The compound according to claim 1, or a pharmaceutically acceptable salt thereof, wherein $R^2$ and $R^3$ are each independently selected from H and methyl.

4. The compound according to claim 1, or a pharmaceutically acceptable salt thereof, wherein $R^4$ is H.

5. The compound according to claim 1, or a pharmaceutically acceptable salt thereof, wherein two $R^4$ groups are taken together to form an oxo.

6. The compound according to claim 1, or a pharmaceutically acceptable salt thereof, wherein $R^5$ is selected from halogen.

7. The compound according to claim 1, or a pharmaceutically acceptable salt thereof, wherein $X^1$ and $X^2$ are each independently selected from H, F, CN, methyl, methoxy, trifluoromethyl.

8. The compound according to claim 7, or a pharmaceutically acceptable salt thereof, wherein $X^3$ and $X^4$ are each independently selected from H or halo.

9. The compound according to claim 7, or a pharmaceutically acceptable salt thereof, wherein $X^3$ and $X^4$ are each independently selected from H or F.

10. The compound according to claim 1, or pharmaceutically acceptable salt thereof, wherein L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is independently substituted with 0, 1, 2, or 3 $R^6$.

11. The compound according to claim 1, or a pharmaceutically acceptable salt thereof, wherein L is a linker wherein one carbon atom is replaced by a heterocycle and one carbon atom is replaced by a cycloalkyl, each of which is independently substituted with 0, 1, 2, or 3 $R^6$.

12. The compound according to claim 1, or a pharmaceutically acceptable salt thereof, wherein L is selected from

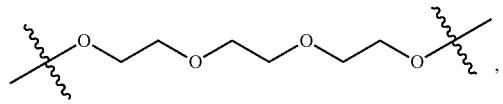

-continued

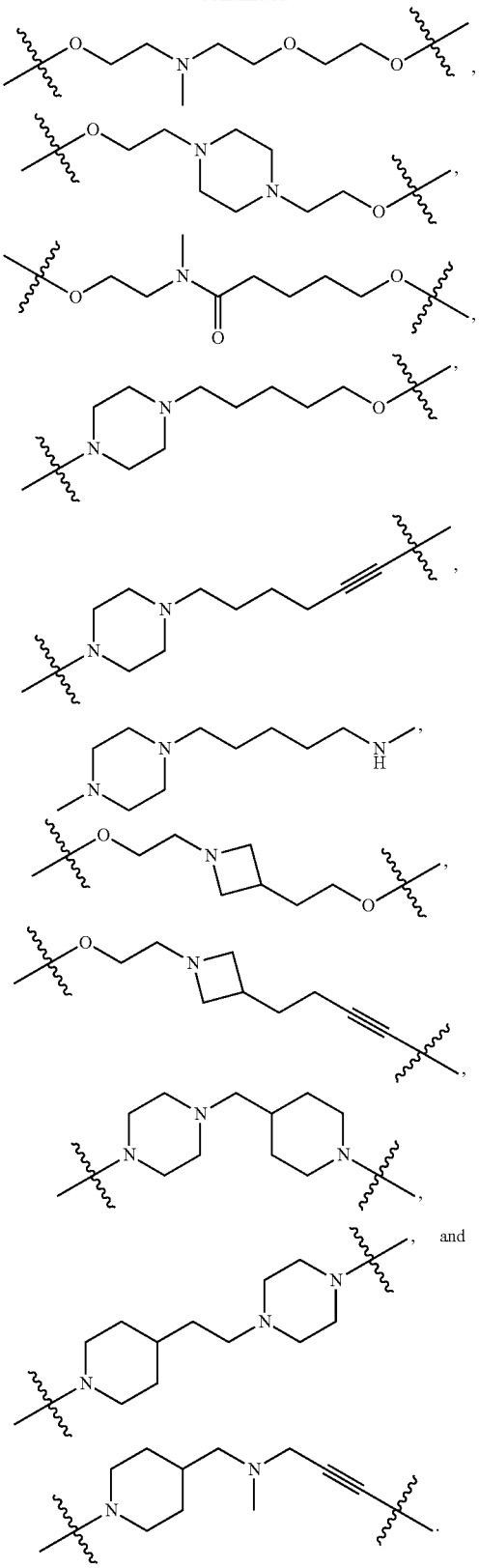

13. The compound according to claim 1, or a pharmaceutically acceptable salt thereof, wherein the compound is stereoisomer.

14. The compound according to claim 13, wherein the compound is cis-isomer.

15. The compound according to claim 13, wherein the compound has a Formula (I)*:

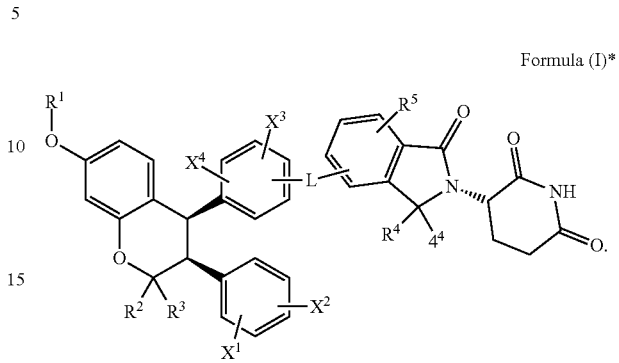

Formula (I)*

16. A compound, or a pharmaceutically acceptable salt thereof, selected from:
cis-3-(5-(2-(2-(2-(4-(7-hydroxy-3-phenylchroman-4-yl)phenoxy)ethoxy)ethoxy)ethoxy)-1-oxoisoindolin-2-yl)piperidine-2,6-dione;
cis-3-(5-(2-(2-((2-(4-(7-hydroxy-3-phenylchroman-4-yl)phenoxy)ethyl)(methyl)amino)ethoxy)ethoxy)-1-oxoisoindolin-2-yl)piperidine-2,6-dione;
cis-3-(5-(2-(4-(2-(4-(7-hydroxy-3-phenylchroman-4-yl)phenoxy)ethyl)piperazin-1-yl)ethoxy)-1-oxoisoindolin-2-yl)piperidine-2,6-dione;
cis-5-((2-(2,6-dioxopiperidin-3-yl)-1-oxoisoindolin-5-yl)oxy)-N-(2-(4-(7-hydroxy-3-phenylchroman-4-yl)phenoxy)ethyl)-N-methylpentanamide;
cis-3-(5-((5-(4-(4-(7-hydroxy-3-phenylchroman-4-yl)phenyl)piperazin-1-yl)pentyl)oxy)-1-oxoisoindolin-2-yl)piperidine-2,6-dione;
cis-3-(5-(6-(4-(4-(7-hydroxy-3-phenylchroman-4-yl)phenyl)piperazin-1-yl)hex-1-yn-1-yl)-1-oxoisoindolin-2-yl)piperidine-2,6-dione;
cis-3-(4-(6-(4-(4-(7-hydroxy-3-phenylchroman-4-yl)phenyl)piperazin-1-yl)hex-1-yn-1-yl)-1-oxoisoindolin-2-yl)piperidine-2,6-dione;
cis-2-(2,6-dioxopiperidin-3-yl)-5-((5-(4-(4-(7-hydroxy-3-phenylchroman-4-yl)phenyl)piperazin-1-yl)pentyl)amino)isoindoline-1,3-dione;
cis-3-(5-(3-(1-(2-(4-(7-hydroxy-3-phenylchroman-4-yl)phenoxy)ethyl)azetidin-3-yl)propoxy)-1-oxoisoindolin-2-yl)piperidine-2,6-dione;
cis-3-(5-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione;
cis-3-(4-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione;
cis-2-(2,6-dioxopiperidin-3-yl)-5-(4-(5-(4-(7-hydroxy-3-phenylchroman-4-yl)phenoxy)pentyl)piperazin-1-yl)isoindoline-1,3-dione;
cis-3-(5-(4-(5-(4-(7-hydroxy-3-phenylchroman-4-yl)phenoxy)pentyl)piperazin-1-yl)-1-oxoisoindolin-2-yl)piperidine-2,6-dione;
cis-3-(5-(4-(5-(2-fluoro-4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione;
cis-3-(5-(4-(5-(2-fluoro-4-(3-(4-fluorophenyl)-7-hydroxychroman-4-yl)phenoxy)pentyl)piperazin-1-yl)-1-oxoisoindolin-2-yl)piperidine-2,6-dione;

cis-3-(5-(4-(5-(2-fluoro-4-(3-(4-fluoro-3-methylphenyl)-7-hydroxychroman-4-yl)phenoxy)pentyl)piperazin-1-yl)-1-oxoisoindolin-2-yl)piperidine-2,6-dione;

cis-3-(5-(4-(5-(2-fluoro-4-(7-hydroxy-3-(m-tolyl)chroman-4-yl)phenoxy)pentyl)piperazin-1-yl)-1-oxoisoindolin-2-yl)piperidine-2,6-dione;

cis-3-(5-(4-(5-(2-fluoro-4-(3-(4-fluoro-2-methylphenyl)-7-hydroxychroman-4-yl)phenoxy)pentyl)piperazin-1-yl)-1-oxoisoindolin-2-yl)piperidine-2,6-dione;

cis-3-(5-(4-(5-(4-(3,4-difluorophenyl)-7-hydroxychroman-4-yl)-2-fluorophenoxy)pentyl)piperazin-1-yl)-1-oxoisoindolin-2-yl)piperidine-2,6-dione;

cis-3-(5-(4-(5-(4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione;

cis-3-(5-(4-(5-(4-(3-(4-fluoro-3-methoxyphenyl)-7-hydroxychroman-4-yl)phenoxy)pentyl)piperazin-1-yl)-1-oxoisoindolin-2-yl)piperidine-2,6-dione;

cis-3-(5-(4-(5-(4-(3-(4-fluoro-2-(trifluoromethyl)phenyl)-7-hydroxychroman-4-yl)phenoxy)pentyl)piperazin-1-yl)-1-oxoisoindolin-2-yl)piperidine-2,6-dione;

cis-3-(5-(4-(5-(4-(3-(4-fluoro-3-methylphenyl)-7-hydroxychroman-4-yl)phenoxy)pentyl)piperazin-1-yl)-1-oxoisoindolin-2-yl)piperidine-2,6-dione;

cis-3-(5-(4-(5-(4-(7-hydroxy-3-(o-tolyl)chroman-4-yl)phenoxy)pentyl)piperazin-1-yl)-1-oxoisoindolin-2-yl)piperidine-2,6-dione;

cis-3-(5-(4-(4-(4-(7-hydroxy-3-phenylchroman-4-yl)phenoxy)butyl)piperazin-1-yl)-1-oxoisoindolin-2-yl)piperidine-2,6-dione;

cis-3-(5-(4-(5-(4-(7-hydroxy-2,2-dimethyl-3-phenylchroman-4-yl)phenoxy)pentyl)piperazin-1-yl)-1-oxoisoindolin-2-yl)piperidine-2,6-dione;

cis-3-(5-(4-(5-(4-(7-methoxy-3-phenylchroman-4-yl)phenoxy)pentyl)piperazin-1-yl)-1-oxoisoindolin-2-yl)piperidine-2,6-dione;

3-(5-(4-(5-(4-((2R,3S,4R)-7-hydroxy-2-methyl-3-phenylchroman-4-yl)phenoxy)pentyl)piperazin-1-yl)-1-oxoisoindolin-2-yl)piperidine-2,6-dione;

3-(5-(4-(5-(4-((2S,3S,4R)-7-hydroxy-2-methyl-3-phenylchroman-4-yl)phenoxy)pentyl)piperazin-1-yl)-1-oxoisoindolin-2-yl)piperidine-2,6-dione;

3-(5-(4-(5-(4-((2R,3R,4S)-7-hydroxy-2-methyl-3-phenylchroman-4-yl)phenoxy)pentyl)piperazin-1-yl)-1-oxoisoindolin-2-yl)piperidine-2,6-dione;

3-(5-(4-(5-(4-((2S,3R,4S)-7-hydroxy-2-methyl-3-phenylchroman-4-yl)phenoxy)pentyl)piperazin-1-yl)-1-oxoisoindolin-2-yl)piperidine-2,6-dione;

cis-(S)-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione;

cis-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione;

cis-2-(2,6-dioxopiperidin-3-yl)-5-(4-((1-(4-(7-hydroxy-3-phenylchroman-4-yl)phenyl)piperidin-4-yl)methyl)piperazin-1-yl)isoindoline-1,3-dione;

cis-2-(2,6-dioxopiperidin-3-yl)-5-(4-(2-(1-(4-(7-hydroxy-3-phenylchroman-4-yl)phenyl)piperidin-4-yl)ethyl)piperazin-1-yl)isoindoline-1,3-dione;

cis-2-(2,6-dioxopiperidin-3-yl)-5-fluoro-6-(4-((1-(4-(7-hydroxy-3-phenylchroman-4-yl)phenyl)piperidin-4-yl)methyl)piperazin-1-yl)isoindoline-1,3-dione;

cis-(S)-3-(6-fluoro-5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione;

cis-(S)-3-(6-fluoro-5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione;

(S)-3-(6-fluoro-5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione;

(S)-3-(6-fluoro-5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione;

(S)-3-(6-fluoro-5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione;

cis-(S)-3-(5-(4-(2-(1-(4-(7-hydroxy-3-phenylchroman-4-yl)phenyl)piperidin-4-yl)ethyl)piperazin-1-yl)-1-oxoisoindolin-2-yl)piperidine-2,6-dione;

(S)-3-(5-(4-((1-(2-fluoro-4-((3R,4S)-7-hydroxy-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((3S,4R)-7-hydroxy-2,2-dimethyl-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((2R,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((2S,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((3S,4R)-7-methoxy-3-phenylchroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(3-(4-fluorophenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(4-(3-(4-fluorophenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((3S,4R)-7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione;

cis-(S)-3-(5-(4-((1-(4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(4-((2R)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione;

cis-(S)-3-(5-(4-((1-(4-((2S)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione;

cis-3-(5-(3-(((1-(4-(7-hydroxy-3-(3-methoxyphenyl)chroman-4-yl)phenyl)piperidin-4-yl)methyl)(methyl)amino)prop-1-yn-1-yl)-1-oxoisoindolin-2-yl)piperidine-2,6-dione;

cis-3-(5-(3-(((1-(2-fluoro-4-(7-hydroxy-3-(3-methoxyphenyl)chroman-4-yl)phenyl)piperidin-4-yl)methyl)(methyl)amino)prop-1-yn-1-yl)-1-oxoisoindolin-2-yl)piperidine-2,6-dione;

cis-3-(5-(3-(((1-(2-fluoro-4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione;

cis-3-(5-(3-(((1-(4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione;

cis-(S)-3-(6-fluoro-5-(4-((1-(2-fluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-2-(2,6-dioxopiperidin-3-yl)-5-fluoro-6-(4-((1-(2-fluoro-4-(7-hydroxy-3-(3-methoxyphenyl)chroman-4-yl)phenyl)piperidin-4-yl)methyl)piperazin-1-yl)isoindoline-1,3-dione;

cis-(S)-3-(6-fluoro-5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-2-(2,6-dioxopiperidin-3-yl)-5-fluoro-6-(4-((1-(4-(7-hydroxy-3-(3-methoxyphenyl)chroman-4-yl)phenyl)piperidin-4-yl)methyl)piperazin-1-yl)isoindoline-1,3-dione;

cis-(S)-3-(6-fluoro-5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(6-fluoro-5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(6-fluoro-5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione;

cis-(S)-3-(6-fluoro-5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione;

cis-(S)-3-(6-fluoro-5-(4-((1-(2-fluoro-4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione;

cis-(S)-3-(5-(4-((1-(2,6-difluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(2-fluoro-4-(7-methoxy-3-phenylchroman-4-yl)phenyl)piperidin-4-yl)methyl)piperazin-1-yl)-1-oxoisoindolin-2-yl)piperidine-2,6-dione;

cis-2-(2,6-dioxopiperidin-3-yl)-5-(4-((1-(2-fluoro-4-(7-methoxy-3-phenylchroman-4-yl)phenyl)piperidin-4-yl)methyl)piperazin-1-yl)isoindoline-1,3-dione;

cis-(S)-3-(5-(4-((1-(4-(3-(3,4-difluorophenyl)-7-hydroxychroman-4-yl)-2-fluorophenyl)piperidin-4-yl)methyl)piperazin-1-yl)-1-oxoisoindolin-2-yl)piperidine-2,6-dione;

cis-(S)-3-(5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione;

(S)-3-(5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione;

cis-2-(2,6-dioxopiperidin-3-yl)-5-(4-((1-(2-fluoro-4-(7-hydroxy-3-phenylchroman-4-yl)phenyl)piperidin-4-yl)methyl)piperazin-1-yl)isoindoline-1,3-dione;

cis-(S)-3-(5-(4-((1-(2,6-difluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione;

cis-(S)-3-(5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione; and cis-(S)-3-(6-fluoro-5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione.

17. A pharmaceutical composition comprising a therapeutically effective amount of the compound according to claim 1 or claim 16 and at least one additional component selected from pharmaceutically acceptable carriers, pharmaceutically acceptable vehicles, and pharmaceutically acceptable excipients.

18. A method of treating cancer in a subject in need thereof, comprising administering to said subject an effective amount of the compound according to claim 1 or of the pharmaceutical composition according to claim 17, wherein the cancer is selected from breast cancer, lung cancer, ovarian cancer, endometrial cancer, prostate cancer, and esophageal cancer.

19. The method according to claim 18, wherein the cancer is positive for ERα.

20. The method according to claim 18, wherein the subject has been previously treated with an anti-cancer agent.

21. The method according to claim 20, wherein the anti-cancer agent is selected from tamoxifen or fulvestrant.

22. A method of treating a disease or condition in a subject in need thereof, comprising administering to said subject an effective amount of the compound according to claim 1 or claim 16, wherein the disease or condition is selected from breast cancer, lung cancer, ovarian cancer, endometrial cancer, prostate cancer, esophageal cancer, infertility, ovulatory dysfunction, postmenopausal osteoporosis, estrogen-related gynecomastia, dyspareunia due to menopause, retroperitoneal fibrosis, and idiopathic sclerosing mesenteritis.

* * * * *